US011291379B2

(12) United States Patent
Paak et al.

(10) Patent No.: US 11,291,379 B2
(45) Date of Patent: Apr. 5, 2022

(54) METHOD AND SYSTEM TO ASSESS DISEASE USING DYNAMICAL ANALYSIS OF CARDIAC AND PHOTOPLETHYSMOGRAPHIC SIGNALS

(71) Applicant: Analytics For Life Inc., Toronto (CA)

(72) Inventors: Mehdi Paak, Toronto (CA); Timothy William Fawcett Burton, Toronto (CA); Shyamlal Ramchandani, Kingston (CA)

(73) Assignee: Analytics for Life Inc., Toronto (CA)

( * ) Notice: Subject to any disclaimer, the term of this patent is extended or adjusted under 35 U.S.C. 154(b) by 0 days.

(21) Appl. No.: 16/831,380

(22) Filed: Mar. 26, 2020

(65) Prior Publication Data

US 2020/0397324 A1 Dec. 24, 2020

Related U.S. Application Data

(60) Provisional application No. 62/863,005, filed on Jun. 18, 2019, provisional application No. 62/862,991, filed on Jun. 18, 2019.

(51) Int. Cl.
*A61B 5/024* (2006.01)
*A61B 5/1455* (2006.01)
(Continued)

(52) U.S. Cl.
CPC .......... *A61B 5/02433* (2013.01); *A61B 5/021* (2013.01); *A61B 5/0205* (2013.01);
(Continued)

(58) Field of Classification Search
CPC ....... A61B 5/72; A61B 5/7275; A61B 5/7246; A61B 5/02; A61B 5/02416
See application file for complete search history.

(56) References Cited

U.S. PATENT DOCUMENTS 8,923,958 B2 12/2014 Gupta et al.
9,289,150 B1 3/2016 Gupta et al.
(Continued)

FOREIGN PATENT DOCUMENTS

WO 2019/075391 4/2019

OTHER PUBLICATIONS

Allen, J., "Photoplethysmography and its application in clinical physiological measurement," Physiological Measurement, vol. 28, No. 3, 2007, pp. R1-R39.
(Continued)

*Primary Examiner* — Puya Agahi
(74) *Attorney, Agent, or Firm* — Meunier Carlin & Curfman LLC

(57) ABSTRACT

The exemplified methods and systems facilitate one or more dynamical analyses that can characterize and identify synchronicity between the acquired cardiac signals and photoplethysmographic signals to predict/estimate the presence, non-presence, localization, and/or severity of abnormal cardiovascular conditions or disease, including, for example, but not limited to, coronary artery disease, heart failure (including but not limited to indicators of disease or conduction such as abnormal left ventricular end-diastolic pressure disease), and pulmonary hypertension, among others. In some embodiments, statistical properties of the synchronicity between the cardiac signals and photoplethysmographic signals are evaluated. In some embodiments, statistical properties of a histogram of the synchronicity between the cardiac signals and photoplethysmographic signals are evaluated. In some embodiments, statistical and/or geometric properties of a Poincaré map of synchronicity between the cardiac signals and photoplethysmographic signals are evaluated.

21 Claims, 33 Drawing Sheets

(51) Int. Cl.

| | | |
|---|---|---|
| A61B 5/021 | (2006.01) | |
| A61B 5/00 | (2006.01) | |
| A61B 5/349 | (2021.01) | |
| A61B 5/318 | (2021.01) | |
| A61B 5/0205 | (2006.01) | |

(52) U.S. Cl.
CPC ...... *A61B 5/02416* (2013.01); *A61B 5/02427* (2013.01); *A61B 5/14551* (2013.01); *A61B 5/318* (2021.01); *A61B 5/349* (2021.01); *A61B 5/4842* (2013.01); *A61B 5/7239* (2013.01); *A61B 5/7264* (2013.01); *A61B 5/7275* (2013.01)

(56) References Cited

U.S. PATENT DOCUMENTS

| | | | |
|---|---|---|---|
| 9,408,543 | B1 | 8/2016 | Gupta et al. |
| 9,597,021 | B1 | 3/2017 | Gupta et al. |
| 9,737,229 | B1 | 8/2017 | Gupta et al. |
| 9,910,964 | B2 | 3/2018 | Burton et al. |
| 9,968,265 | B2 | 5/2018 | Burton et al. |
| 10,039,468 | B2 | 8/2018 | Gupta et al. |
| 2009/0326401 | A1 | 12/2009 | Jonckheere et al. |
| 2011/0112382 | A1 | 5/2011 | Li et al. |
| 2013/0158375 | A1* | 6/2013 | Lynn ................ A61B 5/04012 600/324 |
| 2014/0180136 | A1 | 6/2014 | Su et al. |
| 2015/0051500 | A1 | 2/2015 | Elliott et al. |
| 2016/0256060 | A1* | 9/2016 | Katra .................. A61B 5/7275 |
| 2017/0119272 | A1 | 5/2017 | Gupta et al. |
| 2018/0000371 | A1 | 1/2018 | Gupta et al. |
| 2018/0033991 | A1 | 2/2018 | Yamashita |
| 2018/0078146 | A1 | 3/2018 | Shadforth et al. |
| 2018/0160917 | A1* | 6/2018 | Liu .................... A61B 5/02141 |
| 2018/0199893 | A1* | 7/2018 | Hubner ............... A61B 5/0816 |
| 2018/0249960 | A1 | 9/2018 | Gupta et al. |
| 2018/0261328 | A1 | 9/2018 | Burton et al. |
| 2019/0026430 | A1 | 1/2019 | Grouchy et al. |
| 2019/0117164 | A1 | 4/2019 | Gupta et al. |
| 2019/0200893 | A1 | 7/2019 | Grouchy et al. |
| 2019/0214137 | A1 | 7/2019 | Gupta et al. |
| 2019/0365265 | A1 | 12/2019 | Grouchy et al. |
| 2019/0384757 | A1 | 12/2019 | Garrett et al. |
| 2020/0100693 | A1* | 4/2020 | Velo ...................... A61B 5/681 |
| 2020/0205739 | A1 | 7/2020 | Garrett et al. |
| 2020/0205745 | A1 | 7/2020 | Khosousi et al. |
| 2020/0211713 | A1 | 7/2020 | Shadforth et al. |

OTHER PUBLICATIONS

Billingsley, P., "Ergodic Theory and Information," vol. 1, Wiley New York, 1965.
Chatterjee, A., "An introduction to the proper orthogonal decomposition," Current Science, vol. 78, No. 7, 2000, pp. 808-817.
Chen, T., et al., "XGBoost: A Scalable Tree Boosting System," Proceedings of the 22$^{nd}$ International Conference on Knowledge Discovery and Data Mining (KDD'16), ACM, 2016, pp. 785-794.
Dubin, D., "Rapid Interpretation of EKG's: An Interactive Course," Cover Publishing Company, 2000.
Fihn, S. D., et al., "2012 ACCF/AHA/ACP/AATS/PCNA/SCAI/STS Guideline for the Diagnosis and Management of Patients with Stable Ischemic Heart Disease: Executive Summary," Journal of the American College of Cardiology, vol. 60, No. 24, 2012, pp. 2564-2603.
Galiatsatos, P., et al., "Usefulness of a Noninvasive Device to Identify Elevated Left Ventricular Filling Pressure Using Finger Photoplethysmography During a Valsalva Maneuver," American Journal of Cardiology, vol. 119, No. 7, 2017, pp. 1053-1060.
Glass, L., "Synchronization and rhythmic processes in physiology," Nature, vol. 410, 2001, pp. 277-284.
Glass, L., et al., "Time Delays, Oscillations, and Chaos in Physiological Control Systems," Mathematical Biosciences, vol. 90, Issues 1-2, 1988, pp. 111-125.
Goldberger, A. L., et al., "Chaos and Fractals in Human Physiology," Scientific American, vol. 262, No. 2, 1990, pp. 43-49.
Goldberger, A. L. "Nonlinear dynamics, Fractals and Chaos: Applications to Cardiac Electrophysiology," Annals of Biomedical Engineering, vol. 18, No. 2, 1990, pp. 195-198.
Grassberger, P., et al., "Estimation of the Kolmogorov entropy from a chaotic signal," Rapid Communications, Physical Review A, vol. 28, No. 4, 1983, pp. 2591-2593.
Hansson, G. K., "Inflammation, atherosclerosis, and coronary artery disease," The New England Journal of Medicine, vol. 352, No. 16, 2005, pp. 1685-1695.
Jahmunah, V., et al., "Automated detection of schizophrenia using nonlinear signal processing methods," Artificial Intelligence in Medicine, vol. 100, 2019, 18 pages.
Kern, M. J., et al., "Hemodynamic Rounds Series II: The LVEDP," Catheterization and Cardiovascular Diagnosis, vol. 44, No. 1, 1998, pp. 70-74.
Kolmogorov, A. N., "On the Entropy per Unit of Time as a Metric Invariant of Automorphisms," C.R. (Doklady) Russian Academy of Sciences, No. 4, vol. 124, 1959, 3 pages.
Kononenko, I., "Machine Learning for Medical Diagnosis: History, State of the Art and Perspective," Artificial Intelligence in Medicine, vol. 23, No. 1, 2001, 25 pages.
Levine, G. N., et al., "2011 ACCF/AHA/SCAI Guideline for Percutaneous Coronary Intervention: Executive Summary," Journal of the American College of Cardiology, vol. 58, No. 24, 2011, pp. 2550-2583.
Lloyd-Jones, D, et al., "Executive Summary: Heart Disease and Stroke Statistics—2010 Update, A Report from the American Heart Association," Circulation, vol. 121, No. 7, 2010, pp. 948-954.
Mensah, G. A., et al., "An Overview of Cardiovascular Disease Burden in the United States," Health Affairs, vol. 26, No. 1, 2007, pp. 38-48.
Mielniczuk, L. M., et al., "Left Ventricular End-Diastolic Pressure and Risk of Subsequent Heart Failure in Patients Following an Acute Myocardial Infarction," Congestive Heart Failure, vol. 13, No. 4, 2007, pp. 209-214.
Mobley, B. A., et al., "Predictions of coronary artery stenosis by artificial neural network," Artificial Intelligence in Medicine, vol. 18, No. 3, 2000, pp. 187-203.
Ommen, S. R., et al., "Clinical Utility of Doppler Echocardiography and Tissue Doppler Imaging in the Estimation of Left Ventricular Filling Pressures, A Comparative Simultaneous Doppler-Catheterization Study," Circulation, vol. 102, No. 15, 2000, pp. 1788-1794.
Owis, M. I., et al., "Study of features based on nonlinear dynamical modeling in ECG arrhythmia detection and classification," IEEE Transactions on Biomedical Engineering, vol. 49, No. 7, 2002, pp. 733, 736.
Park, J.-H., et al., "Use and Limitations of E/e' to Assess Left Ventricular Filling Pressure by Echocardiography," Journal of Cardiovascular Ultrasound, vol. 19, No. 4, 2011, pp. 169-173.
Patel, V. L., et al., "The Coming of Age of Artificial Intelligence in Medicine," Artificial Intelligence in Medicine, vol. 46, No. 1, 2009, pp. 5-17.
Pedregosa, F., et al., "Scikit-learn: Machine Learning in Python," Journal of Machine Learning Research, vol. 12, 2011, pp. 2825-2830.
Pikovsky, A., et al., "Synchronization: A Universal Concept in Nonlinear Sciences," vol. 12, Cambridge University Press, 2003.
Reddy, Y. N., et al., "Comparing Pulmonary Arterial Wedge Pressure and Left Ventricular End Diastolic Pressure for Assessment of Left-Sided Filling Pressures," JAMA Cardiology, vol. 3, No. 6, 2018, pp. E1-E2.
Reisner, A., et al., "Utility of the Photoplethysmogram in Circulatory Monitoring," Anesthesiology, vol. 108, No. 5, 2008, pp. 950-958.

(56) References Cited

OTHER PUBLICATIONS

Russo, J. J., et al., "Left Ventricular Unloading During Extracorporeal Membrane Oxygenation in Patients with Cardiogenic Shock," Journal of the American College of Cardiology, vol. 73, No. 6, 2019, pp. 654-662.

Salem, R., et al., "Left ventricular end-diastolic pressure is a predictor of mortality in cardiac surgery independently of left ventricular ejection fraction," British Journal of Anaesthesia, vol. 97, No. 3, 2006, pp. 292-297.

Sauer, T., et al., "Embedology," Journal of Statistical Physics, vol. 65, Nos. 3-4, 1991, pp. 579-616.

Strogatz, S. H., "Nonlinear Dynamics and Chaos: With Applications to Physics, Biology, Chemistry, and Engineering," CRC Press, 2018.

Tai, A. M., et al., "Machine learning and big data: Implications for disease modeling and therapeutic discovery in psychiatry," Artificial Intelligence in Medicine, vol. 99, 2019, 11 pages.

Theiler, J., "Efficient Algorithm for Estimating the Correlation Dimension from a Set of Discrete Points," Physical Review A, vol. 36, No. 9, 1987, pp. 4456-4462.

Voss, A., et al., "Methods derived from nonlinear dynamics for analysing heart rate variability," Philosophical Transactions of the Royal Society A: Mathematical, Physical and Engineering Sciences, vol. 367, No. 1887, 2008, pp. 277-296.

Wolf, J. B., et al., "Determining Lyapunov Exponents from a Time Series," Physica D: Nonlinear Phenomena, vol. 16, No. 3, 1985, pp. 285-317.

Zou, H., et al., "Regularization and variable selection via the elastic net," Journal of the Royal Statistical Society: Series B (Statistical Methodology), vol. 67, Part 2, 2005, pp. 301-320.

International Search Report and Written Opinion, dated Jun. 12, 2020, received in connection with corresponding International Patent Application No. PCT/IB2020/052890.

\* cited by examiner

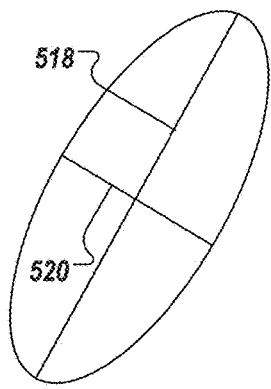
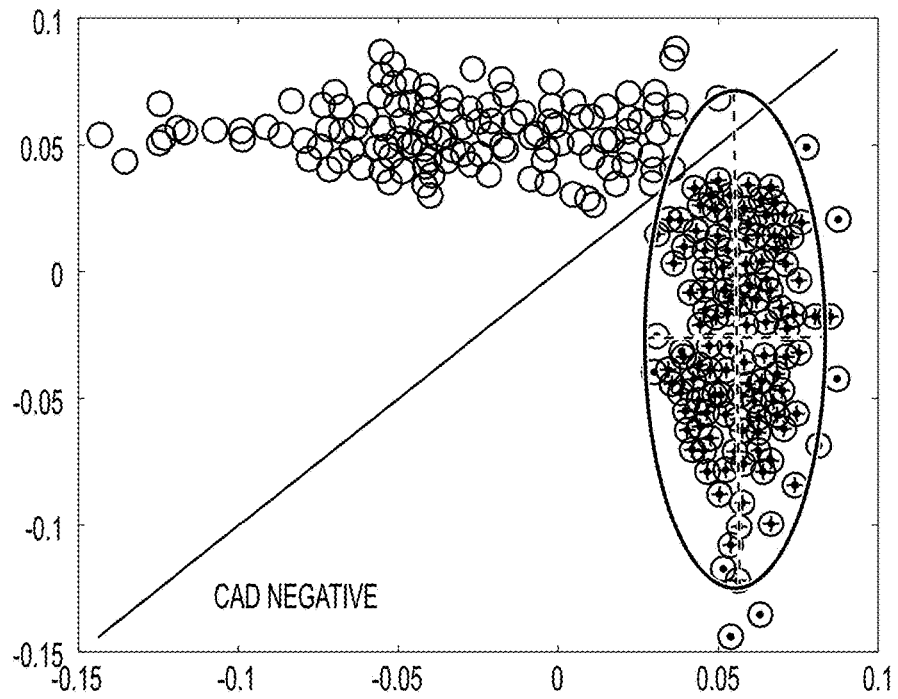
FIG. 5E
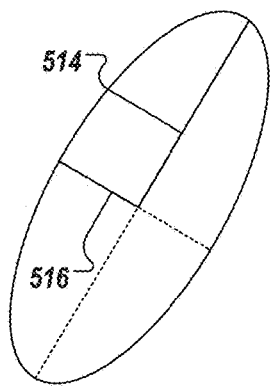
FIG. 5D
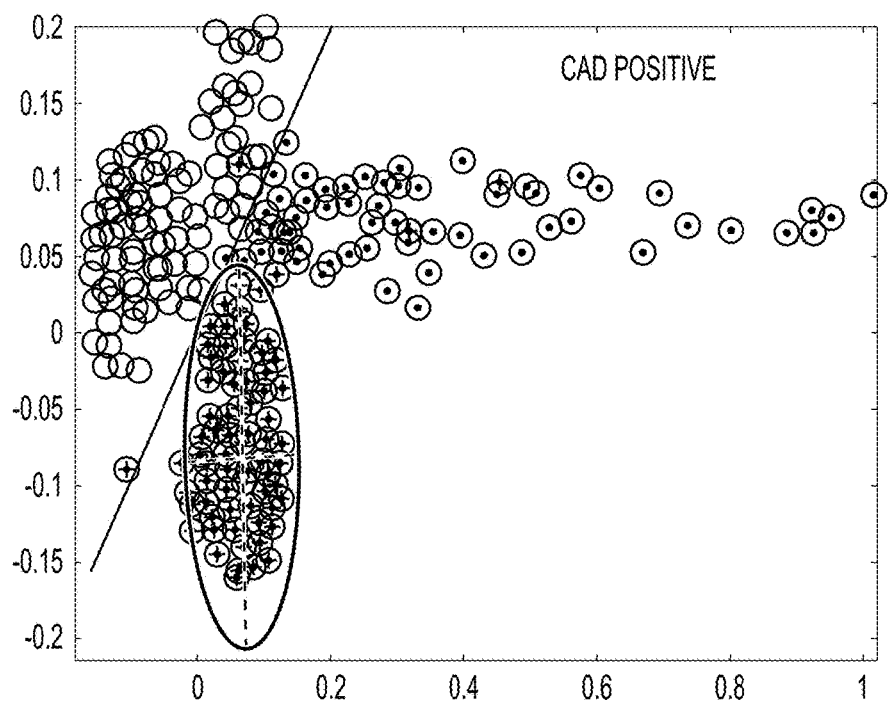
FIG. 5F

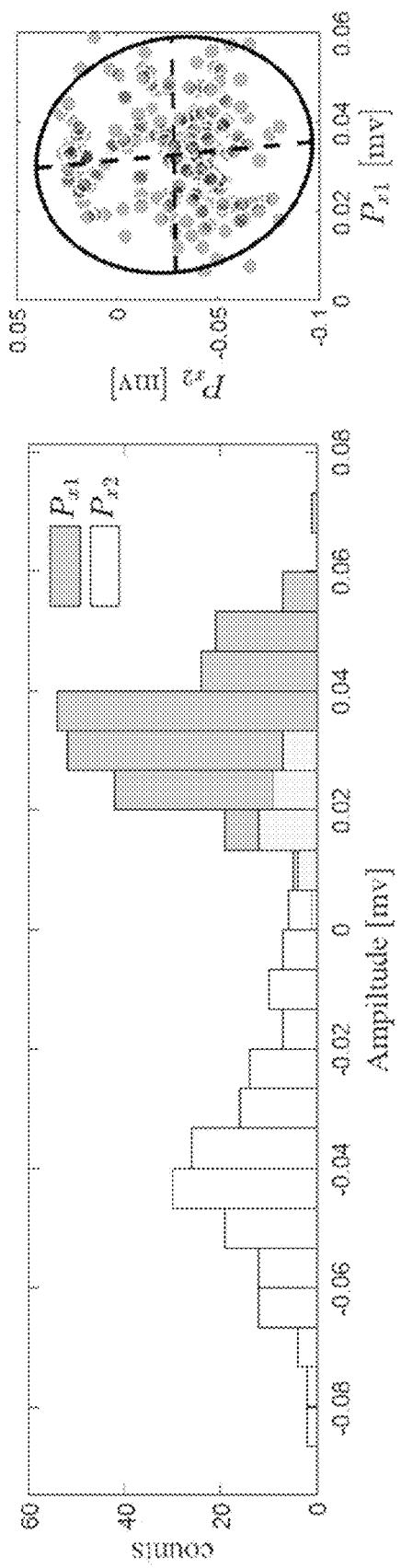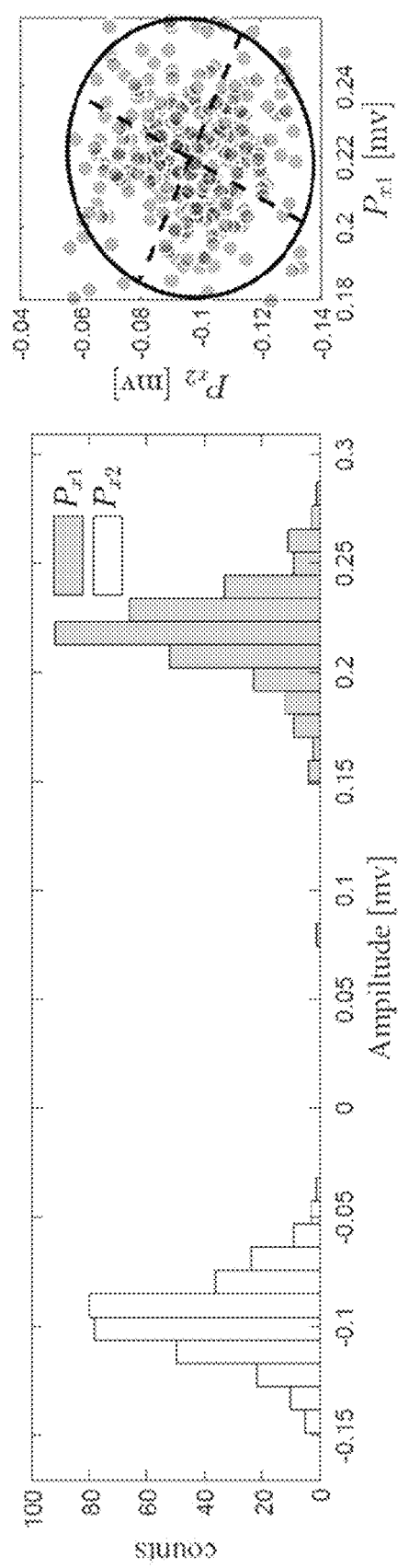
FIG. 5I  FIG. 5J  FIG. 5K  FIG. 5L

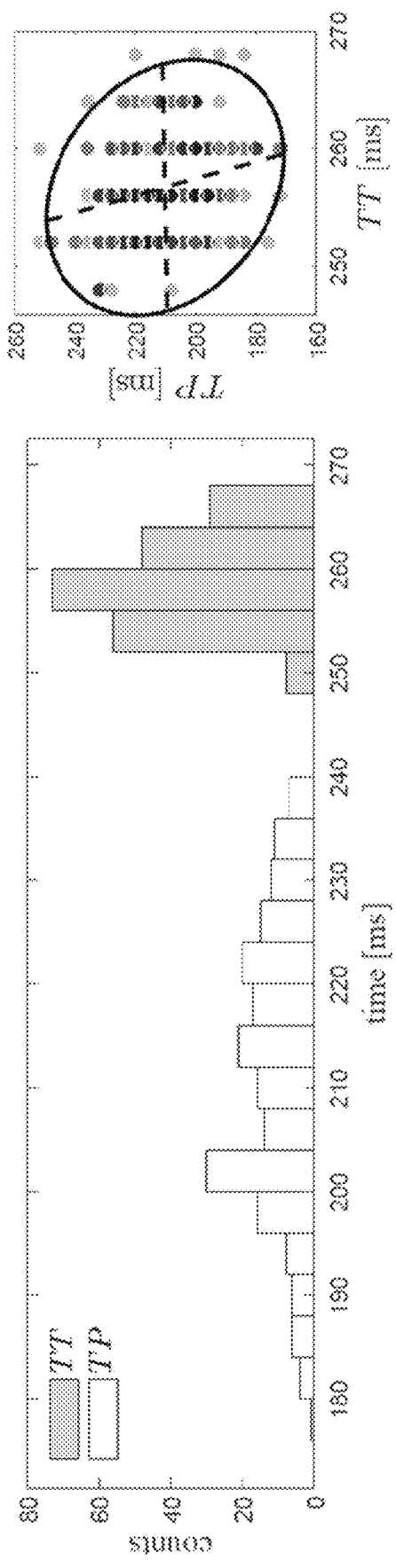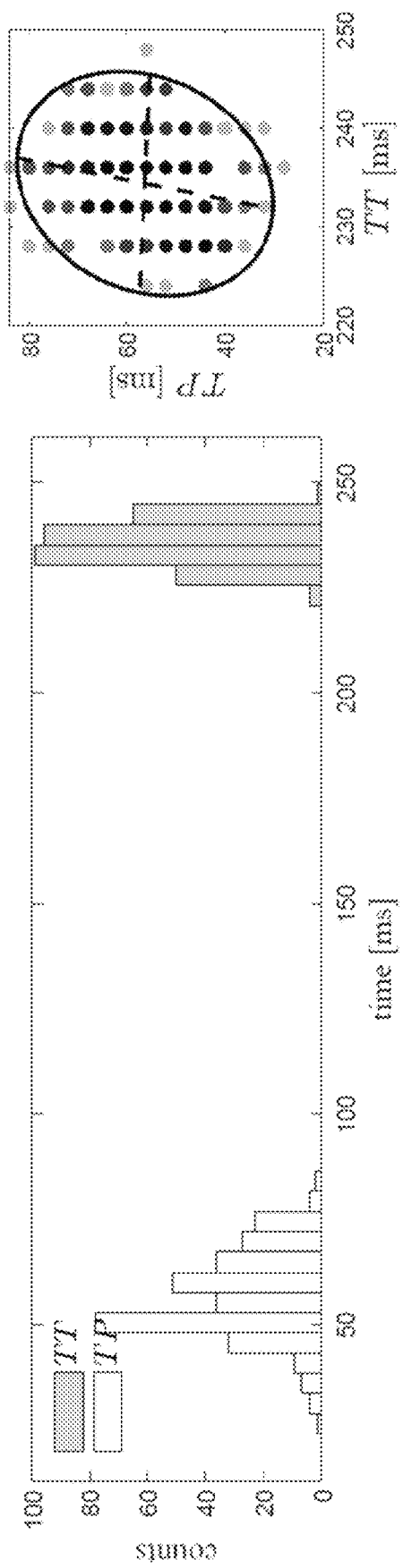

| FEATURE NAME | DISEASE STATE | GENDER | t-TEST p-VALUE | MUTUAL INFORMATION | ROC-AUC |
|---|---|---|---|---|---|
| dAlphaL | CAD | FEMALE | n/s | 1.043 | n/s |
| dAlphaU | CAD | BOTH GENDERS | n/s | 1.03 | n/s |
| dDmjL | CAD | FEMALE | 0.035 | 1.104 | 0.502 |
| | LVEDP | BOTH GENDERS | 0.031 | n/s | n/s |
| dDmjLUXR | CAD | BOTH GENDERS | n/s | n/s | 0.501 |
| dDmjU | LVEDP | BOTH GENDERS | 0.007 | n/s | n/s |
| dDmnLUXR | LVEDP | FEMALE | 0.02 | n/s | n/s |
| dDmnU | LVEDP | BOTH GENDERS | 0.038 | n/s | n/s |
| dKurtL | LVEDP | BOTH GENDERS | n/s | 1.171 | n/s |
| dMeanL | CAD | FEMALE | n/s | 1.012 | 0.516 |
| | LVEDP | MALE | 0.033 | n/s | n/s |
| dMeanLURP1 | LVEDP | BOTH GENDERS | 0.013 | n/s | n/s |
| dMeanLURP2 | LVEDP | MALE | 0.02 | n/s | n/s |
| dMeanU | CAD | FEMALE | n/s | 1.091 | n/s |
| | LVEDP | BOTH GENDERS | 0.003 | n/s | n/s |
| dModeLP | CAD | BOTH GENDERS | n/s | n/s | 0.507 |
| | LVEDP | BOTH GENDERS | 0.024 | n/s | n/s |
| dModeLURP1 | LVEDP | BOTH GENDERS | 0.013 | n/s | n/s |
| dModeLURP2 | LVEDP | MALE | 0.028 | n/s | n/s |

*FIG. 9*

| FEATURE NAME | DISEASE STATE | GENDER | t-TEST p-VALUE | MUTUAL INFORMATION | ROC-AUC |
|---|---|---|---|---|---|
| dModeUP | LVEDP | BOTH GENDERS | 0.004 | n/s | n/s |
| dPhiDiffXL1Med | CAD | BOTH GENDERS | 0.015 | n/s | n/s |
| dPhiDiffXL2Std | CAD | MALE | n/s | n/s | 0.502 |
| dPhiDiffXLMean | CAD | BOTH GENDERS | 0.026 | n/s | n/s |
| dPTT | LVEDP | FEMALE | 0.045 | n/s | n/s |
| dRelMeanMedDiffLURP1 | CAD | BOTH GENDERS | n/s | n/s | 0.5 |
| dSkewLURP1 | CAD | BOTH GENDERS | 0.034 | n/s | n/s |
| dStdLURP2 | CAD | BOTH GENDERS | n/s | 1.486 | 0.541 |
| dStdU | CAD | FEMALE | n/s | n/s | 0.511 |
| dXDmj | LVEDP | FEMALE | 0.012 | n/s | n/s |
| dXDmn | LVEDP | FEMALE | 0.003 | n/s | n/s |
| dXMean1 | CAD | FEMALE | 0.00064 | n/s | 0.548 |
| dXMean1 | CAD | FEMALE | 0.011 | n/s | 0.518 |
| dXStd1 | LVEDP | FEMALE | 0.037 | n/s | n/s |

*FIG. 9 (CONT.1)*

| FEATURE NAME | DISEASE STATE | GENDER | t-TEST p-VALUE | MUTUAL INFORMATION | ROC-AUC |
|---|---|---|---|---|---|
| dXStd2 | LVEDP | BOTH GENDERS | 0.042 | n/s | n/s |
| dYAlpha | CAD | BOTH GENDERS | 0.049 | n/s | n/s |
| dYKurt2 | CAD | MALE | n/s | 1.061 | n/s |
| dYMode2 | CAD | BOTH GENDERS | n/s | 1.104 | n/s |
| dYRelStdMAD2 | CAD | MALE | 0.042 | 1.048 | n/s |
| dYStd2 | CAD | MALE | n/s | 1.143 | n/s |
| dZAlpha | LVEDP | MALE | 0.039 | n/s | n/s |
| dZDmn | LVEDP | BOTH GENDERS | 0.037 | n/s | n/s |
| dZKurt2 | LVEDP | BOTH GENDERS | n/s | 1.076 | n/s |
| | CAD | FEMALE | n/s | 1.192 | n/s |
| dZMode2 | CAD | MALE | n/s | 1.036 | n/s |
| dZRelStdMAD1 | LVEDP | FEMALE | 0.041 | n/s | n/s |
| dZSkew1 | CAD | FEMALE | n/s | 1.094 | n/s |
| dZSkew2 | CAD | BOTH GENDERS | n/s | 1.058 | n/s |

*FIG. 9 (CONT.2)*

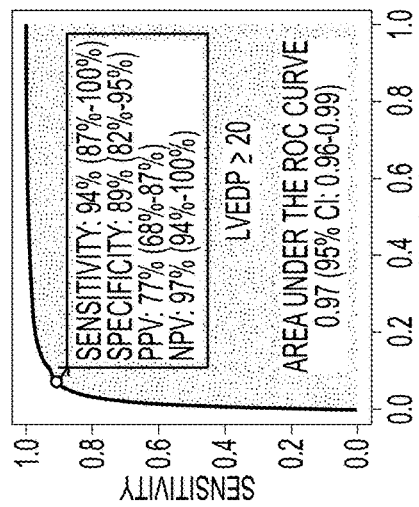
FIG. 11C
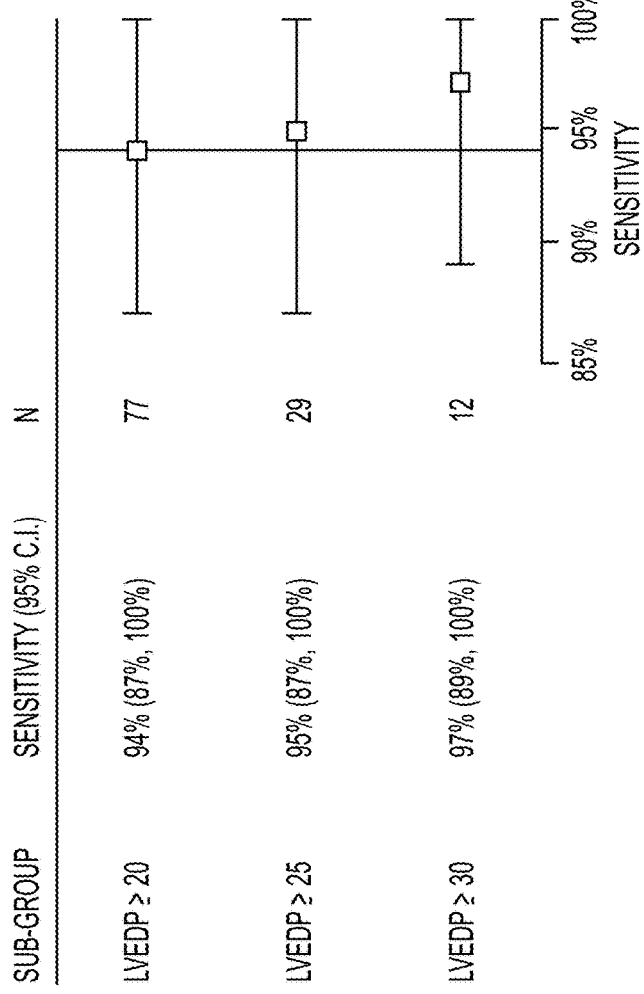
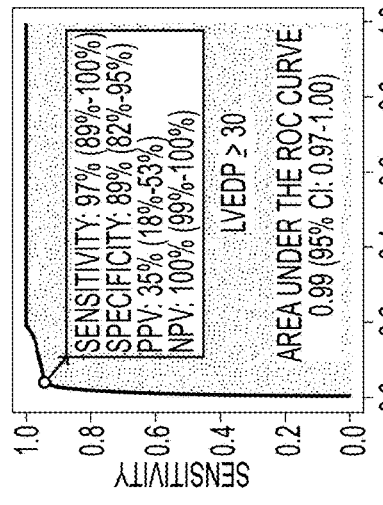
FIG. 11D
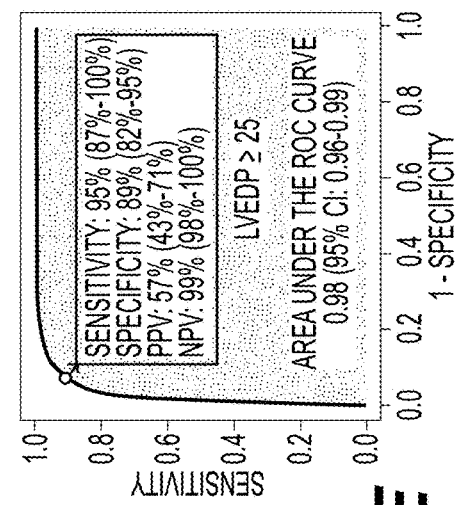
FIG. 11F
FIG. 11E

{{# METHOD AND SYSTEM TO ASSESS DISEASE USING DYNAMICAL ANALYSIS OF CARDIAC AND PHOTOPLETHYSMOGRAPHIC SIGNALS

CROSS REFERENCE TO RELATED APPLICATIONS

This utility patent application claims priority to, and the benefit of, U.S. Provisional Patent application No. 62/863,005, filed Jun. 18, 2019, entitled "Method and System to Assess Disease Using Dynamical Analysis of Cardiac and Photoplethysmographic Signals" and U.S. Provisional Patent application No. 62/862,991, filed Jun. 18, 2019, entitled "Method and System to Assess Disease Using Dynamical Analysis of Biophysical Signals," each of which is incorporated by reference herein in its entirety.

FIELD OF THE INVENTION

The present disclosure generally relates to non-invasive methods and systems for characterizing one or more physiological systems and their associated functions, activities, and abnormalities. More specifically, in an aspect, the present disclosure relates to non-invasive methods that utilize cardiac measurements and photoplethysmographic-related measurements, alone or in conjunction with other types of measurements of physiological phenomena and systems, to predict and/or detect the presence, non-presence, severity, and/or localization, of cardiovascular, pulmonary and cardiopulmonary disease, processes or conditions, among others.

BACKGROUND

The term "biophysical signal," as described in greater detail below, encompasses any physiological signal from which information may be obtained. Without wishing to be limiting, biophysical signals may be in part characterized by the form of energy such signals take (for example electrical, acoustic, chemical, thermal, magnetic, optical, etc.) by one or more physiological systems from which they may originate and/or be associated (e.g., circulatory/cardiovascular, nervous, respiratory, and the like), by associated organ systems, by tissue type, by cellular type, by cellular components such as organelles, etc., including combinations thereof. Biophysical signals may be acquired passively or actively, or both.

Often, biophysical signals are acquired in connection with or via invasive or minimally invasive techniques (e.g., via a catheterization) and/or the use of radiation (e.g., nuclear imaging), exercise/stress (e.g., treadmill or nuclear stress test) and/or the administration of pharmacological and/or other agents (e.g., vasodilators, contrast agents). These various modalities can modestly or even significantly increase the cost of acquiring such signals, as they may need to be administered in specialized settings, often via expensive equipment that often requires the patient travel to use, and even sometimes requiring an overnight stay in, e.g., a hospital or hotel. Some of these modalities can increase the risk to the patient for adverse effects such as, e.g., infection or an allergic reaction. Some expose the patient to doses of undesirable radiation. And in the case of, e.g., exercise or treadmill tests, they can trigger modest or even serious adverse events (e.g., myocardial infarction) that would otherwise not have happened. Moreover, these various modalities generally increase the amount of time required to ascertain the state of health, disease, or condition of the patient whose biophysical signals are being characterized, sometimes on the order of weeks or months—often for a patient who is or may be suffering from a modest or even serious health condition. This results in lost work productivity and higher overall healthcare costs for society. Such delays can also exact an emotional toll on the patient (which itself can be deleterious to the patient's health), their family, friends, and other caregivers tending to the needs of the patient.

As such, it is desirable to obtain information from biophysical signals that minimize or even eliminate the need to use invasive and/or minimally invasive techniques, radiation, exercise/stress and/or the use of pharmacological and/or other agents so that assessing (e.g., predict and/or detect) the presence, non-presence, severity and (in some cases) localization of various diseases, pathologies or conditions in mammalian or non-mammalian organisms may be accomplished more safely, with lower costs, and/or in a shorter amount of time than current methods and systems provide.

The methods and systems described herein address this need and may be used for a wide variety of clinical and even research needs in a wide variety of settings—from hospitals to emergency rooms, laboratories, battlefield or remote settings, at point of care with a patient's primary care physician or other caregivers, and even the home. Without being limiting, the following description provides example methods and systems for such use in the context of cardiac or cardiovascular-related disease states and conditions; most particularly pulmonary hypertension (PH) in its various forms, coronary artery disease (CAD) in its various forms, and heart failure in its various forms.

SUMMARY

The exemplified methods and systems facilitate one or more dynamical analyses that can characterize and identify synchronicity between acquired cardiac signals and photoplethysmographic signals to predict and/or estimate presence, non-presence, severity, and/or localization (where applicable) of abnormal cardiovascular conditions or disease, including, for example, but not limited to, coronary artery disease, abnormal left ventricular end-diastolic pressure disease (LVEDP), pulmonary hypertension and subcategories thereof, heart failure (HF), among others as discussed herein. In some embodiments, statistical properties of the synchronicity between one or more cardiac signals and one or more photoplethysmographic signals are evaluated. In some embodiments, statistical properties of a histogram of synchronicity between one or more cardiac signals and one or more photoplethysmographic signals are evaluated. In some embodiments, statistical and/or geometric properties of the Poincaré map of synchronicity between one or more cardiac signals and one or more photoplethysmographic signals are evaluated. The one or more cardiac signals and the one or more photoplethysmographic signals are concurrently acquired (interchangeably used herein with the term "simultaneously acquired") for the various evaluations of synchronicity as disclosed herein.

The terms "synchronicity" and "synchrony" refer to a physiological relationship between one or more signals of a first modality (e.g., cardiac signals) and a second modality (e.g., photoplethysmographic signals). For example, the cardiac electrical activity, as detected via electrodes or sensors of a measurement system, stimulates muscle to cause the left ventricle to eject oxygenated blood to the body. Some of this blood then travels to the fingertip, where its oxygenation level is detected via one or more photoplethysmographic sensors. The time lag between the maximal left ventricular electrical activity (e.g., corresponding to the R-peak in the cardiac signal) and the peak oxygenation in the fingertip may be defined as a "pulse transit time" (PTT), which is a temporal measurement. PTT can change from beat to beat (of the heart) because the physiological synchrony between the cardiac electrical activity (as measured using the cardiac biopotential signal) and the pulsatile oxygen perfusion (as measured using the PPG signal) can change. The Poincaré synchronization techniques and corresponding features disclosed herein characterize, among other things, that variation in synchrony.

The term "simultaneously acquired" refers to an acquired data point of a first modality (e.g., a channel of a cardiac signal) at time n having a corresponding data point at time n for a second modality (e.g., a channel of a photoplethysmographic signal), or even a third or more modalities. The timing, or temporal precision, of this multiple modality signal acquisition, is typically dictated by, e.g., the signal acquisition device circuitry, firmware, etc. For embodiments disclosed herein, a high degree of temporal precision (e.g., minimal temporal skew) between or among signals acquired from different modalities. In some embodiments, simultaneous signal/data point acquisition for different modalities is performed, e.g., via one or more circuits located in a single integrated hardware component or signal acquisition device, or even within a single printed circuit board or component therein. In other embodiments, simultaneous signal/data point acquisition for different modalities is performed via one or more circuits located on different signal acquisition devices having a common/shared clock, signal acquisition trigger, and/or other components. Moreover, various configurations of circuitry, other hardware, accessories (such as leads, electrodes, PPG sensors, etc.) within and among signal acquisition devices may accomplish this temporal precision.

A "cardiac signal" as used herein refers to one or more signals associated with the structure, function and/or activity of the cardiovascular system—including aspects of that signal's electrical/electrochemical conduction—that, e.g., cause contraction of the myocardium. A cardiac signal may include, in some embodiments, electrocardiographic signals such as, e.g., those acquired via an electrocardiogram (ECG) or other modalities.

A "photoplethysmographic signal(s)" as used herein refers to signal waveforms acquired from optical sensors that correspond to measured changes in light absorption by oxygenated and deoxygenated hemoglobin, such as light having wavelengths in the red and infrared spectrum. Photoplethysmographic signal(s), in some embodiments, include a raw signal(s) acquired via a pulse oximeter or a photoplethysmogram (PPG). In some embodiments, photoplethysmographic signal(s) are acquired from custom or dedicated equipment or circuitries (including off-the-shelf devices) that are configured to acquire such signal waveforms for the purpose of diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near infrared, blue and green may be used in different combinations, depending on the type and/or mode of PPG being employed.

A "biophysical signal" is not limited to a cardiac signal, a neurological signal, or a photoplethysmographic signal but encompasses any physiological signal from which information may be obtained. Not intending to be limited by example, one may classify biophysical signals into types or categories that can include, for example, electrical (e.g., certain cardiac and neurological system-related signals that can be observed, identified and/or quantified by techniques such as the measurement of voltage/potential, impedance, resistivity, conductivity, current, etc. in various domains such as time and/or frequency), magnetic, electromagnetic, optical (e.g. signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g. signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), an organ system (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements and their subatomic components. Unless stated otherwise, the term "biophysical signal acquisition" generally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light and other ways of actively interrogating the body tissue that does not involve ionizing energy or radiation (e.g., X-ray). Active biophysical signal acquisition may involve excitation-emission spectroscopy (including, e.g., excitation-emission fluorescence). Active biophysical signal acquisition may also involve transmitting ionizing energy or radiation (e.g., X-ray) (also referred to as "ionizing biophysical signal") to the body tissue. Passive and active biophysical signal acquisition means can be performed in conjunction with invasive procedures (e.g., via surgery or invasive radiologic intervention protocols) or non-invasively (e.g., via imaging).

The methods and systems described in the various embodiments herein are not so limited and may be utilized in any context of another physiological system or systems, organs, tissue, cells, etc. of a living body. By way of example only, two biophysical signal types that may be useful in the cardiovascular context include cardiac signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography.

In the context of the present disclosure, techniques for acquiring and analyzing biophysical signals are described in particular for use in diagnosing the presence, non-presence, localization (where applicable), and/or severity of certain disease states or conditions in, associated with, or affecting, the cardiovascular (or cardiac) system, including for example pulmonary hypertension, coronary artery disease, and heart failure (e.g., left-side or right-side heart failure).

Pulmonary hypertension, heart failure, and coronary artery disease are three diseases/conditions affiliated with the cardiovascular or cardiac system. Pulmonary hypertension (PH) generally refers to high blood pressure in the arteries of the lungs and can include a spectrum of conditions. PH typically has a complex and multifactorial etiology and an insidious clinical onset with varying severity. PH may progress to complications such as right heart failure and in many cases is fatal. The World Health Organization (WHO) has classified PH into five groups or types. The first PH group classified by the WHO is pulmonary arterial hypertension (PAH). PAH is a chronic and currently incurable disease that, among other things, causes the walls of the arteries of the lungs to tighten and stiffen. PAH requires at a minimum a heart catheterization for diagnosis. PAH is characterized by vasculopathy of the pulmonary arteries and defined, at cardiac catheterization, as a mean pulmonary artery pressure of 25 mm Hg or more. One form of pulmonary arterial hypertension is known as idiopathic pulmonary arterial hypertension—PAH—that occurs without a clear cause. Among others, subcategories of PAH include heritable PAH, drug and toxin induced PAH, and PAH associated with other systemic diseases such as, e.g., connective tissue disease, HIV infection, portal hypertension, and congenital heart disease. PAH includes all causes that lead to the structural narrowing of the pulmonary vessels. With PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. The second PH group as classified by the WHO is pulmonary hypertension due to left heart disease. This group of disorders is generally characterized by problems with the left side of the heart. Such problems can, over time, lead to changes within the pulmonary arteries. Specific subgroups include left ventricular systolic dysfunction, left ventricular diastolic dysfunction, valvular disease and, finally, congenital cardiomyopathies and obstructions not due to valvular disease. Treatments of this second PH group tend to focus on the underlying problems (e.g., surgery to replace a heart valve, various medications, etc.). The third PH group as classified by the WHO is large and diverse, generally relating to lung disease or hypoxia. Subgroups include chronic obstructive pulmonary disease, interstitial lung disease, sleep breathing disorders, alveolar hypoventilation disorders, chronic high-altitude exposure, and developmental lung disease. The fourth PH group is classified by the WHO as chronic thromboembolic pulmonary hypertension, caused when blood clots enter or form within the lungs, blocking the flow of blood through the pulmonary arteries. The fifth PH group is classified by the WHO as including rare disorders that lead to PH, such as hematologic disorders, systemic disorders such as sarcoidosis that have lung involvement, metabolic disorders, and a subgroup of other diseases. The mechanisms of PH in this fifth group are poorly understood.

PH in all of its forms can be difficult to diagnose in a routine medical examination because the most common symptoms of PH (shortness of breath, fatigue, chest pain, edema, heart palpitations, dizziness) are associated with so many other conditions. Blood tests, chest x-rays, electro- and echocardiograms, pulmonary function tests, exercise tolerance tests, and nuclear scans are all used variously to help a physician to diagnose PH in its specific form. As noted above, the "gold standard" for diagnosing PH, and for PAH, in particular, is a cardiac catheterization of the right side of the heart by directly measuring the pressure in the pulmonary arteries. If PAH is suspected in a subject, one of several investigations may be performed to confirm the condition, such as electrocardiography, chest radiography, and pulmonary function tests, among others. Evidence of right heart strain on electrocardiography and prominent pulmonary arteries or cardiomegaly on chest radiography is typically seen. However, a normal electrocardiograph and chest radiograph cannot necessarily exclude a diagnosis of PAH. Further tests may be needed to confirm the diagnosis and to establish cause and severity. For example, blood tests, exercise tests, and overnight oximetry tests may be performed. Yet further, imaging testing may also be performed. Imaging testing examples include isotope perfusion lung scanning, high resolution computed tomography, computed tomography, pulmonary angiography, and magnetic resonance pulmonary angiography. If these (and possibly other) non-invasive investigations support a diagnosis of PAH, right heart catheterization typically is needed to confirm the diagnosis by directly measuring pulmonary pressure. It also allows measurement of cardiac output and estimation of left atrial pressure using pulmonary arterial wedge pressure. While non-invasive techniques exist to determine whether PAH may exist in a subject, these techniques cannot reliably confirm a diagnosis of PAH unless an invasive right heart catheterization is performed. Aspects and embodiments of methods and systems for assessing PH are disclosed in commonly-owned U.S. patent application Ser. No. 16/429,593, the entirety of which is hereby incorporated by reference.

Heart failure affects almost 6 million people in the United States alone, and more than 870,000 people are diagnosed with heart failure each year. The term "heart failure" (sometimes referred to as congestive heart failure or CHF) generally refers to a chronic, progressive condition or process in which the heart muscle is unable to pump enough blood to meet the needs of the body, either because the heart muscle is weakened or stiff or because a defect is present that prevents proper circulation. This results in, e.g., blood and fluid backup into the lungs, edema, fatigue, dizziness, fainting, rapid and/or irregular heartbeat, dry cough, nausea and shortness of breath. Common causes of heart failure are coronary artery disease (CAD), high blood pressure, cardiomyopathy, arrhythmia, kidney disease, heart defects, obesity, tobacco use and diabetes. Diastolic heart failure (DHF), left- or left-sided heart failure/disease (also referred to as left ventricular heart failure), right- or right-sided heart failure/disease (also referred to as right ventricular heart failure) and systolic heart failure (SHF) are common types of heart failure.

Left-sided heart failure is further classified into two main types: systolic failure (or heart failure with reduced ejection fraction or reduced left ventricular function) and diastolic failure/dysfunction (or heart failure with preserved ejection fraction or preserved left ventricular function). Procedures and technologies commonly used to determine if a patient has left-sided heart failure include cardiac catheterization, x-ray, echocardiogram, electrocardiogram (EKG), electrophysiology study, radionucleotide imaging, and various treadmill tests, including a test that measures peak $VO_2$. Ejection fraction (EF), which is a measurement expressed as a percentage of how much blood a ventricle pumps out with each contraction (and in the case of left-sided heart failure, the left ventricle), is most often obtained non-invasively via an echocardiogram. A normal left ventricular ejection fraction (LVEF) ranges from about 55% to about 70%.

When systolic failure occurs, the left ventricle cannot contract forcefully enough to keep blood circulating normally throughout the body, which deprives the body of a normal supply of blood. As the left ventricle pumps harder to compensate, it grows weaker and thinner. As a result, blood flows backward into organs, causing fluid buildup in the lungs and/or swelling in other parts of the body. Echocardiograms, magnetic resonance imaging, and nuclear medicine scans (e.g., multiple gated acquisition) are techniques used to noninvasively measure ejection fraction (EF), expressed as a percentage of the volume of blood pumped by the left ventricle relative to its filling volume to aid in the diagnosis of systolic failure. In particular, left ventricular ejection fraction (LVEF) values below 55% indicate the pumping ability of the heart is below normal, and can in severe cases, be measured at less than about 35%. In general, a diagnosis of systolic failure can be made or aided when these LVEF values are below normal.

When diastolic heart failure occurs, the left ventricle has grown stiff or thick, losing its ability to relax normally, which in turn means that the lower left chamber of the heart is unable to properly fill with blood. This reduces the amount of blood pumped out to the body. Over time, this causes blood to build up inside the left atrium, and then in the lungs, leading to fluid congestion and symptoms of heart failure. In this case, LVEF values tend to be preserved within the normal range. As such, other tests, such as an invasive catheterization, may be used to measure the left ventricular end diastolic pressure (LVEDP) to aid in the diagnosis of diastolic heart failure as well as other forms of heart failure with preserved EF. Typically, LVEDP is measured either directly by the placement of a catheter in the left ventricle or indirectly by placing a catheter in the pulmonary artery to measure the pulmonary capillary wedge pressure. Such catheterization techniques, by their nature, increase the risk of infection and other complications to the patient and tend to be costly. As such, non-invasive methods and systems for determining or estimating LVEDP in diagnosing the presence or non-presence and/or severity of diastolic heart failure as well as myriad other forms of heart failure with preserved EF are desirable. In addition, non-invasive methods and systems for diagnosing the presence or non-presence and/or severity of diastolic heart failure as well as myriad other forms of heart failure with preserved EF, without necessarily including a determination or estimate of an abnormal LVEDP, are desirable. Embodiments of the present disclosure address all of these needs.

Right-sided heart failure often occurs due to left-sided heart failure, when the weakened and/or stiff left ventricle loses power to efficiently pump blood to the rest of the body. As a result, fluid is forced back through the lungs, weakening the heart's right side, causing right-sided heart failure. This backward flow backs up in the veins, causing fluid to swell in the legs, ankles, GI tract and liver. In other cases, certain lung diseases such as chronic obstructive pulmonary disease and pulmonary fibrosis can cause right-sided heart failure, despite the left side of the heart functioning normally. Procedures and technologies commonly used to determine if a patient has left-sided heart failure include a blood test, cardiac CT scan, cardiac catheterization, x-ray, coronary angiography, echocardiogram, electrocardiogram (EKG), myocardial biopsy, pulmonary function studies, and various forms of stress tests such as a treadmill test.

Pulmonary hypertension is closely associated with heart failure. As noted above, PAH (the first WHO PH group) can lead to an increased right ventricular afterload, right heart failure, and premature death. PH due to left heart failure (the second WHO PH group) is believed to be the most common cause of PH.

Ischemic heart disease, also known as cardiac ischemia or myocardial ischemia, and related conditions or pathologies may also be estimated or diagnosed with the techniques disclosed herein. Ischemic heart disease is a disease or group of diseases characterized by a reduced blood supply to the heart muscle, usually due to coronary artery disease (CAD). CAD is closely related to heart failure and is its most common cause. CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmia. An arrhythmia is an abnormal heart rhythm and can include any change from the normal sequence of electrical conduction of the heart and, in some cases, can lead to cardiac arrest. The evaluation of PH, heart failure, CAD, and other diseases and/or conditions can be complex, and many invasive techniques and tools are used to assess the presence and severity of the conditions as noted above. In addition, the commonalities among symptoms of these diseases and/or conditions as well as the fundamental connection between the respiratory and cardiovascular systems—due to the fact that they work together to oxygenate the cells and tissues of the body—point to a complex physiological interrelatedness that may be exploited to improve the detection and ultimate treatment of such diseases and/or conditions. Conventional methodologies to assess these biophysical signals in this context still pose significant challenges in giving healthcare providers tools for accurately detecting/diagnosing the presence or non-presence of such diseases and conditions.

For example, in electrocardiography—a field of cardiology in which the heart's electrical activity is analyzed to obtain information about its structure and function—it has been observed that significant ischemic heart disease can alter ventricular conduction properties of the myocardium in the perfusion bed downstream of a coronary artery narrowing or occlusion, the pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

As discussed above, the exemplified methods and systems facilitate one or more dynamical analyses that can characterize and identify synchronicity between acquired cardiac signals and photoplethysmographic signals to predict and/or estimate presence, non-presence, severity, and/or localization of abnormal cardiovascular conditions or disease, including, for example, but not limited to, coronary artery disease, abnormal left ventricular end-diastolic pressure disease (LVEDP), pulmonary hypertension and subcategories thereof, heart failure (HF), among others as discussed herein. In some embodiments, the dynamical features include statistical or dynamical analysis of phase relations between an acquired set of one or more cardiac signal(s) and an acquired set of one or more photoplethysmographic signal(s). In some embodiments, the dynamical features include statistical or dynamical analysis of variance between landmarks between the acquired set of one or more cardiac signal(s) and the acquired set of one or more photoplethysmographic signal(s). In some embodiments, the dynamical features include statistical or dynamical analysis of variance in landmarks determined in the acquired set of one or more photoplethysmographic signal(s) in which the landmarks are defined by the cardiac signals.

In an aspect, a method is disclosed for non-invasively assessing a disease state or abnormal condition of a subject, the method comprising obtaining, by one or more processors (e.g., from a stored database or from a measurement system), a first biophysical signal data set of a subject associated with saturation of oxygenated or deoxygenated hemoglobin, including a red photoplethysmographic signal and an infrared photoplethysmographic signal; obtaining, by the one or more processors (e.g., from a stored database or from a measurement system), a second biophysical signal data set of the subject associated with a cardiac signal (e.g., acquired from a phase space recorder or from an ECG device); determining, by the one or more processors, one or more synchronicity dynamical properties between the first biophysical signal data set associated with the saturation of oxygenated and/or deoxygenated hemoglobin and the second biophysical signal data set associated with the cardiac signal; and determining, by the one or more processors, an estimated value for presence, non-presence, severity, and/or localization (where applicable) of a disease state based on the determined one or more synchronicity dynamical properties, wherein the disease state includes presence, non-presence, severity, and/or localization (where applicable) of coronary artery disease (e.g., significant coronary artery disease) or abnormal left ventricular end-diastolic pressure.

In some embodiments, the presence, non-presence, and/or severity of a disease or condition can be assessed based on an assessment of left ventricular end-diastolic pressure (LVEDP), including an abnormal LVEDP.

In some embodiments, the disease state or condition includes significant coronary artery disease.

In some embodiments, the disease state or condition includes pulmonary hypertension.

In some embodiments, the disease state or condition includes pulmonary arterial hypertension (PAH).

In some embodiments, the disease state or condition includes pulmonary hypertension due to left heart disease.

In some embodiments, the disease state or condition includes rare disorders that lead to pulmonary hypertension.

In some embodiments, the disease state or condition includes left ventricular heart failure or left-sided heart failure.

In some embodiments, the disease state or condition includes right ventricular heart failure or right-sided heart failure.

In some embodiments, the disease state or condition includes systolic heart failure (SHF).

In some embodiments, the disease state or condition includes diastolic heart failure.

In some embodiments, the disease state or condition includes ischemic heart disease.

In some embodiments, the disease state or condition includes arrhythmia.

In some embodiments, the method further includes determining, by the one or more processors, one or more second estimated values for the presence, non-presence, localization, and/or severity of two or more of the diseases or conditions.

In some embodiments, the synchronicity dynamical property (e.g., example PM #1) of the first and second biophysical signal data sets comprises a statistical assessment of values of the cardiac signal at a landmark defined by both the red photoplethysmographic signal and the infrared photoplethysmographic signal.

In some embodiments, the landmark defined by both the red photoplethysmographic signal and the infrared photoplethysmographic signal is defined at a time where the values of the red photoplethysmographic signal and the infrared photoplethysmographic signal intersects.

In some embodiments, the synchronicity dynamical property (e.g., per example #2) of the first and second biophysical signal data sets comprises a statistical assessment of values of one of the red photoplethysmographic signal or the infrared photoplethysmographic signal at a landmark defined in the cardiac signal.

In some embodiments, the landmark defined in the cardiac signal includes an associated peak associated with ventricular depolarization.

In some embodiments, the landmark defined in the cardiac signal includes an associated peak associated with ventricular repolarization or atrial depolarization.

In some embodiments, the synchronicity dynamical property (e.g., example #3) of the first and second biophysical signal data sets comprises a statistical assessment of time intervals between i) a first set of landmarks defined between the red photoplethysmographic signal and the infrared photoplethysmographic signal and ii) a second set of landmarks defined in the cardiac signal.

In some embodiments, the second set of landmarks defined in the cardiac signal includes associated peaks in the cardiac signal associated with ventricular depolarization.

In some embodiments, the second set of landmarks defined in the cardiac signal includes associated peaks in the cardiac signal associated with ventricular repolarization or atrial depolarization.

In some embodiments, the first set of landmarks defined by both the red photoplethysmographic signal and the infrared photoplethysmographic signal are defined at times where the values of the red photoplethysmographic signal and the infrared photoplethysmographic signal intersect.

In some embodiments, the synchronicity dynamical property (e.g., example #4) of the first and second biophysical signal data sets comprises a statistical assessment of phase relations between periods of one of the red or infrared photoplethysmographic signals and periods of the cardiac signal.

In some embodiments, the method further includes causing, by the one or more processors, generation of a visualization of the estimated value for the presence, non-presence, severity, and/or localization (where applicable) of the disease state, wherein the generated visualization is rendered and displayed at a display of a computing device (e.g., computing workstation; a surgical, diagnostic, or instrumentation equipment) and/or presented in a report (e.g., an electronic report).

In some embodiments, the method further includes determining, by the one or more processors, a histogram of the synchronicity of the first and second biophysical signal data sets; and extracting a first statistical parameter of the histogram, wherein the first statistical parameter of the histogram is selected from the group consisting of mean, mode, median, skew, kurtosis, wherein the extracted first statistical parameter is used in the determining of the estimated value for the presence, non-presence, severity, and/or localization (where applicable) of the disease state.

In some embodiments, the method further includes determining, by the one or more processors, a Poincaré map of the synchronicity of the first and second biophysical signal data sets; and extracting a second statistical parameter of the Poincaré map, wherein the second statistical parameter of the histogram is selected from the group consisting of mean, mode, median, skew, kurtosis, wherein the extracted second statistical parameter is used in the determining of the estimated value for the presence, non-presence, severity, and/or localization (where applicable) of the disease state.

In some embodiments, the method further includes determining, by the one or more processors, a Poincaré map of the synchronicity of the first and second biophysical signal data sets; and extracting a geometric property of an eclipse fitted to a cluster in the Poincaré map (e.g., major/minor diameter of ellipse, angle of the ellipse), wherein the extracted geometric property of the eclipse is used in the determining of the estimated value for the presence, non-presence, severity, and/or localization (where applicable) of the disease state.

In some embodiments, the Poincaré map is generated by iteratively plotting in an x-axis a parameter associated with the synchronicity of the first and second biophysical signal data sets at index x and index x+1 and in a y-axis the parameter at index x and index x−1.

In some embodiments, the parameter is a time interval between a landmark of a cardiac signal (e.g., R-peaks) and a crossover between the red and infrared photo-photoplethysmographic signals.

In some embodiments, the parameter is an amplitude signal value of a cardiac signal at a crossover landmark defined between the red and infrared photo-photoplethysmographic signals.

In some embodiments, the parameter is an amplitude signal value of a photo-photoplethysmographic signal at a landmark defined in the cardiac signal.

In another aspect, a system is disclosed (e.g., for non-invasively assessing a disease state or abnormal condition of a subject), the system comprising a processor; and a memory having instructions stored thereon, wherein execution of the instructions by the processor cause the processor to obtain (e.g., from a stored database or from a measurement system), a first biophysical signal data set of a subject associated with saturation of oxygenated or deoxygenated hemoglobin, including a red photoplethysmographic signal and an infrared photoplethysmographic signal; obtain (e.g., from a stored database or from a measurement system), a second biophysical signal data set of the subject associated with a cardiac signal (e.g., acquired from a phase space recorder or from an ECG device); determine one or more synchronicity dynamical properties between the first biophysical signal data set associated with the saturation of oxygenated and/or deoxygenated hemoglobin and the second biophysical signal data set associated with the cardiac signal; and determine an estimated value for the presence of a disease state based on the determined one or more synchronicity dynamical properties (e.g., wherein the disease state includes the presence of coronary artery disease (e.g., significant coronary artery disease) or a disease or condition associated with abnormal left ventricular end-diastolic pressure).

In some embodiments, the synchronicity dynamical property (e.g., example PM #1) of the first and second biophysical signal data sets comprises a statistical assessment of values of the cardiac signal at a landmark defined by both the red photoplethysmographic signal and the infrared photoplethysmographic signal.

In some embodiments, the landmark defined by both the red photoplethysmographic signal and the infrared photoplethysmographic signal is defined at a time where the values of the red photoplethysmographic signal and the infrared photoplethysmographic signal intersects.

In some embodiments, the synchronicity dynamical property (e.g., per example #2) of the first and second biophysical signal data sets comprises a statistical assessment of values of one of the red photoplethysmographic signal or the infrared photoplethysmographic signal at a landmark defined in the cardiac signal.

In some embodiments, the landmark defined in the cardiac signal includes an associated peak associated with ventricular depolarization.

In some embodiments, the landmark defined in the cardiac signal includes an associated peak associated with ventricular repolarization or atrial depolarization.

In some embodiments, the synchronicity dynamical property (e.g., example #3) of the first and second biophysical signal data sets comprises a statistical assessment of time intervals between i) a first set of landmarks defined between the red photoplethysmographic signal and the infrared photoplethysmographic signal and ii) a second set of landmarks defined in the cardiac signal.

In some embodiments, the second set of landmarks defined in the cardiac signal includes associated peaks in the cardiac signal associated with ventricular depolarization.

In some embodiments, the second set of landmarks defined in the cardiac signal includes associated peaks in the cardiac signal associated with ventricular repolarization or atrial depolarization.

In some embodiments, the first set of landmarks defined by both the red photoplethysmographic signal and the infrared photoplethysmographic signal are defined at times where the values of the red photoplethysmographic signal and the infrared photoplethysmographic signal intersect.

In some embodiments, the synchronicity dynamical property (e.g., example #4) of the first and second biophysical signal data sets comprises a statistical assessment of phase relations between periods of one of the red or infrared photoplethysmographic signals and periods of the cardiac signal.

In some embodiments, execution of the instructions by the processor further causes the processor to cause generation of a visualization of the estimated value for the presence of the disease state, wherein the generated visualization is rendered and displayed at a display of a computing device (e.g., computing workstation; a surgical, diagnostic, or instrumentation equipment) and/or presented in a report (e.g., an electronic report).

In some embodiments, execution of the instructions by the processor further causes the processor to determine a histogram of the synchronicity of the first and second biophysical signal data sets; and extracting a first statistical parameter of the histogram, wherein the first statistical parameter of the histogram is selected from the group consisting of mean, mode, median, skew, kurtosis, wherein the extracted first statistical parameter is used in the determining of the estimated value for the presence of the disease state.

In some embodiments, execution of the instructions by the processor further causes the processor to determine a Poincaré map of the synchronicity of the first and second biophysical signal data sets; and extract a second statistical parameter of the Poincaré map, wherein the second statistical parameter of the histogram is selected from the group consisting of mean, mode, median, skew, kurtosis, wherein the extracted second statistical parameter is used in the determining of the estimated value for the presence of the disease state.

In some embodiments, execution of the instructions by the processor further causes the processor to determine a Poincaré map of the synchronicity of the first and second biophysical signal data sets; and extract a geometric property of an eclipse fitted to a cluster in the Poincaré map (e.g., major/minor diameter of ellipse, angle of the ellipse), wherein the extracted geometric property of the eclipse is used in the determining of the estimated value for the presence of the disease state.

In some embodiments, the Poincaré map is generated by iteratively plotting in an x-axis a parameter associated with the synchronicity of the first and second biophysical signal data sets at index x and index x+1 and in a y-axis the parameter at index x and index x−1.

In some embodiments, the parameter is a time interval between a landmark of a cardiac signal (e.g., R-peaks) and a crossover between the red and infrared photo-photoplethysmographic signals.

In some embodiments, the parameter is an amplitude signal value of a cardiac signal at a crossover landmark defined between the red and infrared photo-photoplethysmographic signals.

In some embodiments, the parameter is an amplitude signal value of a photo-photoplethysmographic signal at a landmark defined in the cardiac signal.

In some embodiments, the system further includes a measurement system configured to acquire one or more photoplethysmographic signals.

In some embodiments, the system further includes a measurement system configured to acquire one or more cardiac signals.

In some embodiments, the system further includes a first measurement system configured to acquire one or more photoplethysmographic signals and a second measurement system configured to acquire one or more cardiac signals.

In another aspect, a system is disclosed comprising a processor; and a memory having instructions stored therein, wherein execution of the instructions by the processor causes the processor to perform any of the above-discussed methods.

In another aspect, a computer readable medium is disclosed having instructions stored therein, wherein execution of the instructions by a processor causes the processor to perform any of the above-discussed methods.

BRIEF DESCRIPTION OF THE DRAWINGS

The accompanying drawings, which are incorporated in and constitute a part of this specification, illustrate embodiments and together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 5D shows examples fitted ellipse features that can be extracted from the Poincaré map of FIG. 5C in accordance with an illustrative embodiment.

FIG. 5E shows an example Poincaré map of a data set acquired from a CAD-negative patient (i.e., a patient who does not have CAD).

FIG. 5F shows an example Poincaré map of a data set acquired from a CAD-positive patient (i.e., a patient who has CAD in some form).

FIGS. 5I, 5J, 5K, and 5L illustrate another example of dynamical properties of synchronicity between an acquired photoplethysmographic signal and cardiac signals in accordance with an illustrative embodiment.

FIGS. 7F, 7G, 7H, and 7I illustrate other example dynamical properties of synchronicity between acquired photoplethysmographic signal and cardiac signals in accordance with an illustrative embodiment.

FIG. 9 shows experimental results from a study that indicates a clinical predictive value of certain dynamical features extracted from Poincaré and phase analyses of photoplethysmographic and cardiac signals that indicate the presence and non-presence of a disease or abnormal condition, or an indicator of one, in accordance with an illustrative embodiment.

FIGS. 11A-11F show experimental results for a trained classifier to predict an elevated LVEDP in accordance with an illustrative embodiment.

DETAILED SPECIFICATION

Figure 1:
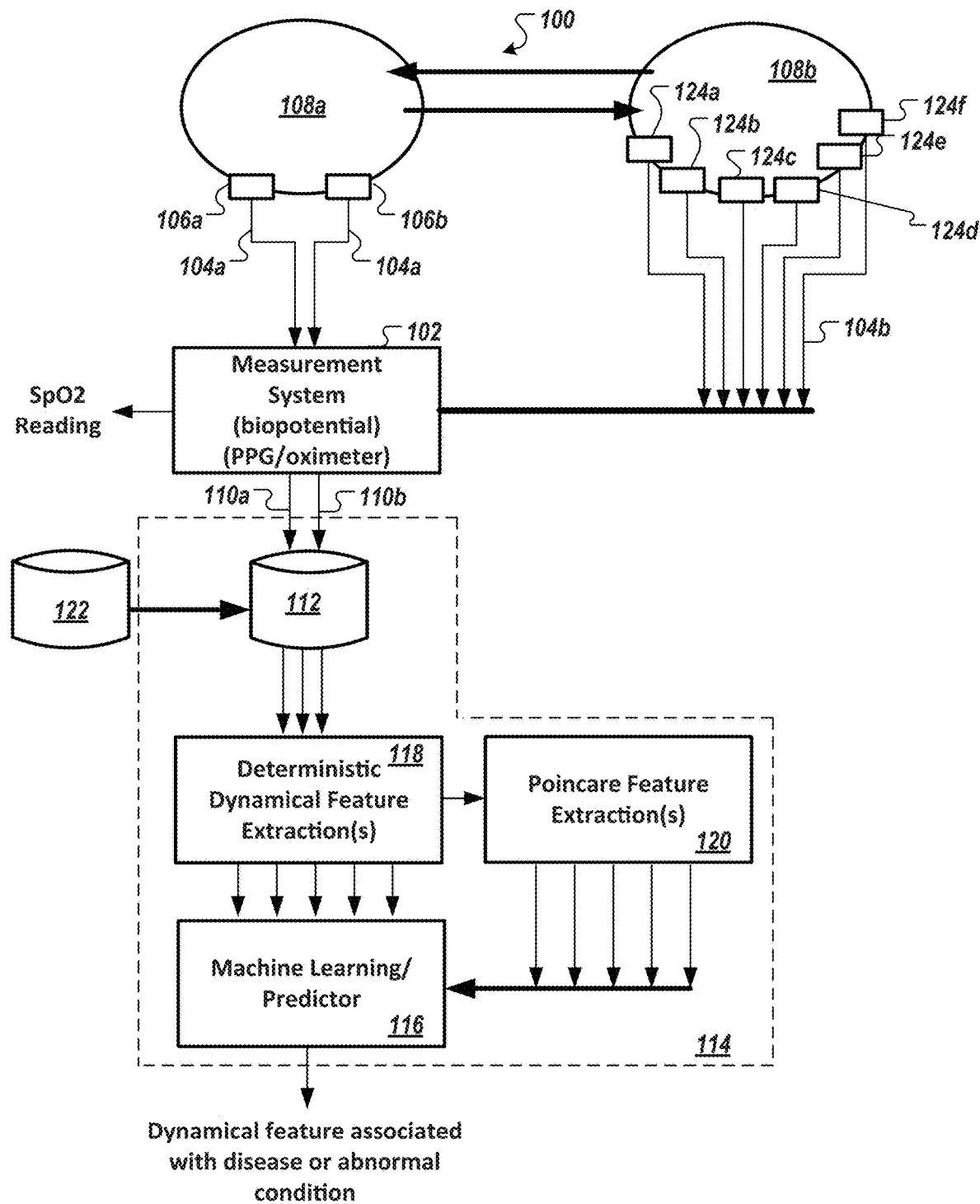
FIG. 1 is a diagram of an example system configured to non-invasively assess dynamical properties of a physiological system to predict and/or estimate the presence, non-presence, severity, and/or localization (where applicable) of disease or condition, or an indicator of one, in such physiological system, in accordance with an illustrative embodiment.

Each and every feature described herein, and each and every combination of two or more of such features, is included within the scope of the present invention provided that the features included in such a combination are not mutually inconsistent.

While the present disclosure is directed to the beneficial assessment of biophysical signals, e.g., raw or pre-processed photoplethysmographic signals, cardiac signals, etc., in the diagnosis and treatment of cardiac-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. In the cardiac (or cardiovascular) context, the assessment can be applied to the diagnosis and treatment of coronary artery disease (CAD) and diseases and/or conditions associated with an abnormal left ventricular end-diastolic pressure (LVEDP). The assessment can be applied for the diagnosis and treatment of any number of therapies, alone or in combination, such as the placement of a stent in a coronary artery, the performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases such as blood or other disorders), as well as other cardiac-related pathologies, conditions and/or diseases. In some embodiments, the assessment may be applied to neurological-related pathologies and conditions. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the nth reference in the list. For example, [36] refers to the 36th reference in the list, namely F. Pedregosa, G. Varoquaux, A. Gramfort, V. Michel, B. Thirion, O. Grisel, M. Blondel, P. Prettenhofer, R. Weiss, V. Dubourg, et al., "Scikit-learn: Machine learning in python," Journal of machine learning research 12, 2825-2830 (October 2011). All references cited and discussed in this specification are incorporated herein by reference in their entireties and to the same extent as if each reference was individually incorporated by reference.

Example System

FIG. 1 is a diagram of an example system 100 configured to non-invasively assess dynamical properties of a physiological system to predict and/or estimate (e.g., determine) the presence, non-presence, localization, and/or severity of a disease or condition, or an indicator of one, in such physiological system, in accordance with an illustrative embodiment. Indeed, as used herein, the term "predicting" refers to forecasting a future event (e.g., potential development of a disease or condition), while the term "estimating" can refer to a quantification of some metric based on available information, e.g., for the presence, non-presence, localization, and/or severity of a disease or condition, or an indicator of one. The operations of predicting and estimating can be generally referred to as determining.

As noted herein, "physiological systems" can refer to the cardiovascular system, the pulmonary system, the renal system, the nervous system, and other functional systems and sub-systems of the body. In the context of the cardiovascular system, system 100 facilitates the investigation of complex, nonlinear dynamical properties of the heart over many heart cycles.

In FIG. 1, non-invasive measurement system 102 (shown as "Measurement System" 102) acquires two or more sets of biophysical signals 104 (shown as sets 104a and 104b) via measurement probes 106 (shown as probes 106a, 106b and probes 124a-124f) from a subject 108 (shown at location 108a and 108b) to produce a biophysical-signal data set 110, including a first type and a second type (shown as 110a and 110b).

The first type is acquired via probes 106a, 106b from the subject at location 108a (e.g., a finger of the subject) to generate a raw photoplethysmographic signal data set 110a from photoplethysmographic signal(s) 104a. In some embodiments, the raw photoplethysmographic signal data set 110a includes one or more photoplethysmographic signal(s) associated with measured changes in light absorption of oxygenated and/or deoxygenated hemoglobin.

The second type is acquired via probes 124a-124f from subject 108 to generate a cardiac signal data set 110b from cardiac signals 104b. In some embodiments, cardiac signal data set 110b includes data associated with biopotential signals acquired across a plurality of channels. In some embodiments, cardiac signal data set 110b includes wideband biopotential signals, e.g., acquired via a phase-space recorder, as described in U.S. Patent Publication No. 2017/0119272, entitled "Method and Apparatus for Wide-Band Phase Gradient Signal Acquisition," which is incorporated by reference herein in its entirety. In some embodiments, the cardiac signal data set includes bipolar wide-band biopotential signals, e.g., acquired via a phase-space recorder, as described in U.S. Patent Publication No. 2018/0249960, entitled "Method and Apparatus for Wide-Band Phase Gradient Signal Acquisition," which is incorporated by reference herein in its entirety. In other embodiments, the cardiac signal data set 110b includes one or more biopotential signals acquired from conventional electrocardiogram (ECG/EKG) equipment (e.g., Holter device, 12 lead ECG, etc.).

Example Photoplethysmographic Signals

Figure 2A:
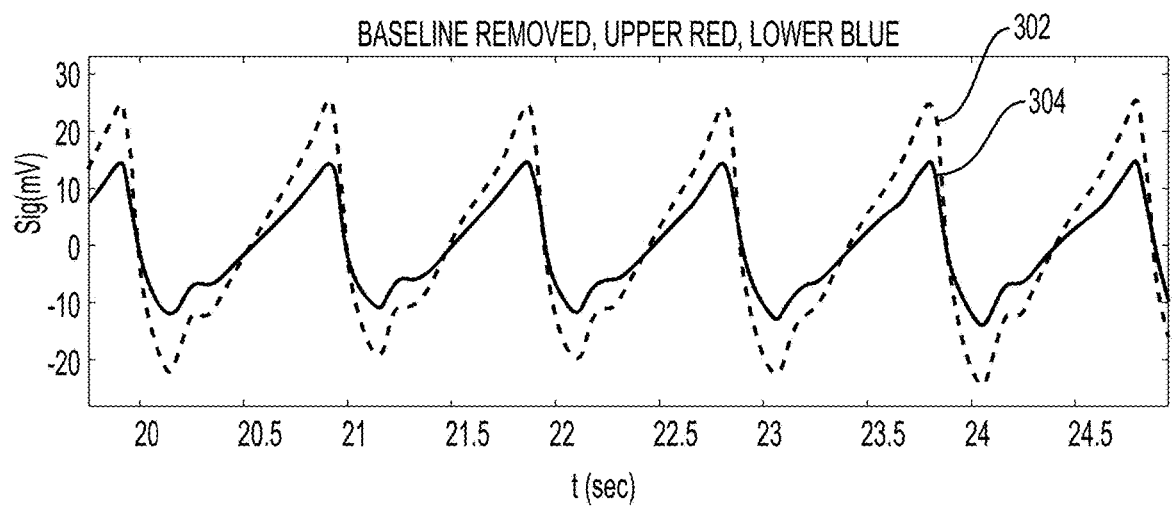
FIGS. 2A and 2B show examples of photoplethysmographic signal(s) acquired via the measurement system of FIG. 1 in accordance with an illustrative embodiment.
Figure 2B:
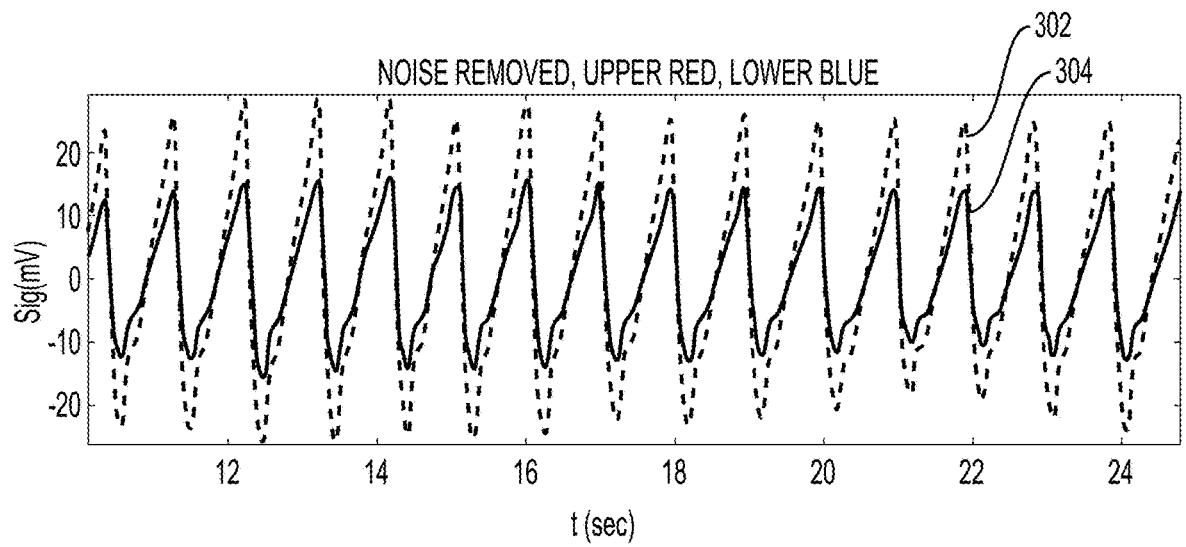
Figure 2C:
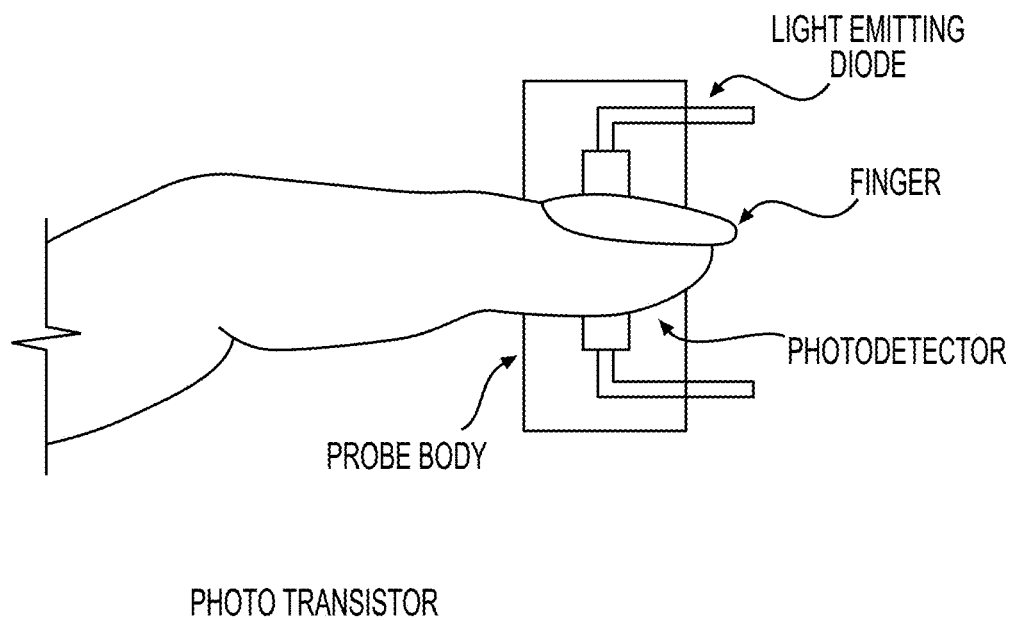
FIG. 2C shows an example sensor configuration to acquire the photoplethysmographic signal(s) of FIG. 2A in accordance with an illustrative embodiment.

FIGS. 2A and 2B show examples of photoplethysmographic signal(s) 104a (also referred to herein as a PPG signal) acquired via measurement system 102 in accordance with an illustrative embodiment. Specifically, FIG. 2A shows a first signal waveform 302 comprising a red photoplethysmographic signal associated with the absorption level of the red spectrum of light by the deoxygenated hemoglobin from a finger of a patient. In some embodiments, the red photoplethysmographic signal has an associated wavelength that spans over 660 nm. FIG. 2A also shows a second signal waveform 304 (also referred to herein as red photoplethysmographic signal) of the absorption level of the infrared spectrum light (e.g., having a wavelength that spans over 940 nm) by the oxygenated hemoglobin from a finger of a patient. Other spectra may be acquired as desired. In addition, measurements may be performed at other parts of the body. In FIG. 2A, the x-axis shows time (in seconds), and the y-axis shows the signal amplitude in millivolts (mv). FIG. 2B shows the signals of FIG. 2A over a larger time scale (x-axis) to include additional data in the waveform. FIG. 2C shows an example sensor configuration to acquire photoplethysmographic signal(s) 104a in accordance with an illustrative embodiment; other configurations are possible. In FIG. 2C, the transmissive system includes a light source (e.g., a red LED and an infrared LED) and a phototransistor (e.g., red detector and infrared detector); the phototransistor is distally located from the light source.

Figure 2D:
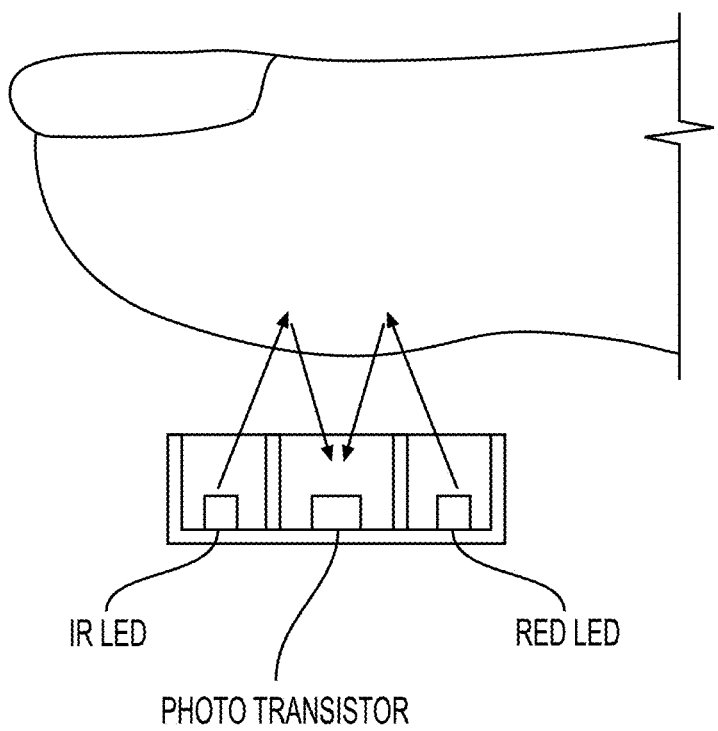
FIG. 2D shows another example sensor configuration to acquire the photoplethysmographic signal(s) of FIG. 2A in accordance with another illustrative embodiment.

FIG. 2D shows another example sensor configuration to acquire photoplethysmographic signal(s) 104 in accordance with another illustrative embodiment. In FIG. 2D, the system also includes a light source (e.g., a red LED and an infrared LED) and a phototransistor (e.g., red detector and infrared detector); however, the phototransistor is proximally located to the light source to measure reflectance.

Photoplethysmography is used to optically measure variations of the volume of blood perfusing tissue (e.g., cutaneous, subcutaneous, cartilage) into which light is emitted, typically at a specific wavelength, from a LED or other sources. The intensity of this light after passing through the tissue (e.g., fingertip, earlobe, etc.) is then registered by a photodetector to provide the photoplethysmographic signals. The amount of light absorbed depends on the volume of the blood perfusing the interrogated tissue. The variation in light absorbed is observable in the photoplethysmographic signal and can provide valuable information with regard to cardiac activity, pulmonary function, their interactions, and other physiological system functions [13].

In some embodiments, measurement system 102 comprises custom or dedicated equipment or circuitry (including off-the-shelf devices) that are configured to acquire such signal waveforms for the purpose of diagnosing disease or abnormal conditions. In other embodiments, measurement system 102 comprises a pulse oximeter or optical photoplethysmographic device that can output acquired raw signals for analysis. Indeed, in some embodiments, the acquired waveform 104 may be analyzed to calculate the level of oxygen saturation of the blood shown in FIG. 1 as "SpO2 reading". For the exemplified analysis application, however, only the waveform is processed and utilized.

Figure 2E:
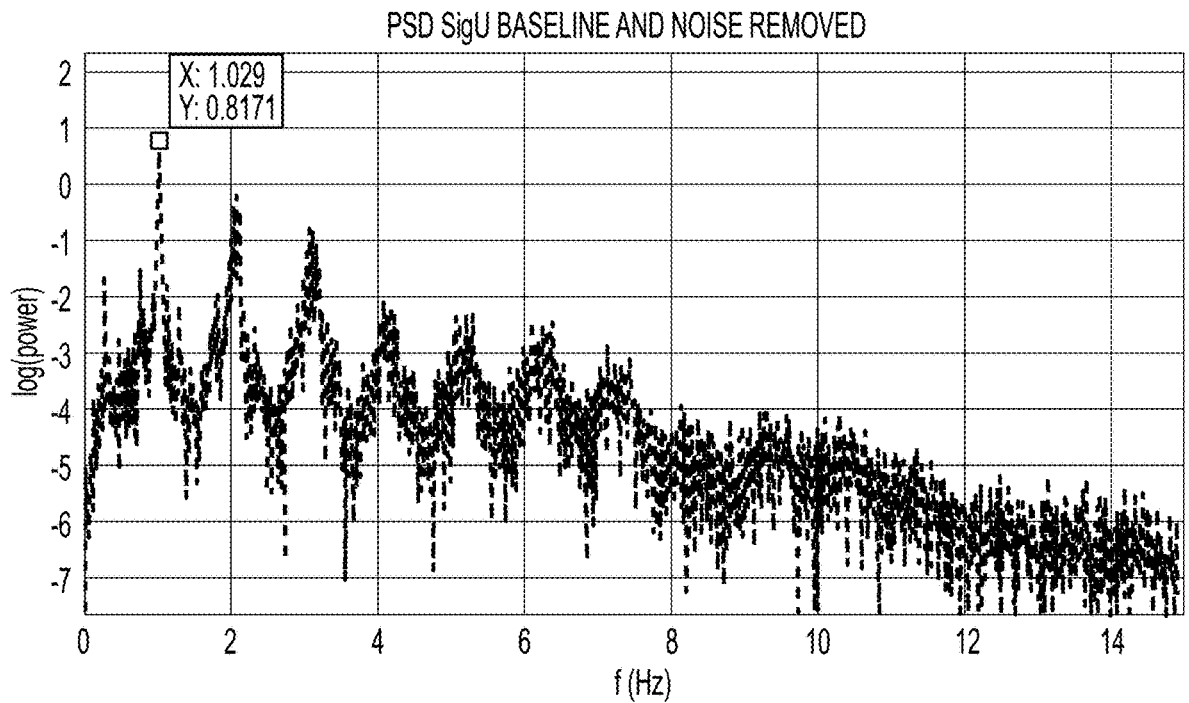
FIGS. 2E and 2F each shows the respective power spectral density of the photoplethysmographic signals of FIG. 2A with high frequency-noise removed.
Figure 2F:
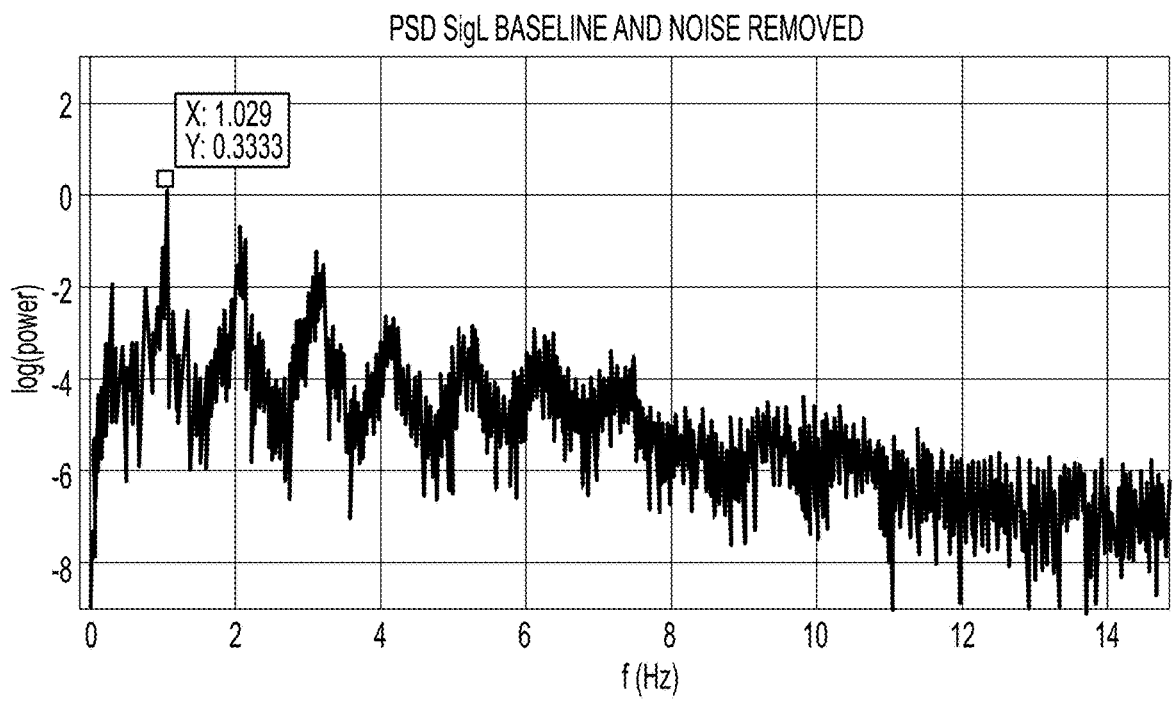

FIGS. 2E and 2F each shows the respective power spectral density of the photoplethysmographic signals of FIGS. 2A and 2B with high frequency-noise removed. In FIGS. 2E and 2F, the x-axis shows frequency (in Hertz), and the y-axis shows the log power of the signal.

Photoplethysmographic signal(s) 104 may be considered measurements of the state of a dynamical system in the body, similar to cardiac signals. The behavior of the dynamical system may be influenced by the actions of the cardiac and respiratory systems. It is postulated that any system aberrations (due, e.g., to a disease or abnormal condition) may manifest themselves in the dynamics of photoplethysmographic signal(s) 104 via some interaction mechanism or mechanisms.

In some embodiments, the acquired photoplethysmographic signal(s) 104 are down-sampled to 250 Hz. Other frequency ranges may be used. In some embodiments, the acquired photoplethysmographic signal(s) 104 are processed to remove baseline wander and/or to filter for noise and/or mains frequencies.

Figure 4A:
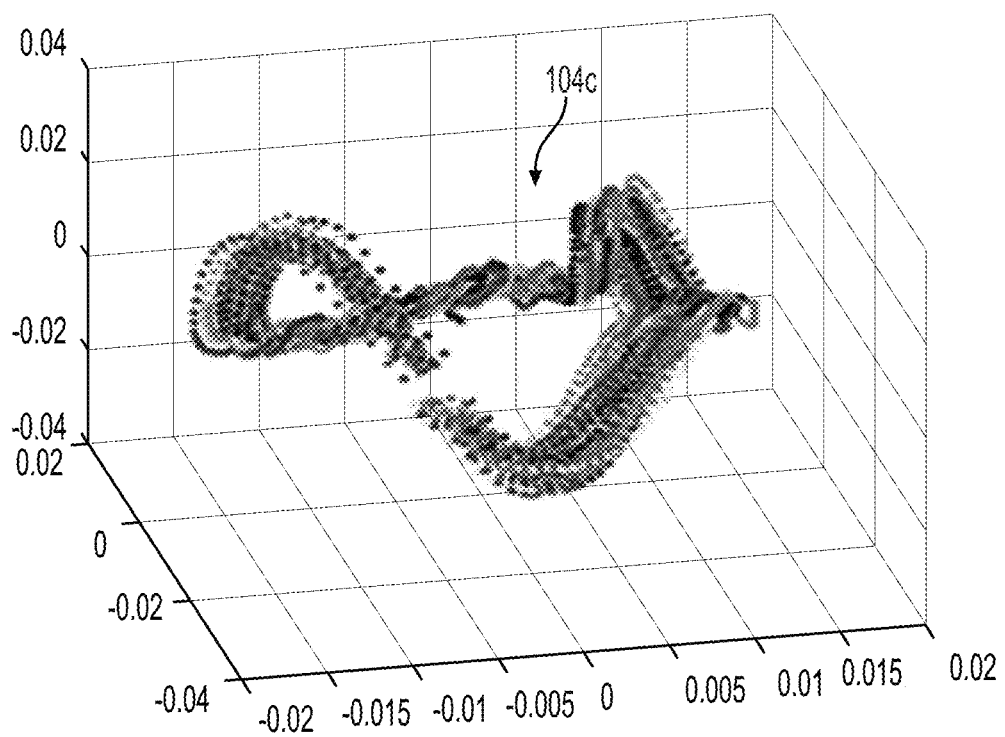
FIG. 4A shows a three-dimensional phase space plot of photoplethysmographic signals acquired via an infrared sensor in accordance with an illustrative embodiment.
Figure 4B:
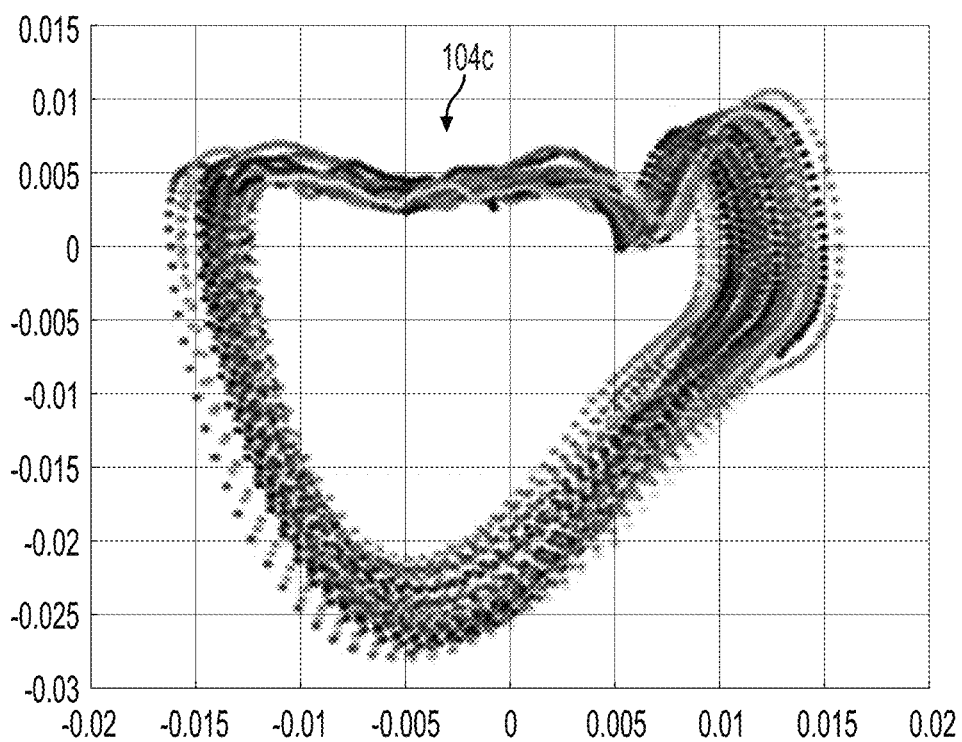
FIG. 4B shows a two-dimensional projection of the same data of FIG. 4A in accordance with an illustrative embodiment.

The acquired photoplethysmographic signal(s) 104 may be embedded in some higher dimensional space (e.g., phase space embedding) to reconstruct the manifold (phase space) the underlying dynamical system creates. An example three-dimensional visualization and its two-dimensional projection of acquired photoplethysmographic signal(s) 104 (shown as 104c) are shown in FIGS. 4A and 4B, respectively. Specifically, FIG. 4A shows a 3D phase space plot of an acquired photoplethysmographic signal(s) 104 acquired via an infrared sensor. Axes are transformed voltage values. Colors are selected to show coherent structures within this geometric object. The dynamical features of the PPG are calculated based on the embedding represented by the figure. Description of embedding may be found in Sauer et al., Embedology, Jour. Of Statistical Physics, Vol. 65: 3-4, pp 579-616 (November 1991). FIG. 4B shows a two-dimensional projection of the same, and the same axes of FIG. 4A are shown.

Example Cardiac Signals

Electrocardiographic signals measure the action potentials of cardiac tissue (i.e., cardiomyocytes). There are various configurations of leads that can be used in a mammalian body, and in particular humans, to obtain these signals in the context of the present disclosure. In an example configuration, seven leads are used. This configuration results in three orthogonal channels/signals; e.g., X, Y and Z, corresponding to the coronal, sagittal and transverse planes, respectively.

As discussed above, in some embodiments, cardiac signal data set 110b includes data associated with biopotential signals acquired across a plurality of channels. In some embodiments, cardiac signal data set 110b includes wide-band biopotential signals, e.g., signals acquired via a phase-space recorder such as described in U.S. Patent Publication No. 2017/0119272, entitled "Method and Apparatus for Wide-Band Phase Gradient Signal Acquisition," which is incorporated by reference herein in its entirety. In some embodiments, the cardiac signal data set includes bipolar wide-band biopotential signals, e.g., acquired via a phase-space recorder such as described in U.S. Patent Publication No. 2018/0249960, entitled "Method and Apparatus for Wide-Band Phase Gradient Signal Acquisition," which is incorporated by reference herein in its entirety. In other embodiments, the cardiac signal data set 110b includes one or more biopotential signals acquired from conventional electrocardiogram (ECG/EKG) equipment (e.g., Holter device, 12 lead ECG, etc.).

The phase space recorder as described in 2017/0119272, in some embodiments, is configured to concurrently acquire photoplethysmographic signals 104a along with cardiac signal 104b. Thus, in some embodiments, measurement system 102b is configured to acquire two types of biophysical signals.

Figure 3A:
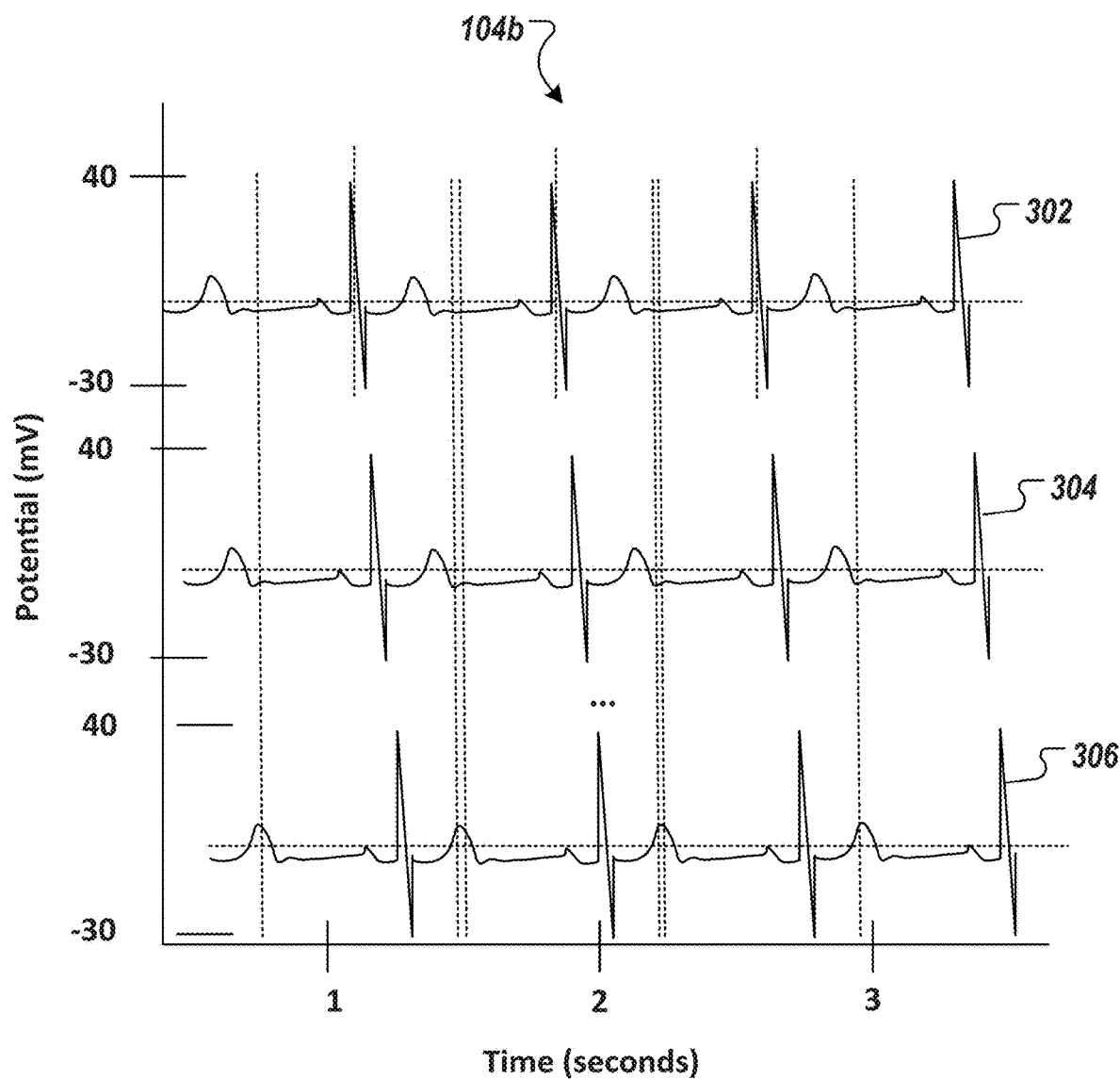
FIG. 3A shows example cardiac signals (e.g., biopotential signals) as example biophysical signals acquired via the measurement system of FIG. 1, in accordance with an illustrative embodiment.

FIG. 3A shows example cardiac signals (e.g., biopotential signals) as example biophysical signals acquired via the measurement system of FIG. 1, in accordance with an illustrative embodiment. The signals are shown with baseline wander and high-frequency noise removed. In some embodiments, the cardiac signals 104b are acquired using a phase space recorder device, e.g., such as described in U.S. Patent Publication No. 2017/0119272. The signals 104b includes bipolar biopotential measurements acquired over three channels to provide three signals 302, 304, 306 (also referred to channel "x," channel "y," and channel "z" or the coronal, sagittal, and transverse planes, respectively). In FIG. 3A, the x-axis shows time (in seconds), and the y-axis shows the signal amplitude in millivolts (mv).

Figure 3B:
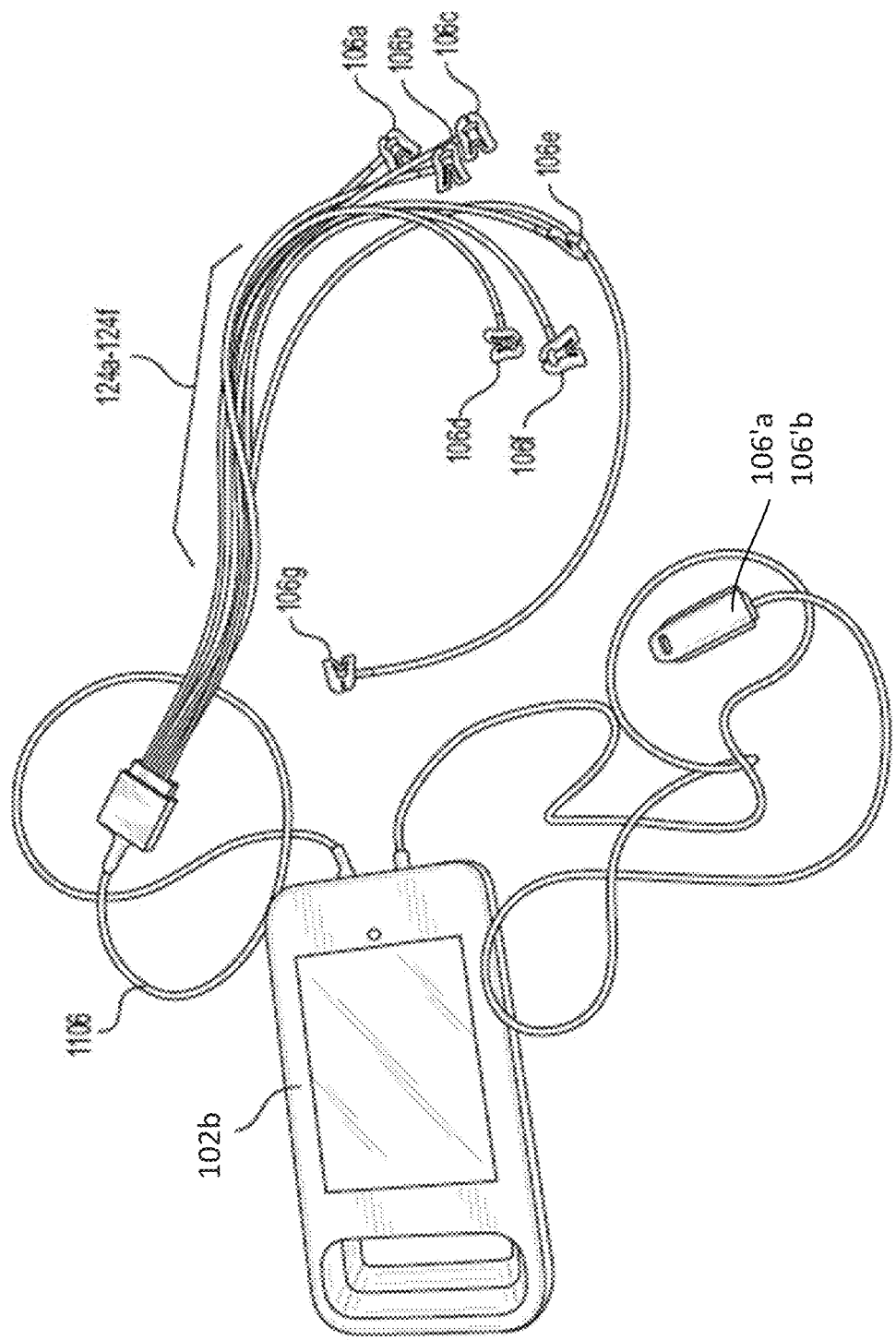
FIG. 3B is an example measurement system, such as that depicted in FIG. 1, configured to non-invasively measure biophysical signals to be used to assess dynamical properties of a physiological system to predict and/or estimate the presence, non-presence, severity, and/or localization (where applicable) of disease or condition, or an indicator of one, in such physiological system, in accordance with an illustrative embodiment.
Figure 3C:
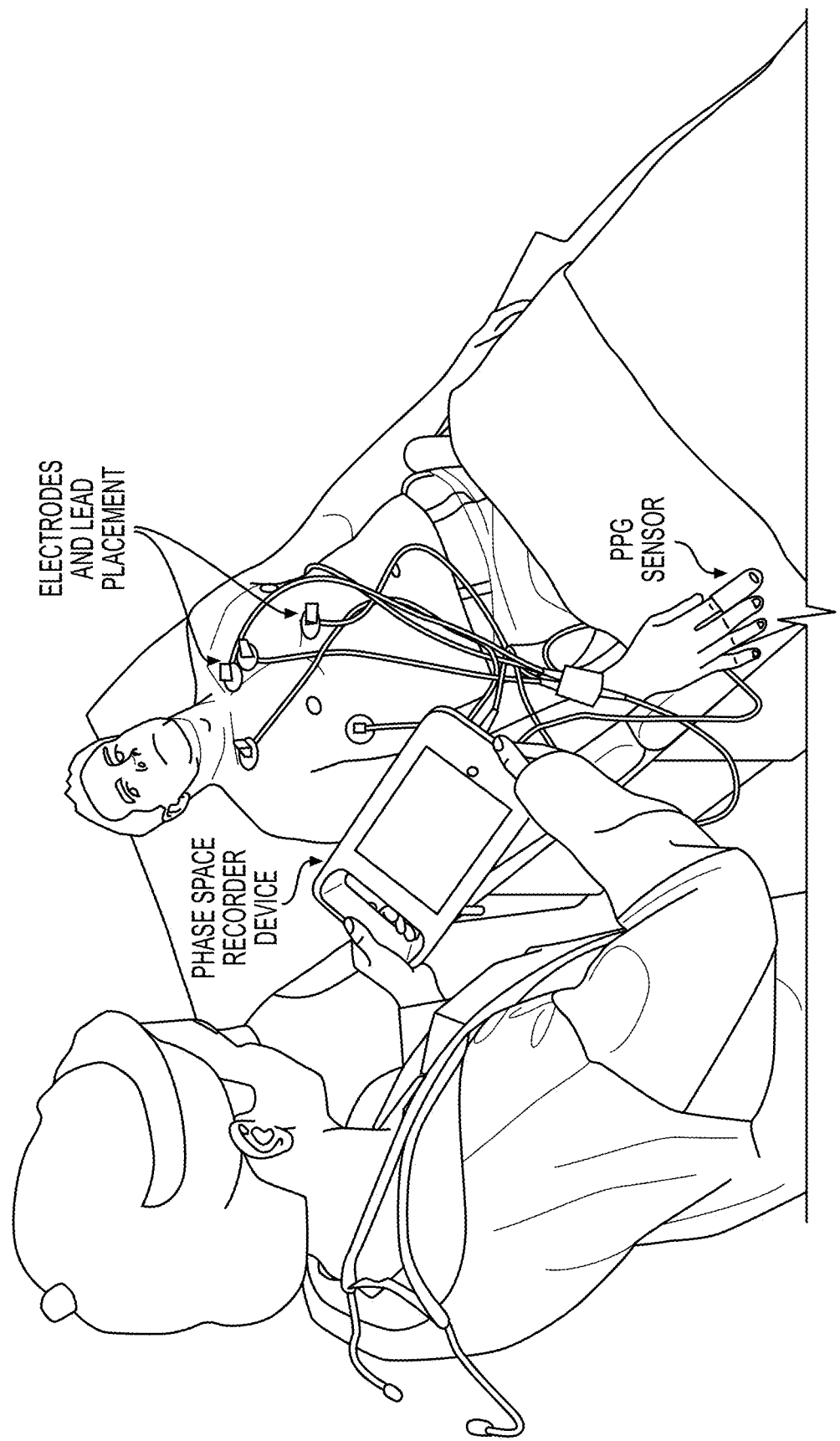
FIG. 3C shows an example use of the measurement system of FIG. 3B on a patient in a clinical setting in accordance with an illustrative embodiment.

FIG. 3B is a diagram of a phase space recorder device, e.g., as described in U.S. Patent Publication No. 2017/0119272, configured to acquire cardiac signals 104b. The phase space recorder device is further configured to also acquire photoplethysmographic signals 104a. FIG. 3C shows an example placement of the measurement system of FIG. 3B on a human patient.

Referring still to FIG. 1B, non-invasive measurement system 102b is configured to transmit, e.g., over a communication system and/or network, or over direct connection, the acquired cardiac-signal data set 110b, or a data set derived or processed therefrom, to repository 112 (e.g., a storage area network) that is accessible to a non-invasive biophysical-signal assessment system. The non-invasive biophysical-signal assessment system 114 (shown as analytic engine 114) is configured to analyze dynamical properties of the acquired photoplethysmographic signal(s).

In the cardiac and/or electrocardiography contexts, measurement system 102 is configured to capture cardiac-related biopotential or electrophysiological signals of a mammalian subject (such as a human) as a biopotential cardiac signal data set. In some embodiments, measurement system 102 is configured to acquire wide-band cardiac phase gradient signals as a biopotential signal, a current signal, an impedance signal, a magnetic signal, an ultrasound or acoustic signal, etc. The term "wide-band" in reference to an acquired signal, and its corresponding data set, refers to the signal having a frequency range that is substantially greater than the Nyquist sampling rate of the highest dominant frequency of a physiological system of interest. For cardiac signals, which typically has a dominant frequency component between about 0.5 Hz and about 80 Hz, the wide-band cardiac phase gradient signals or wide-band cardiac biophysical signals comprise cardiac frequency information at a frequency selected from the group consisting between about 0.1 Hz and 1 kHz, between about 0.1 Hz and about 2 kHz, between about 0.1 Hz and about 3 kHz, between about 0.1 Hz and about 4 kHz, between about 0.1 Hz and about 5 kHz, between about 0.1 Hz and about 6 kHz, between about 0.1 Hz and about 7 kHz, between about 0.1 Hz and about 8 kHz, between about 0.1 Hz and about 9 kHz, between about 0.1 Hz and about 10 kHz, and between about 0.1 Hz and greater than 10 kHz (e.g., 0.1 Hz to 50 kHz or 0.1 Hz to 500 kHz). In addition to capturing the dominant frequency components, the wide-band acquisition also facilitates the capture of other frequencies of interest. Examples of such frequencies of interest can include QRS frequency profiles (which can have frequency ranges up to 250 Hz), among others. The term "phase gradient" in reference to an acquired signal, and corresponding data set, refers to the signal being acquired at different vantage points of the body to observe phase information for a set of distinct events/functions of the physiological system of interest. Following the signal acquisition, the term "phase gradient" refers to the preservation of phase information via the use of non-distorting signal processing and pre-processing hardware, software, and techniques (e.g., phase-linear filters and signal-processing operators and/or algorithms).

In some embodiments, cardiac signal data set 110b includes wide-band biopotential signals, such as, e.g., those acquired via a phase-space recorder as described in U.S. Patent Publication No. 2017/0119272, entitled "Method and Apparatus for Wide-Band Phase Gradient Signal Acquisition," which is incorporated by reference herein in its entirety. In some embodiments, the cardiac signal data set includes bipolar wide-band biopotential signals, e.g., acquired via a phase-space recorder such as described in U.S. Patent Publication No. 2018/0249960, entitled "Method and Apparatus for Wide-Band Phase Gradient Signal Acquisition," which is incorporated by reference herein in its entirety. In other embodiments, the cardiac signal data set 110b includes one or more biopotential signals acquired from conventional electrocardiogram (ECG/EKG) equipment (e.g., Holter device, 12 lead ECG, etc.).

The phase space recorder as described in U.S. Patent Publication No. 2017/0119272, in some embodiments, is configured to concurrently acquire photoplethysmographic signals 104a along with cardiac signal 104b. Thus, in some embodiments, measurement system 102b is configured to acquire two types of biophysical signals.

In the neurological context, measurement system 102 is configured to capture neurological-related biopotential or electrophysiological signals of a mammalian subject (such as a human) as a neurological biophysical-signal data set. In some embodiments, measurement system 102 is configured to acquire wide-band neurological phase gradient signals as a biopotential signal, a current signal, an impedance signal, a magnetic signal, an ultrasound or acoustic signal, an optical signal, etc. An example of measurement system 102 is described in U.S. Patent Publication No. 2017/0119272 and in U.S. Patent Publication No. 2018/0249960, which is incorporated by reference herein in its entirety.

In some embodiments, the measurement system 102 is configured to capture wide-band biopotential biophysical phase gradient signals as unfiltered mammalian electrophysiological signals such that the spectral component(s) of the signals are not altered. Indeed, in such embodiments, the wide-band biopotential biophysical phase gradient signals are captured, converted, and even analyzed without having been filtered (via, e.g., hardware circuitry and/or digital signal processing techniques, etc.) (e.g., prior to digitization) that otherwise can affect the phase linearity of the biophysical signal of interest. In some embodiments, the wide-band biopotential biophysical phase gradient signals are captured in microvolt or sub-microvolt resolutions that are at, below, or significantly below, the noise floor of conventional electrocardiographic, electroencephalographic, and other biophysical-signal acquisition instruments. In some embodiments, the wide-band biopotential biophysical signals are simultaneously sampled having a temporal skew or "lag" of less than about 1 microsecond, and in other embodiments, having a temporal skew or lag of not more than about 10 femtoseconds. Notably, the exemplified embodiments minimize non-linear distortions (e.g., those that can be introduced via certain filters) in the acquired wide-band phase gradient signal to not affect the information therein.

Figure 3D:
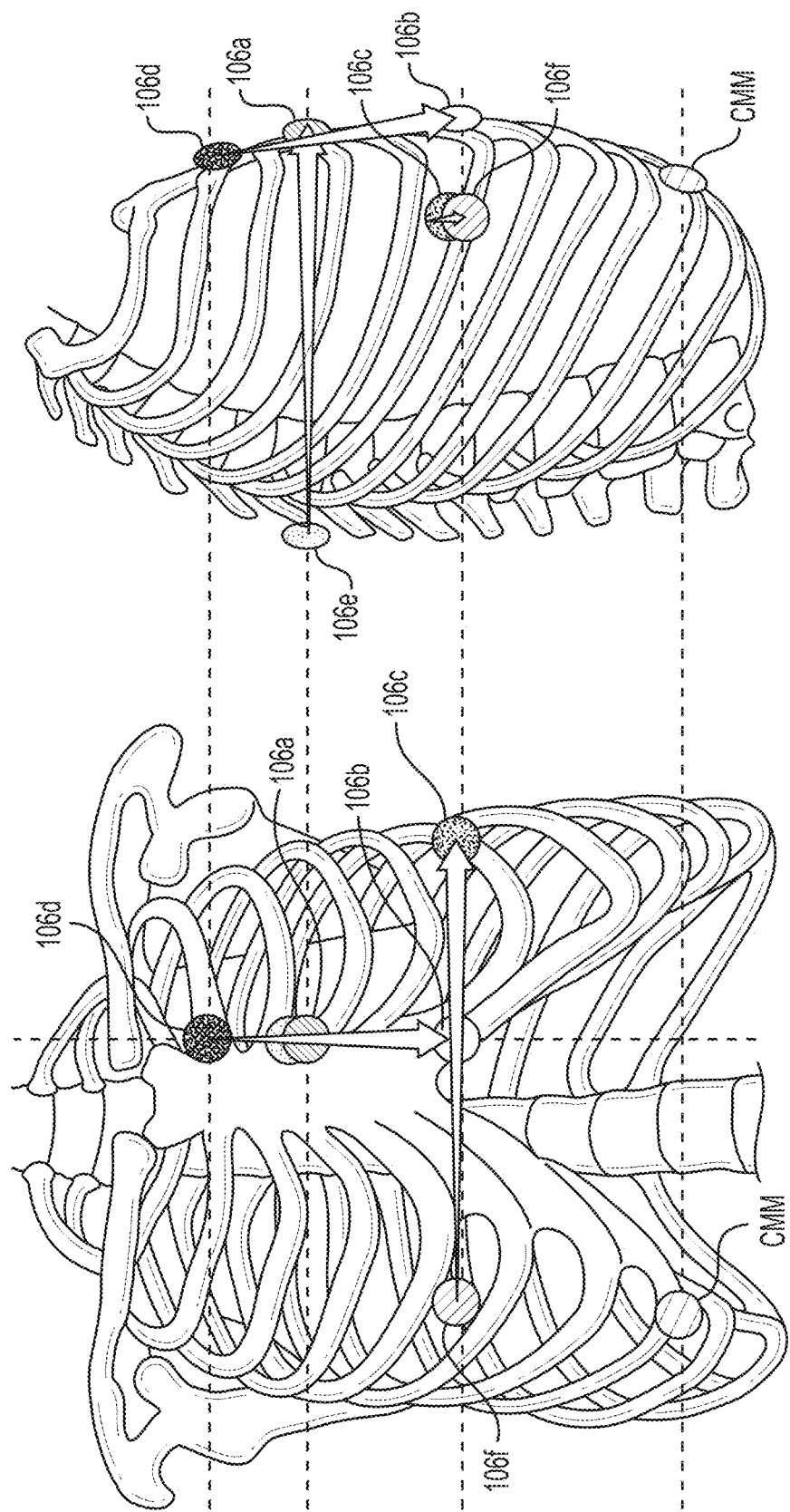
FIG. 3D is a diagram of an example placement of the surface electrodes of the measurement system of FIG. 3B at the chest and back of a patient to acquire the cardiac signals of FIG. 3A in accordance with an illustrative embodiment.

FIG. 3D is a diagram of an example placement of the surface electrodes 106a-106g at a patient to acquire the cardiac signals of FIG. 3A in accordance with an illustrative embodiment. Specifically, FIG. 3D shows example placement of the surface electrodes 106a-106g at the chest and back of a patient to acquire bio-potential signals associated with wide-band cardiac phase gradient signals in accordance with an illustrative embodiment. In the left pane of FIG. 3D, surface electrodes 106a-106g are shown placed at the chest and back area of the patient. In the right pane of FIG. 3D, a side view of the placement of the surface electrodes 106a-106g is shown.

In the example configuration shown in FIG. 3D, surface electrodes 106a-106g are positioned on the patient's skin at i) a first location proximal to a right anterior axillary line corresponding to a 5th intercostal space; ii) a second location proximal to a left anterior axillary line corresponding to the 5th intercostal space; iii) a third location proximal to a left sternal border corresponding to a 1st intercostal space; iv) a fourth location proximal to the left sternal border below the sternum and lateral to the patient's xiphoid process; v) a fifth location proximal to the left sternal border corresponding to a 3rd intercostal space; vi) a sixth location proximal to the patient's back directly opposite of the fifth location and left of the patient's spine; and viii) a seventh location proximal to a right upper quadrant corresponding to a 2nd intercostal space along a left axillary line. A common lead (shown as "CMM") is also shown. Locations of individual surface electrodes may vary in other embodiments of the present disclosure as other electrode configurations may be useful.

Referring to FIG. 1, non-invasive measurement system 102 is configured with circuitry and computing hardware, software, firmware, middleware, etc. to acquire both the cardiac signal and the photoplethysmographic signal to generate the biophysical-signal data set 110. In other embodiments, non-invasive measurement system 102 includes a first equipment (not shown) to acquire the cardiac signal and includes a second equipment (not shown) to acquire the photoplethysmographic signal.

Referring still to FIG. 1, non-invasive measurement system 102 is configured to transmit, e.g., over a communication system and/or network, or over a direct connection, the acquired biophysical-signal data set 110, or a data set derived or processed therefrom, to a repository 112 (e.g., a storage area network) (not shown) that is accessible to a non-invasive biophysical-signal assessment system. The non-invasive biophysical-signal assessment system 114 (shown as analytic engine 114) is configured to, e.g., analyze dynamical properties of the acquired photoplethysmographic signal(s).

In some embodiments, analytic engine 114 includes a machine learning module 116 configured to assess a set of features determined via one or more feature extraction modules (e.g. 118, 120) from the acquired biophysical signal(s) to determine features of clinical significance. Once the features have been extracted from the PPG signal(s) or cardiac signal(s), then any type of machine learning can be used. Examples of embodiments of machine learning module 116 are configured to implement, but not limited to, decision trees, random forests, SVMs, neural networks, linear models, Gaussian processes, nearest neighbor, SVMs, Naïve Bayes. In some embodiment, machine learning module 116 may be implemented, e.g., as described in U.S.

patent application Ser. No. 15/653,433, entitled "Discovering Novel Features to Use in Machine Learning Techniques, such as Machine Learning Techniques for Diagnosing Medical Conditions"; and U.S. patent application Ser. No. 15/653,431, entitled "Discovering Genomes to Use in Machine Learning Techniques"; each of which is incorporated by reference herein in its entirety. The photoplethysmographic signal(s) may be combined with other acquired photoplethysmographic signal(s) to be used in a training data set or validation data set for the machine learning module 116 in the evaluation of a set of assessed dynamical features. The photoplethysmographic signal(s) may have an associated label 122 for a given disease state or abnormal condition, or an indicator of one. If determined to be of clinical significance, an assessed dynamical feature (e.g., from 118 or 120) may be subsequently used as a predictor for the given disease or abnormal condition, or an indicator of one.

In some embodiments, analytic engine 114 includes a pre-processing module, e.g., configured to normalize and/or remove baseline wander from the acquired photoplethysmographic signal(s).

In some embodiments, system 100 includes a healthcare provider portal to display, e.g., in a report, score or various outputs of the analytic engine 114 in predicting and/or estimating the presence, non-presence, severity, and/or localization (where applicable) of a disease or abnormal condition, or an indicator of one. The physician or clinician portal, in some embodiments, is configured to access and retrieve reports from a repository (e.g., a storage area network). The physician or clinician portal and/or repository can be compliant with various privacy laws and regulations such as the U.S. Health Insurance Portability and Accountability act of 1996 (HIPAA). Further description of an example healthcare provider portal is provided in U.S. Pat. No. 10,292,596, entitled "Method and System for Visualization of Heart Tissue at Risk", which is incorporated by reference herein in its entirety. Although in certain embodiments, the portal is configured for the presentation of patient medical information to healthcare professionals, in other embodiments, the healthcare provider portal can be made accessible to patients, researchers, academics, and/or other portal users.

Synchronicity Evaluation between Cardiac Signal and Raw Photoplethysmographic Signals Referring still to FIG. 1, the dynamical feature extraction module 118, in some embodiments, is configured to evaluate one or more nonlinear dynamical properties of synchronicity between one or more of acquired photoplethysmographic signal(s) 104a and one or more of the acquired cardiac signal 104b. Several examples of synchronicity are disclosed.

The electrophysiological activity of the heart is a nonlinear process which in conjunction with the myocytes' mechano-electrical feedback produces very complex nonlinear responses [26]. These behaviors whether normal (reaction to extrinsic conditions) or due to a disease can be studied and characterized using nonlinear statistics related to the nonlinear dynamics and chaoticity of the heart. Synchronicity features that are based on dynamics observed in cardiac and photoplethysmographic signals may encode the health state of the heart and are used to train a machine learning model for the prediction of various disease states or conditions.

In a Poincaré map, the mapping $X_{n+1}+i=P(X_n)$ may be defined using triggers (e.g., intersection with $\Sigma$), and the set of Poincaré points $\{X_0, X_1, \ldots, X_n\}$ can then be analyzed geometrically and/or statistically to deduce more information about the system.

Synchronicity Features Example PM #1

Figure 5A:
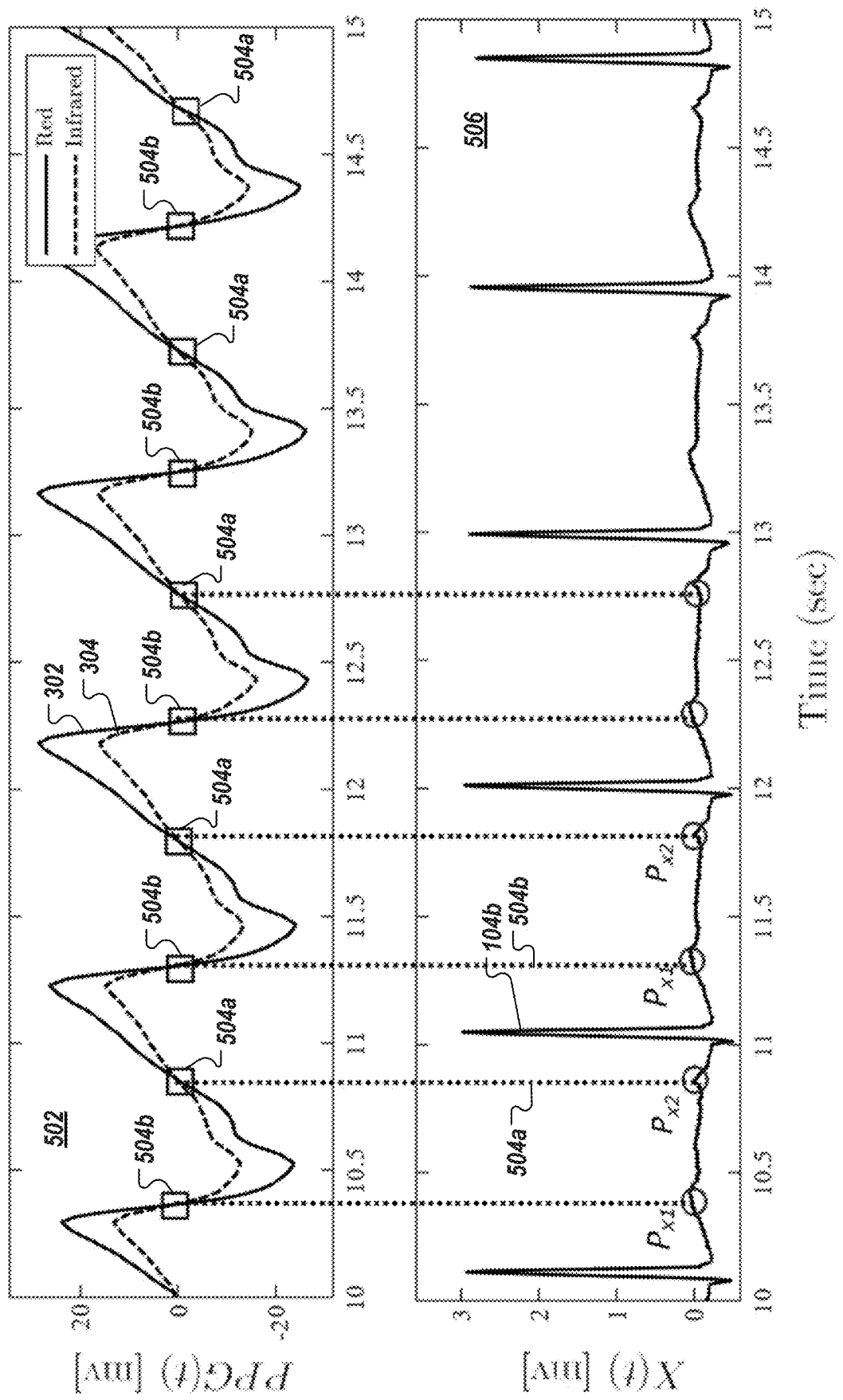
FIGS. 5A, 5B, and 5C illustrate example dynamical properties of synchronicity between acquired photoplethysmographic and cardiac signals in accordance with an illustrative embodiment.
Figure 5B:
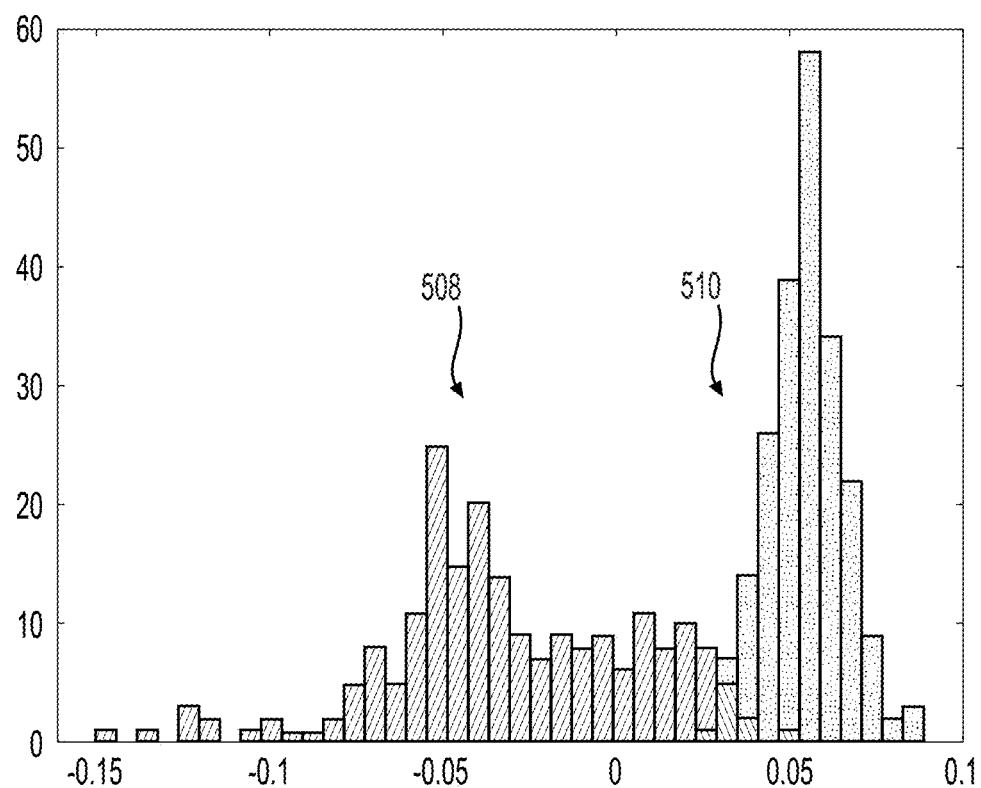
Figure 5C:
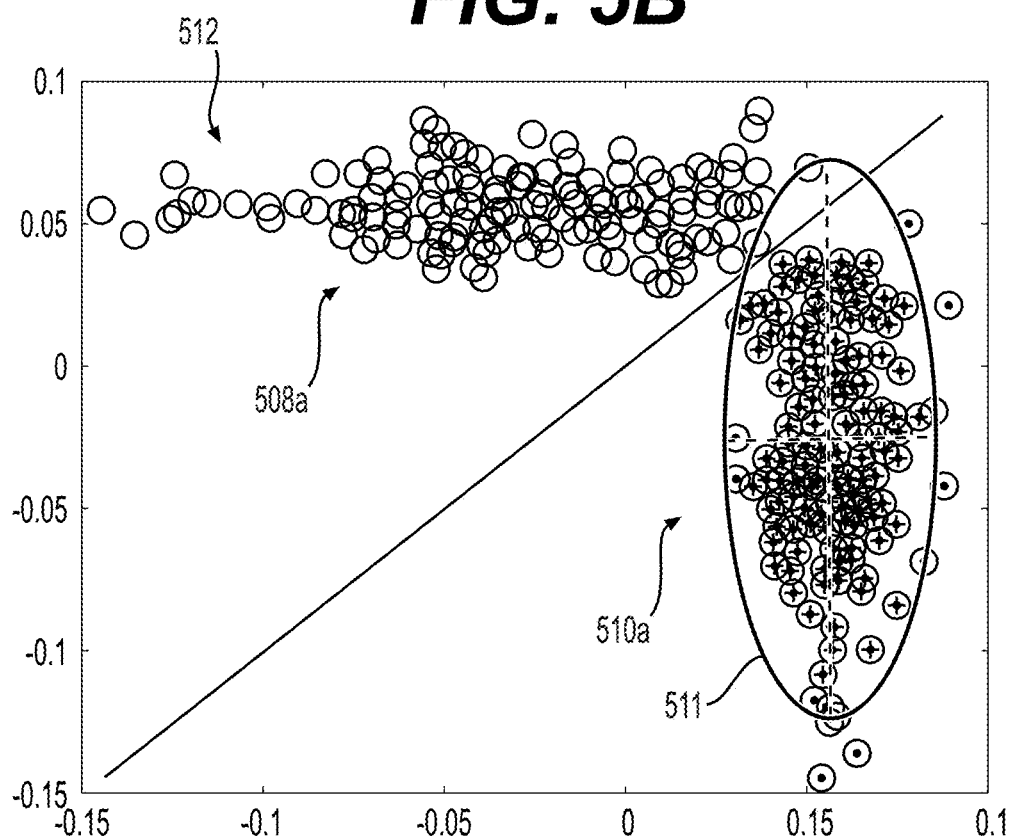

FIGS. 5A, 5B, and 5C illustrate example dynamical properties of synchronicity between acquired photoplethysmographic signal and cardiac signals in accordance with an illustrative embodiment. Specifically, in FIGS. 5A, 5B, and 5C, synchronicity is determined, via histogram/Poincaré map analysis, using landmarks defined by the photoplethysmographic signals.

Specifically, FIG. 5A shows, in a first plot 502, cross-over landmarks 504a and 504b defined between a red photoplethysmographic signal 302 and an infrared photoplethysmographic signal 304. A second plot 506 shows the cross-over landmarks 504a and 504b in relation to one of the channels of the acquired cardiac signal 104b. In FIG. 5A, the x-axis shows time (in seconds), and the y-axis shows the signal amplitude in millivolts (mv).

FIG. 5B shows a histogram of the distribution of values of the cardiac signal 104b at the cross-over landmarks 504a and 504b. Specifically, FIG. 5B shows distributions 508, 510 corresponding to amplitude values of the cardiac signal at the respective first and second sets of crossover landmarks (504a, 504b). In FIG. 5B, the x-axis of the histogram shows signal amplitude (in mV), and the y-axis shows the frequency/count.

In some embodiments, dynamical feature extraction module 118 is configured to generate a histogram (e.g., as generated per FIG. 5B) and extract statistical and geometric properties from the generated histogram. In some embodiments, the extracted histogram features include, for example, but not limited to, modes, standard derivation, skewness, kurtosis, and mutual information. Mode refers to the set of data values that appear most often in a date set. Skewness refers to a measure of the asymmetry of the probability distribution of the data set about its mean. Kurtosis refers to the sharpness of the peak of a distribution curve. In some embodiments, mutual information is used to quantify the probabilistic dependence of the information in the acquired signals and is determined by first calculating a probability normalization of the histogram of each time series and then constructing and normalization a 2-dimensional histogram of the two time-series. The mutual information I(X, Y) between two random variables X and Y can be the amount of reduction in the uncertainty of one random variable, say, X given another variable Y defined per Equation 1.

$$I(X,Y)=\sum_{y \in Y}\sum_{x \in X} p(x,y)\log(p(x,y)/p(x)p(y)) \quad \text{(Equation 1)}$$

In Equation 5, p(.,.) is the probability distribution over the specified variables.

FIG. 5C shows a Poincaré map 512 of values of the cardiac signal 104b at the crossover landmarks 504a and 504b. That is, the Poincaré map records the value of the cardiac signal 104b, or at least one of the channels, based on triggers defined by the crossover landmarks 504a, 504b. In FIG. 5C, the x-axis and y-axis each shows the difference in amplitude values for the cardiac signal from cycles to cycles.

In some embodiments, to generate the Poincaré map 512, the system plots/generates a 2D pairs of points $[x_i, x_{i+1}]$ (e.g., $(x_1, x_2), (x_2, x_3)$, etc.) against the points $[x_i, x_{i+1}]$ (e.g., $(x_0, x_1), (x_1, x_2)$, etc.) of the amplitude values of a cardiac signal at the cross-over landmark points formed between photoplethysmographic signals.

In some embodiments, dynamical feature extraction module 118 is configured to generate Poincaré map 512. Following the generation of Poincaré map 512, dynamical feature extraction module 118, in some embodiments, is configured to generate a geometric object from the map data. In FIG. 5C, in some embodiments, dynamical feature extraction module 118 determines an ellipse 511 based on an ellipse fit operation of the data associated with a cluster (e.g., 510a). Based on the fitted ellipse, dynamical feature extraction module 118, in some embodiments, is configured to determine geometric parameters such as, but not limited to, length of semi axis "a" (514), semi axis "b" (516), length along a long axis (518), and length along a short axis (520) as shown in FIG. 5D.

The dynamical feature extraction module 118, in some embodiments, may extract other parameters such as void area, surface area, porosity, perimeter length, density, among others.

Indeed, synchronicity between acquired photoplethysmographic signals (e.g., where acquired raw signals are merely processed to remove baseline wander and high frequency noise) and a cardiac signal based on triggers defined in the photoplethysmographic signal may be used to assess for the presence, non-presence, severity, and/or localization (where applicable) of coronary artery disease (CAD), pulmonary hypertension, heart failure in various forms, among other diseases and conditions. In the CAD context, FIG. 5E shows an example Poincaré map of a data set acquired from a CAD-negative patient (i.e., a patient who does not have CAD). FIG. 5F shows an example Poincaré map of a data set acquired from a CAD-positive patient (i.e., a patient who has CAD in some form). It is readily apparent that the Poincaré maps of FIGS. 5E and 5F between a CAD-negative patient and a CAD-positive patient are different. FIGS. 5E and 5F each shows an example Poincaré map generated from the amplitude values of a cardiac signal at landmarks defined by the photoplethysmographic signals. In the x- and y-axis, the Poincaré map shows the signal amplitude of the cardiac signal (e.g., as normalized with high-frequency and baseline wander removed) at a first index x−1 and a second index x in the x-axis and the second index x and third index x+1 in the y-axis. Indeed, in a Poincaré map, time and data positions as denoted by an index value are synonymous are used interchangeably herein. Additionally, other index or time increments may be used. That is, each assessed parameter (e.g., signal amplitude) at a given time/data point is shown in the Poincaré map with respect to the next time/data point (e.g., [xi−1, x] versus [x, xi+1]). The Poincaré map thus facilitates the analysis of variability of a given parameter (e.g., variability in the lowest peak landmarks) between cycles in the acquired data set. Similar analysis may be applied to any of the parameters and features discussed herein.

Figure 5G:
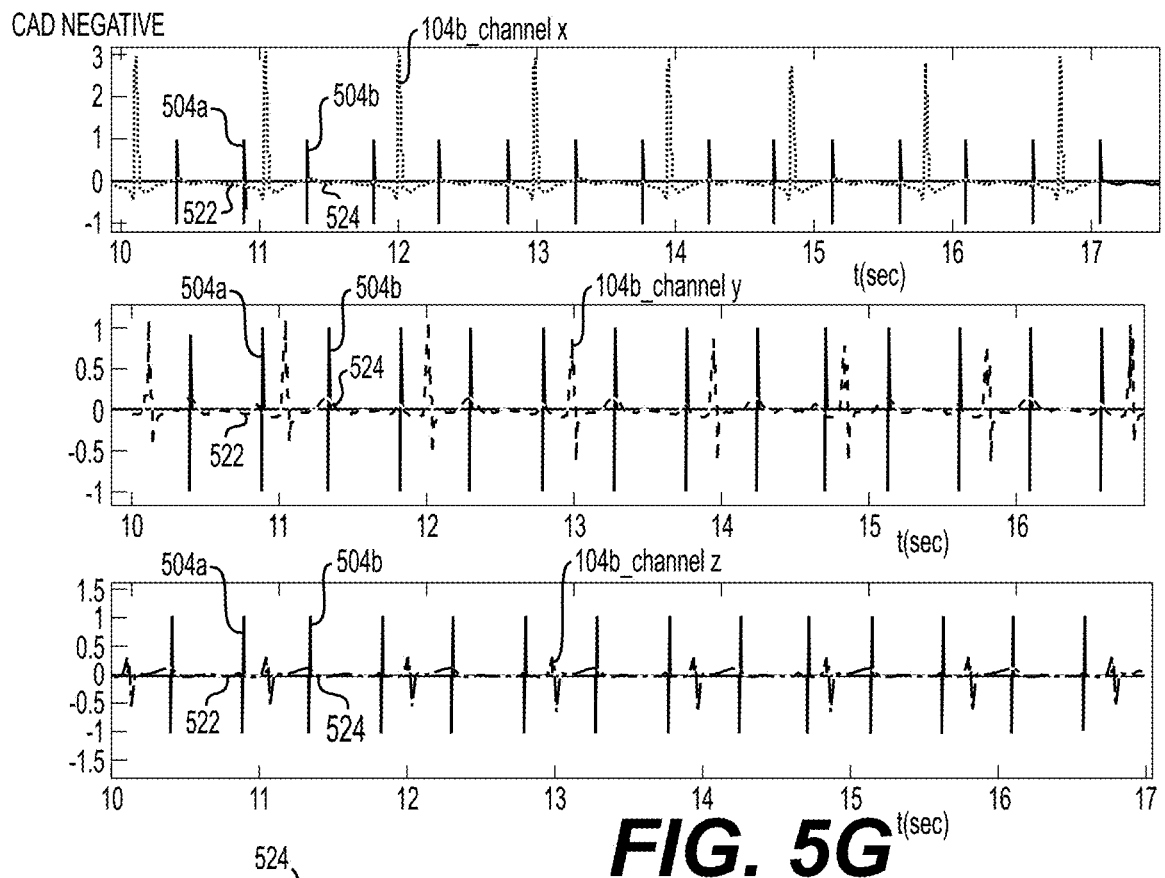
FIGS. 5G and 5H further shows crossover landmarks with respect to three cardiac signals acquired via a phase space recorder that can be used to trigger analysis of a photoplethysmographic signal in Poincaré maps in accordance with an illustrative embodiment.
Figure 5H:
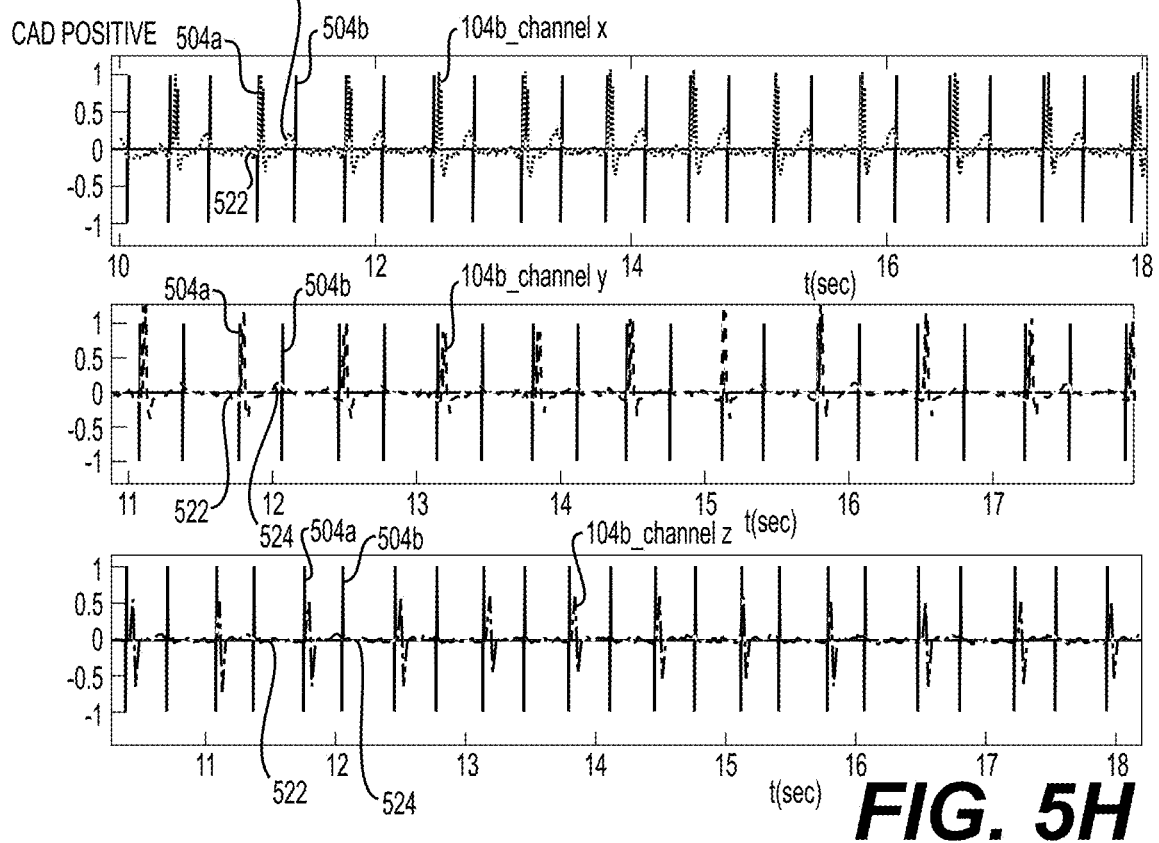

FIGS. 5G and 5H further show crossover landmarks (504a, 504b) with respect to three cardiac signals acquired via a phase space recorder that can be used to trigger analysis of a photoplethysmographic signal in a Poincaré map. Description of an example phase space recorder and its associated probe locations are described, for example, in U.S. Patent Publication No. 2018/0249960, entitled "Method and Apparatus for Wide-Band Phase Gradient Signal Acquisition," which is incorporated by reference herein in its entirety. In FIG. 5G, the data set is shown for a CAD-negative patient. In FIG. 5H, the data set is shown for a CAD-positive patient.

Specifically, in FIG. 5G, it is observed that the crossover landmarks from the photoplethysmographic signals generally correspond to the P-waves (522) and T-waves (524) of cardiac signals 104b (shown as 104b_channel x, 104b_channel y, and 104b_channel z). P-waves generally correspond to atrial depolarization associated with atrial contraction and atrial systole. T-waves generally correspond to ventricular repolarization.

In contrast, as shown in FIG. 5H, for CAD-positive patients, it can be observed that the crossover landmarks from the photoplethysmographic signals have shifted with respect to the P-waves and T-waves. The Poincaré map (e.g., as described in relation to FIG. 5C) facilies the quantification, and in some embodiments, visualization, of this resulting shift which is understood to be a condition of a disease—here, coronary artery disease or CAD.

In FIGS. 5G and 5H, the amplitude value of a cardiac signal at landmarks in the photoplethysmographic signals are plotted in pairs (e.g., at a first time x−1 and a second time x in the x-axis and at second time x and a third time x+1 in the y-axis).

FIGS. 5I, 5J, 5K, and 5L illustrate another example of dynamical properties of synchronicity between an acquired photoplethysmographic signal and cardiac signals in accordance with an illustrative embodiment. Specifically, FIG. 5I shows a histogram of a distribution of Px1 and Px2 Poincaré points, e.g., as shown in FIG. 5A, for a healthy patient (i.e., CAD negative patient), and FIG. 5J shows a Poincaré map of the same data along with an ellipse fit to geometrically characterize the data distribution. FIG. 5K show a histogram of a distribution of Px1 and Px2 Poincaré points, e.g., as shown in FIG. 5A, for an unhealthy patient (i.e., CAD positive patient), and FIG. 5L shows a corresponding Poincaré map and ellipse fit of the same.

Statistical properties of these distributions (e.g., mean, median, deviation, kurtosis etc.) and the geometrical properties of the encompassing ellipse (e.g., major and minor diameters and tilt) may be computed and used as features.

Table 1 provides a list of example synchronicity feature extracted parameters associated with Poincaré map analysis PM #1 as their corresponding description.

TABLE 1

| Parameter name | Description |
| --- | --- |
| dXDmj | Major diameter of an ellipse from Poincaré map PM#1 for the PSR/ECG "X" channel. |
| dXDmn | Minor diameter of an ellipse from Poincaré map PM#1 for the PSR/ECG "X" channel. |
| dZDmn | Minor diameter of an ellipse from Poincaré map analysis PM#1 on the PSR/ECG "Z" channel. |
| dYAlpha | Tilt angle, alpha, of the ellipse from Poincaré map analysis PM#1 on the PSR/ECG "Y" channel. |
| dZAlpha | Tilt angle, alpha, of an ellipse from Poincaré map analysis PM#1 on the PSR/ECG "Z" channel. |
| dXMean1 | Amplitude mean of the PSR/ECG "X" channel at the first intersection/crossover points of photoplethysmographic signals (e.g., in Poincaré map analysis PM#1). |
| dXStd1 | Standard deviation of the distribution of the PSR/ECG "X" channel triggered by the first crossover landmarks of photoplethysmographic signals (e.g., in Poincaré map analysis PM#1). |
| dXStd2 | Standard deviation of the distribution of the PSR/ECG "X" channel triggered by second crossover landmarks of photoplethysmographic signals (e.g., in Poincaré map analysis PM#1). |
| dYStd2 | Standard deviation of the distribution of the PSR/ECG "Y" channel data triggered at second crossover landmarks of photoplethysmographic signals (e.g., in Poincaré map analysis PM#1). |
| dYKurt2 | Kurtosis of distribution of the PSR/ECG "Y" channel data triggered at second crossover landmarks of photoplethysmographic signals (e.g., in Poincaré map analysis PM#1). |

TABLE 1-continued

| Parameter name | Description |
| --- | --- |
| dZKurt2 | Kurtosis of distribution of the PSR/ECG "Y" channel data triggered at second crossover landmarks of photoplethysmographic signals (e.g., in Poincaré map analysis PM#1). |
| dYMode2 | Mode of distribution of the PSR/ECG "Y" channel data triggered at second crossover landmarks of photoplethysmographic signals (e.g., in Poincaré map analysis PM#1). |
| dZMode2 | Mode of distribution of the PSR/ECG "Z" channel data triggered at the second crossover landmarks of photoplethysmographic signals (e.g., in Poincaré map analysis PM#1). |
| dZSkew1 | Kurtosis of distribution of the PSR/ECG "Z" channel data triggered at first crossovers of photoplethysmographic signals (e.g., in Poincaré map analysis PM#1). |
| dZSkew2 | Kurtosis of distribution of the PSR/ECG "Z" channel data triggered at second crossovers of photoplethysmographic signals (e.g., in Poincaré map analysis PM#1). |
| dYRelStdMAD2 | Relative difference between the standard deviation and median absolute deviation (MAD) of distribution of the PSR/ECG "Y" channel data triggered at second crossovers of photoplethysmographic signals (e.g., in Poincaré map analysis PM#1). |
| dZRelStdMAD1 | Relative difference between the standard deviation and median absolute deviation (MAD) of distribution of the PSR/ECG "Z" channel data triggered at first crossovers of photoplethysmographic signals (e.g., in Poincaré map analysis PM#1). |

Synchronicity Features Example PM #2

Figure 6A:
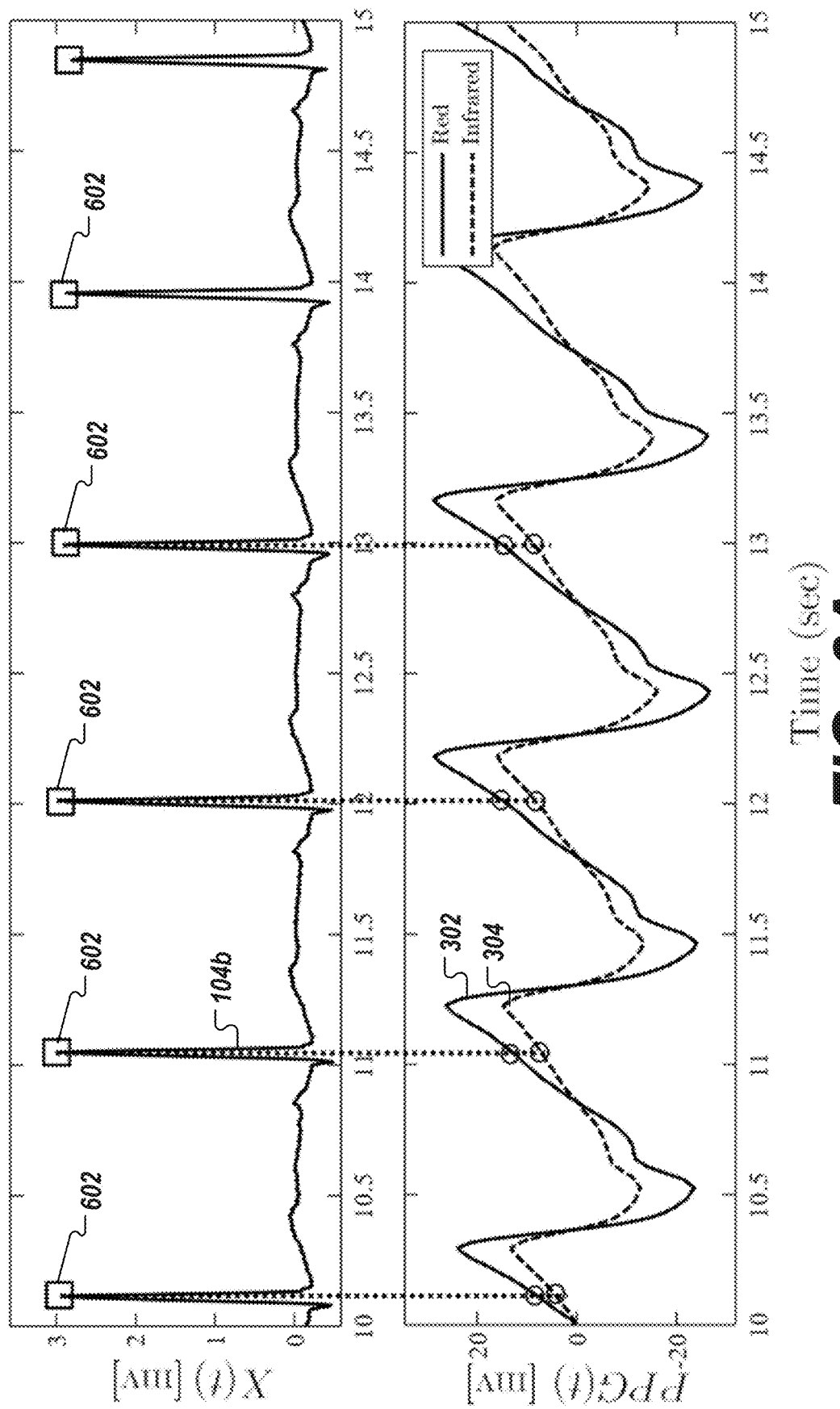
FIGS. 6A, 6B, and 6C illustrate another set of example dynamical properties of synchronicity between acquired photoplethysmographic and cardiac signals in accordance with an illustrative embodiment.
Figure 6B:
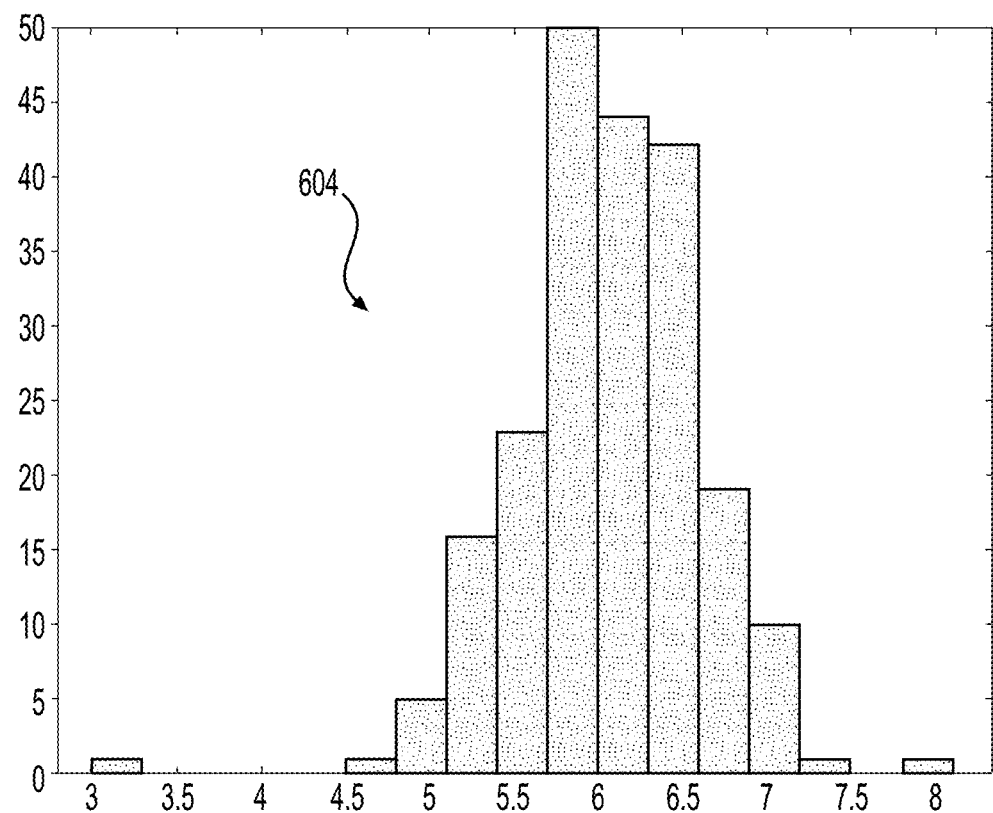
Figure 6C:
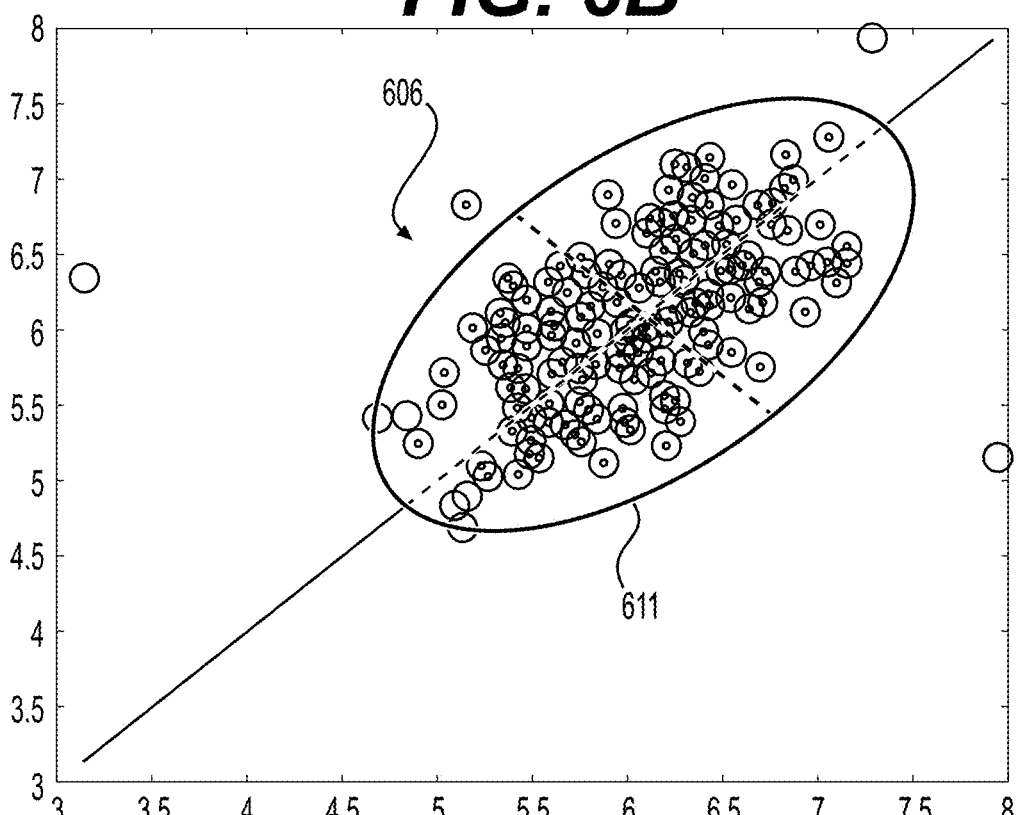

FIGS. 6A, 6B, and 6C illustrate another set of example dynamical properties of synchronicity between acquired photoplethysmographic signals and cardiac signals in accordance with an illustrative embodiment. In FIGS. 6A, 6B, and 6C, synchronicity is determined, via histogram/Poincaré map analysis, using landmarks in a cardiac signal.

FIG. 6A shows one channel of an acquired cardiac signal data set with respect to an acquired red photoplethysmographic signal 302 and infrared photoplethysmographic signal 304. The x-axis shows the time domain (in index count of the data set), and the y-axis shows the acquired amplitude of the signal in millivolts;

FIG. 6B shows a histogram 604 of the amplitude magnitude values of one of the photoplethysmographic signals at an assessed peak of the QRS waveform (also referred to as R-peak) of the cardiac signal. Here, the magnitude of the infrared photoplethysmographic signal is shown. In other embodiments, both amplitude magnitudes of the red and infrared photoplethysmographic signals are recorded and analyzed for statistical and geometric features. In FIG. 6B, the x-axis of the histogram shows signal amplitude (in mV) and the y-axis shows the frequency/count.

In some embodiments, the dynamical feature extraction module 118 is configured to generate a histogram and extract statistical properties, such as, but not limited to modes, scale, skewness, kurtosis, and mutual information, from the generated histogram, e.g., as discussed in relation to FIG. 5B.

FIG. 6C shows a Poincaré map 606 of amplitude magnitude values of the acquired infrared photoplethysmographic signal 304 at an assessed R-peak of the acquired cardiac signal. In FIG. 6C, the amplitude values of a photoplethysmographic signal at landmarks in a cardiac signal is plotted in pair (e.g., at a first time x−1 and a second time x in the x-axis and at the second time x and a third time x+1 in the y-axis).

Following the generation of the Poincaré map 606, the dynamical feature extraction module 118, in some embodiments, is configured to generate a geometric object from the data. In FIG. 6C, the dynamical feature extraction module 118 determines an ellipse 611 based on an ellipse fit operation of the data associated with a cluster (e.g., 510a). Based on the fitted ellipse, the dynamical feature extraction module 118, in some embodiments, is configured to determine geometric parameters such as length of semi axis "a" (514), semi axis "b" (516), length along a long axis (518), and length along a short axis (520), e.g., as described in relation to FIG. 5D. The dynamical feature extraction module 118, in some embodiments, may extract other parameters such as void area, surface area, porosity, perimeter length, density, among others.

Indeed, synchronicity between acquired raw photoplethysmographic signal and cardiac signal based on triggers defined in the cardiac signal may be used to assess for the presence, non-presence, severity, and/or localization of coronary artery disease, pulmonary hypertension, heart failure, among other diseases, conditions, and associated conditions.

In some embodiments, to generate Poincaré map 512, module 118 plots/generates a 2D pairs of points $[x_i, x_{i+1}]$ (e.g., $(x_1, x_2)$, $(x_2, x_3)$, etc.) against the points $[x_{+1}, x_i]$ (e.g., $(x_0, x_1)$, $(x_1, x_2)$) of the amplitude values of a given photoplethysmographic signal (e.g., the red or the infrared photoplethysmographic signal) at a landmark of a cardiac signal (e.g., at one of channel "x," "y," or "z").

Figure 6D:
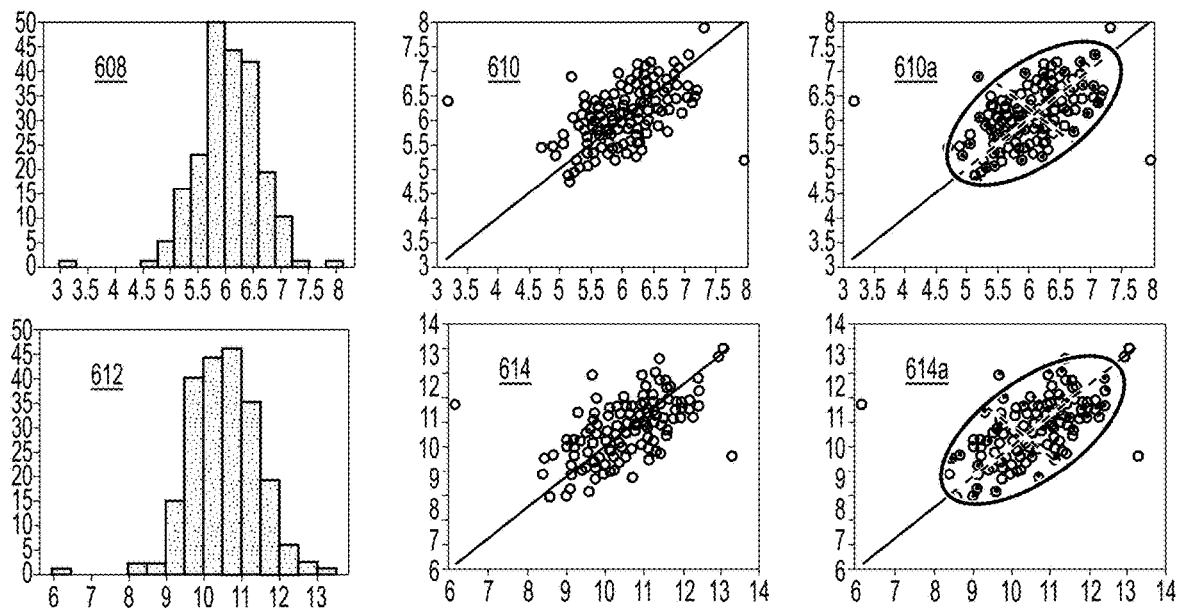
FIG. 6D shows histograms and Poincaré map results of a CAD-negative patient in accordance with an illustrative embodiment.

FIG. 6D shows histograms and Poincaré map results of a CAD-negative patient in accordance with an illustrative embodiment. Specifically, FIG. 6D shows a histogram 608 and Poincaré map 610 of a CAD-negative patient generated from amplitude magnitude values of an acquired red photoplethysmographic signal at R-peaks of one of an acquired cardiac signal 104b and histogram 612 and Poincaré map 614 generated from amplitude magnitude values of an acquired infrared photoplethysmographic signal at R-peaks of one of an acquired cardiac signal 104b. In the histograms 608, 612, the x-axis of the histogram shows signal amplitude (in mV), and the y-axis shows the frequency/count. In the Poincaré maps 610, 610a, 614, 614a, the x-axis and the y-axis each shows the amplitude values of a photoplethysmographic signal at landmarks in a cardiac signal as plotted in pair (e.g., at a first time x−1 and a second time x in the x-axis and at the second time x and a third time x+1 in the y-axis). Plotting can also be done with respect to index values denoted for a given data set.

Figure 6E:
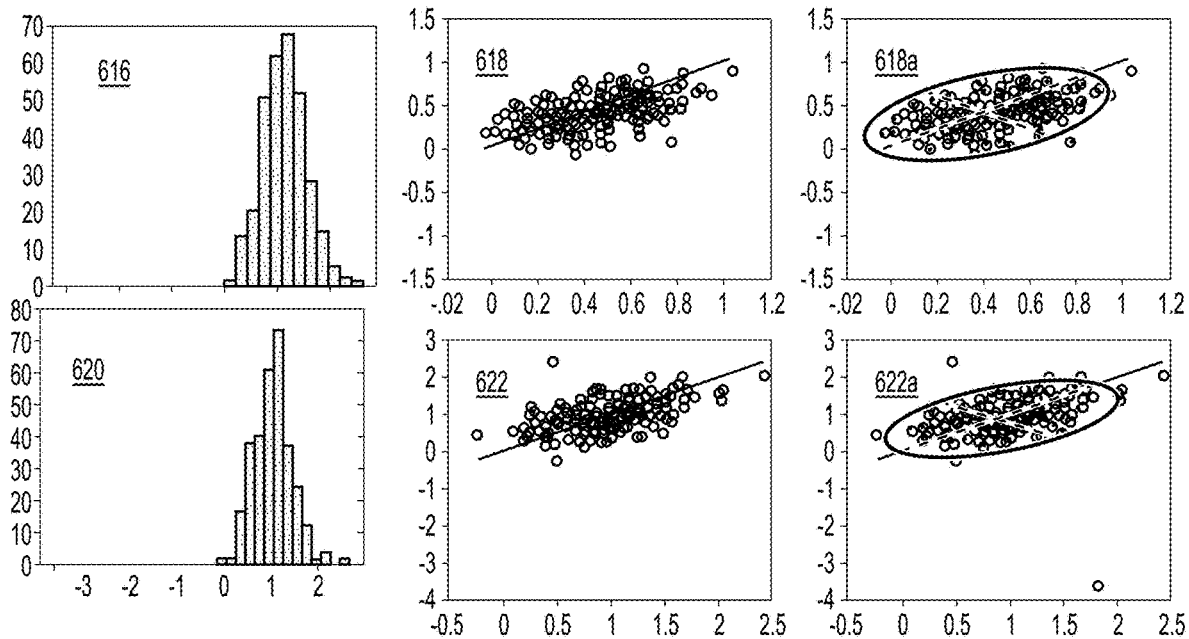
FIG. 6E shows histograms and Poincaré map results of a CAD-positive patient in accordance with an illustrative embodiment.

FIG. 6E shows histograms and Poincaré map results of a CAD-positive patient in accordance with an illustrative embodiment. Specifically, FIG. 6E shows histogram 616 and Poincaré map 618 of a CAD-positive patient generated from amplitude magnitude values of an acquired red photoplethysmographic signal at R-peaks of one of an acquired cardiac signal 104b and histogram 620 and Poincaré map 622 generated from amplitude magnitude values of an acquired infrared photoplethysmographic signal at R-peaks of one of an acquired cardiac signal 104b. In the histograms 616, 620, the x-axis of the histogram shows signal amplitude (in mV), and the y-axis shows the frequency/count. In the Poincaré maps 618, 618a, 622, 622a, the x-axis and the y-axis each shows the amplitude values of a photoplethysmographic signal at landmarks in a cardiac signal as plotted in pair (e.g., at a first time x−1 and a second time x in the x-axis and at the first time x and a third time x+1 in the y-axis). Plotting can also be done with respect to index values denoted for a given data set.

Table 2 provides a list of example synchronicity feature extracted parameters associated with Poincaré map analysis PM #2 as their corresponding description.

TABLE 2

| | |
|---|---|
| dDmjL | Major diameter of the ellipse in Poincaré map derived from the amplitude of the infrared photo-photoplethysmographic signal at R-peaks of a cardiac signal (e.g., per example Poincaré map analysis PM#2). |
| dDmjU | Major diameter of the ellipse in Poincaré map derived from the amplitude of the red photo-photoplethysmographic signal at R-peaks of a cardiac signal (e.g., per example Poincaré map analysis PM#2). |
| dDmnU | Minor diameter of the ellipse in Poincaré map derived from the amplitude of the red photo-photoplethysmographic signal at R-peak of a cardiac signal (e.g., per example Poincaré map analysis PM#2). |
| dAlphaL | Tilt angle, alpha, of the ellipse in Poincaré map derived from the amplitude of the infrared photo-photoplethysmographic signal at R-peak of a cardiac signal (e.g., per example Poincaré map analysis PM#2). |
| dAlphaU | Tilt angle, alpha, of the ellipse in Poincaré map derived from the amplitude of the red photo-photoplethysmographic signal at R-peak of a cardiac signal (e.g., per example Poincaré map analysis PM#2). |
| dKurtL | Kurtosis of a histogram of Poincaré map analysis "PM2" of the infrared photoplethysmographic signal. |
| dMeanL | Mean value of a histogram of Poincaré map analysis "PM2" of the infrared photoplethysmographic signal. |
| dMeanU | Mean value of a histogram of Poincaré map analysis PM#2 for the red photoplethysmographic signal. |
| dModeLP | Mode of the distribution (histogram) of Poincaré map analysis PM#2 for the infrared photoplethysmographic signal. |
| dModeUP | Mode of the distribution (histogram) of Poincaré map analysis PM#2 for the infrared photoplethysmographic signal. |
| dStdU | Standard deviation of a histogram of Poincaré map analysis PM#2 for the red photoplethysmographic signal. |

Synchronicity Features Example PM #3

Figure 7A:
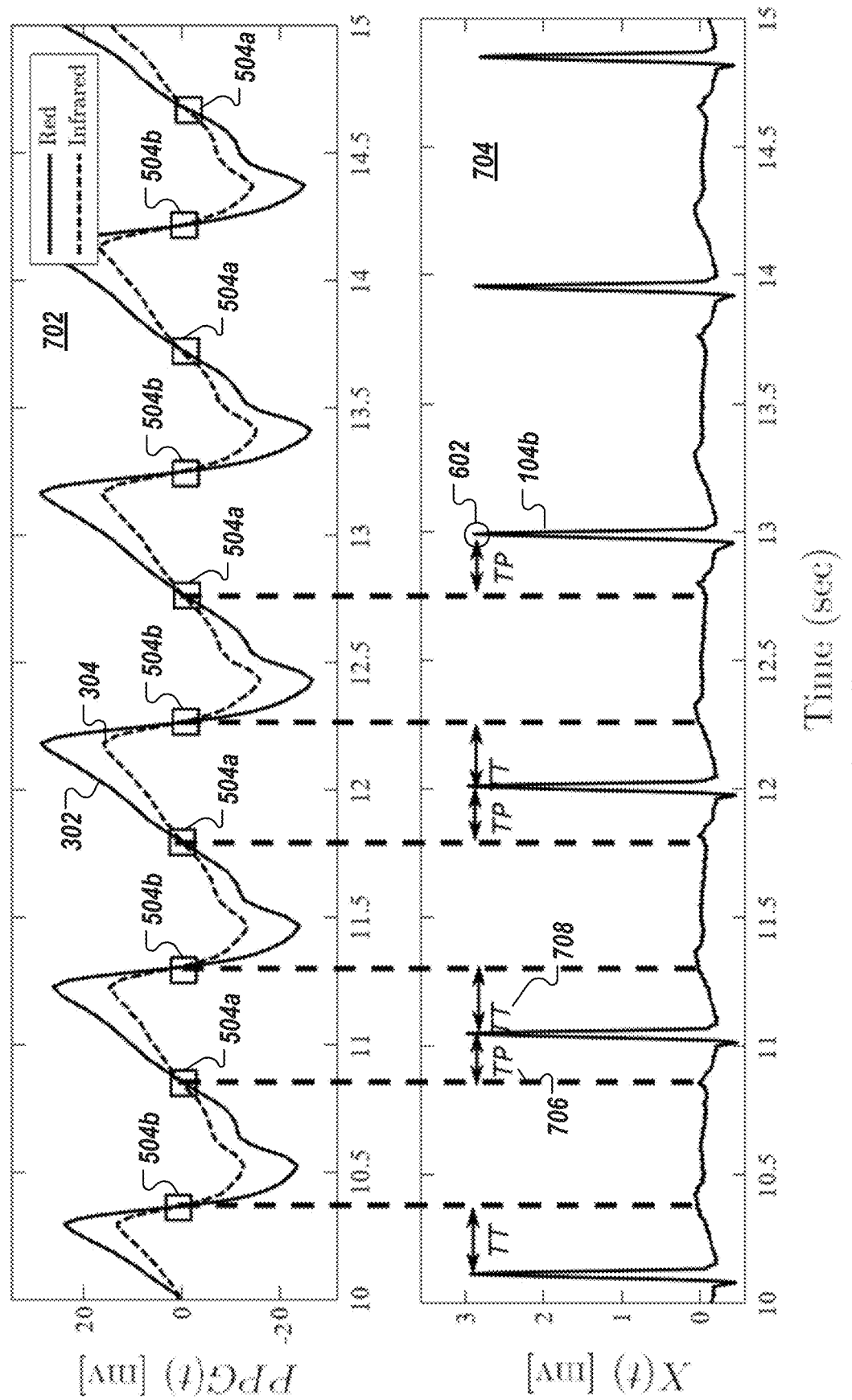
FIGS. 7A, 7B, and 7C illustrate yet another example dynamical properties of synchronicity between acquired photoplethysmographic and cardiac signals in accordance with an illustrative embodiment.
Figure 7B:
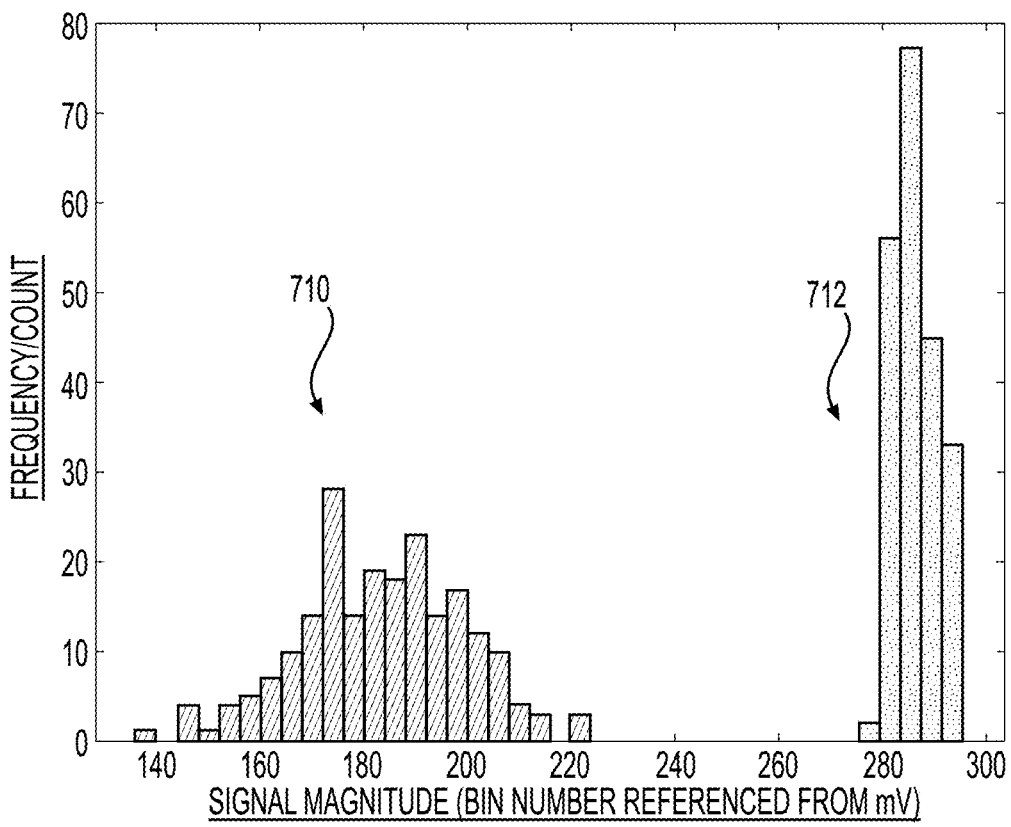
Figure 7C:
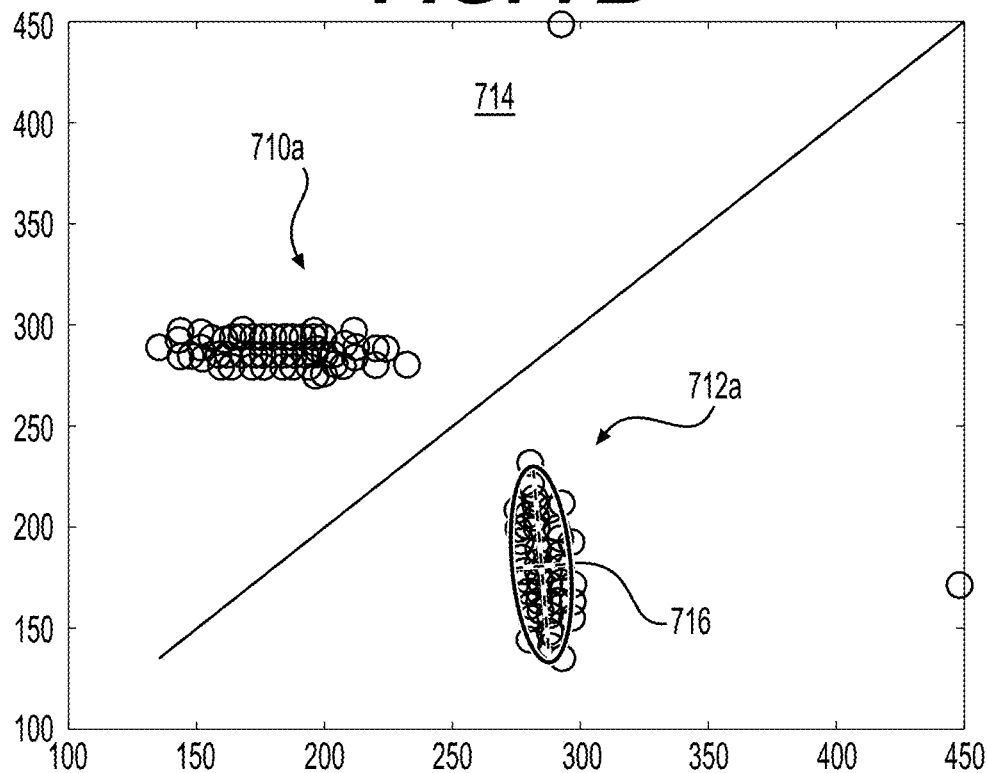

FIGS. 7A, 7B, and 7C illustrate yet another example dynamical properties of synchronicity between acquired photoplethysmographic signal and cardiac signals in accordance with an illustrative embodiment. In FIGS. 7A, 7B, and 7C, synchronicity is determined using, via histogram/Poincaré map analysis, phase relations between landmarks in one or more of the cardiac signal and in one or more of the photoplethysmographic signals.

Specifically, FIG. 7A shows, in a first plot 702, crossover landmarks 504a and 504b as described in relation to FIG. 5A are defined between a red photoplethysmographic signal 302 and an infrared photoplethysmographic signal 304. A second plot 704 shows crossover landmarks 504a and 504b in relation to one of the channels of the acquired cardiac signal 104b. Plot 704 further shows a phase difference R-peak 602 (shown as "TP" 706 and "TT" 708) of the cardiac signal 104b and the crossover landmarks 504a and 504b of the photoplethysmographic signals. The x-axis shows the time domain (in index count of the data set), and the y-axis shows the acquired amplitude of the signal in millivolts;

FIG. 7B shows a histogram of the distribution of phase relations between the cardiac signal 104b and the respective crossover landmarks 504a and 504b. Specifically, FIG. 7B shows distributions 710, 712 corresponding to phase relations between the R-peak of the cardiac signal and the first and second sets of crossover landmarks (504a, 504b). In FIG. 7B, the x-axis of the histogram shows signal amplitude (in bin number), and the y-axis shows the frequency/count.

In some embodiments, dynamical feature extraction module 118 is configured to generate a histogram (e.g., as generated per FIG. 5B) and extract statistical and geometric properties from the generated histogram. In some embodiments, the extracted histogram features include, for example, but not limited to, modes, standard deviation, skewness, kurtosis, and mutual information. The term "mode" as used herein refers to the set of data values that appear most often in a date set. The term "skewness" as used herein refers to a measure of the asymmetry of the probability distribution of the data set about its mean. The term "kurtosis" as used herein refers to the sharpness of the peak of a distribution curve.

FIG. 7C shows a Poincaré map 714 of phase relations between the cardiac signal 104b and the respective crossover landmarks 504a and 504b. In FIG. 7C, the time values of TP interval and TT intervals defined between the photoplethysmographic signals and the cardiac signals are plotted in pair (e.g., at a first time x−1 and a second time x in the x-axis and at the second time x and a third time x+1 in the y-axis).

In FIG. 7C, the amplitude values (e.g., in bits) of a photoplethysmographic signal at landmarks in a cardiac signal is plotted in pair (e.g., at a first time x−1 and a second time x in the x-axis and at the second time x and a third time x+1 in the y-axis).

That is, to generate the Poincaré map 714, the system plots/generates a 2D pairs of points $[x_i, x_{i+1}]$ (e.g., $(x_1, x_2)$, $(x_2, x_3)$ etc.) of the TP interval index/time against the points $[x_i, x_{i+1}]$ (e.g., $(x_1, x_2)$, $(x_2, x_3)$ etc.) of the TT interval index/time.

In some embodiments, dynamical feature extraction module 118 is configured to generate Poincaré map 714. Following the generation of Poincaré map 714, dynamical feature extraction module 118, in some embodiments, is configured to generate a geometric object from the map data. In FIG. 7C, in some embodiments, dynamical feature extraction module 118 determines an ellipse 716 based on an ellipse fit operation of the data associated with a cluster (e.g., 712a). Based on the fitted ellipse, the dynamical feature extraction module 118, in some embodiments, is configured to determine geometric parameters such as, but not limited to, length of semi axis "a" (514), semi axis "b" (516), length along a long axis (518), and length along a short axis (520) as shown in FIG. 5D.

The dynamical feature extraction module 118, in some embodiments, may extract other parameters such as void area, surface area, porosity, perimeter length, density, among others.

Figure 7D:
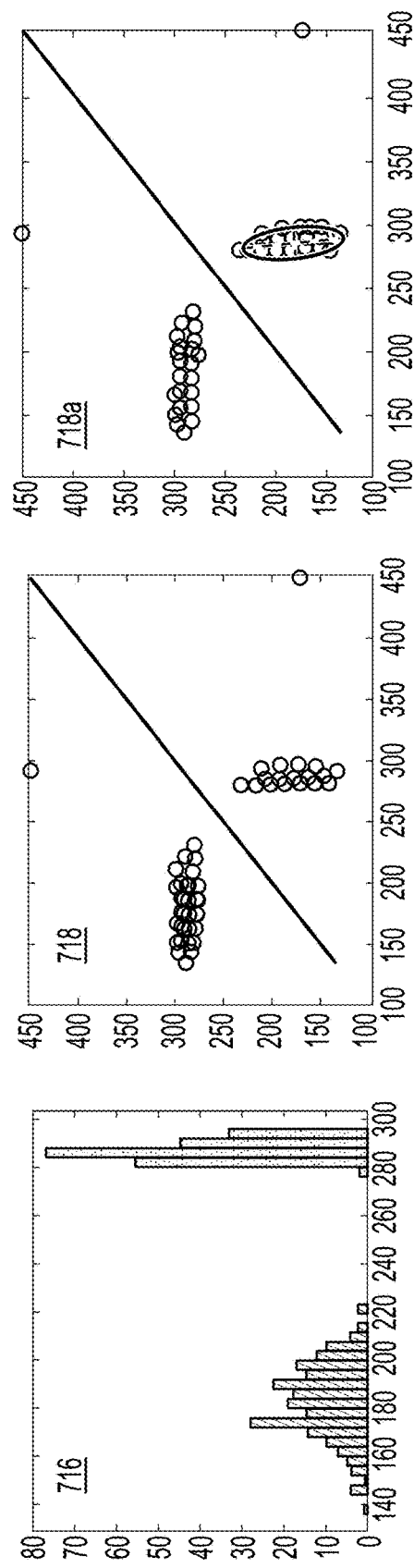
FIG. 7D shows histogram-map and Poincaré-map results of a CAD-negative patient in accordance with an illustrative embodiment.
Figure 7E:
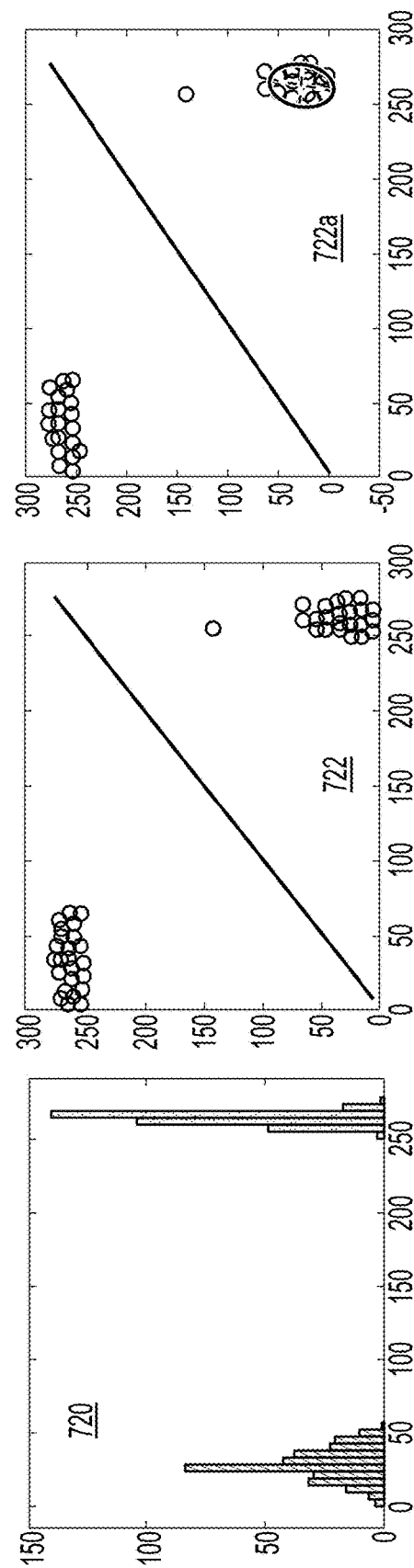
FIG. 7E shows histogram-map and Poincaré-map results of a CAD-positive patient in accordance with an illustrative embodiment.

Indeed, synchronicity between one or more acquired raw photoplethysmographic signals and one or more cardiac signals based on phase relations between landmarks in the photoplethysmographic signals and in the cardiac signal may be used to assess for the presence, non-presence, severity, and/or localization (where applicable) of coronary artery disease, pulmonary hypertension, heart failure, among other disease, conditions, and associated conditions. FIG. 7D shows an example Poincaré map of a data set acquired from a CAD-negative patient. FIG. 7E shows an example Poincaré map of a data set acquired from a CAD-positive patient.

FIG. 7D shows histogram- and Poincaré-map results of a CAD-negative patient in accordance with an illustrative embodiment. Specifically, FIG. 7D shows histogram 716 and Poincaré map 718 of a CAD-negative patient generated from phase relations (e.g., TP and TT) between an acquired infrared photoplethysmographic signal and R-peaks of one of an acquired cardiac signal 104b.

FIG. 7E shows histogram- and Poincaré-map results of a CAD-positive patient in accordance with an illustrative embodiment. Specifically, FIG. 7E shows histogram 720 and Poincaré map 722 of a CAD-positive patient generated from phase relations (e.g., based on TP and T intervals) between an acquired infrared photoplethysmographic signal and R-peaks of one of an acquired cardiac signal 104b. Poincaré maps 718a and 722a further shows fitted ellipses in respective plots 718 and 722.

FIGS. 7F, 7G, 7H, and 7I illustrate other example dynamical properties of synchronicity between acquired photoplethysmographic signal and cardiac signals in accordance with an illustrative embodiment. Specifically, FIG. 7F is a histogram showing the distribution of time intervals (for the time intervals as shown in FIG. 7A) between pre-defined landmarks in a photoplethysmographic signal and a cardiac signal for a healthy patient (i.e., CAD-negative patient), and FIG. 7G shows a Poincaré map of the same data along with an ellipse fit to geometrically characterize the data distribution. FIG. 7H is a histogram of showing the distribution of time intervals (for the time intervals as shown in FIG. 7A) between pre-defined landmarks in a photoplethysmographic signal and a cardiac signal for an unhealthy patient (i.e., CAD-positive patient), and FIG. 7I shows a corresponding Poincaré map and ellipse fit of the same.

Table 3 provides a list of example synchronicity feature extracted parameters associated with Poincaré map analysis PM #3 as their corresponding description.

Figure 8A:
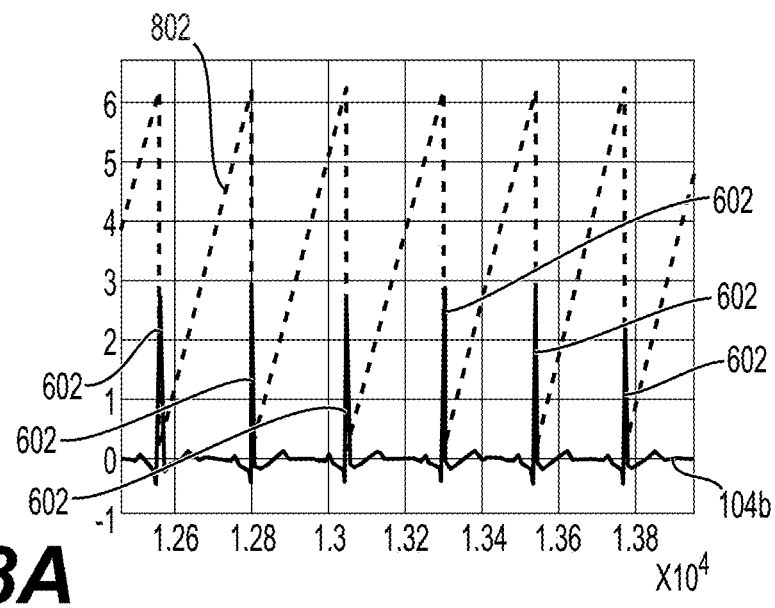
FIGS. 8A, 8B, and 8C illustrate another set of example dynamical properties of synchronicity between acquired photoplethysmographic and cardiac signals in accordance with an illustrative embodiment.

FIG. 8A shows the phase 802 of a cardiac signal 104b as defined in one full revolution/period from one R-peak (e.g., 602) to the next R-peak (e.g., 602) and is shown superimposed over the underlying cardiac signal data set used to generate the phase data.

Figure 8B:
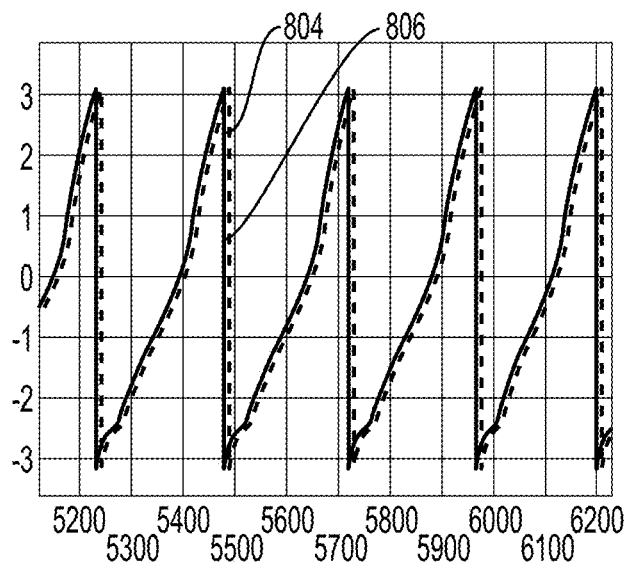

FIG. 8B shows the phases 804, 806 of the red and infrared photoplethysmographic signals as defined in one full revolution/period. The phase of the red photoplethysmographic signal and the infrared photoplethysmographic signal is shown from $-\pi$ to $\pi$ (y-axis) using the Hilbert transform; the x-axis is time (index count of the data set). As shown in FIG. 8B, the two phases of the red and infrared photoplethysmographic signals are coincident, signifying the two are synchronous.

Figure 8C:
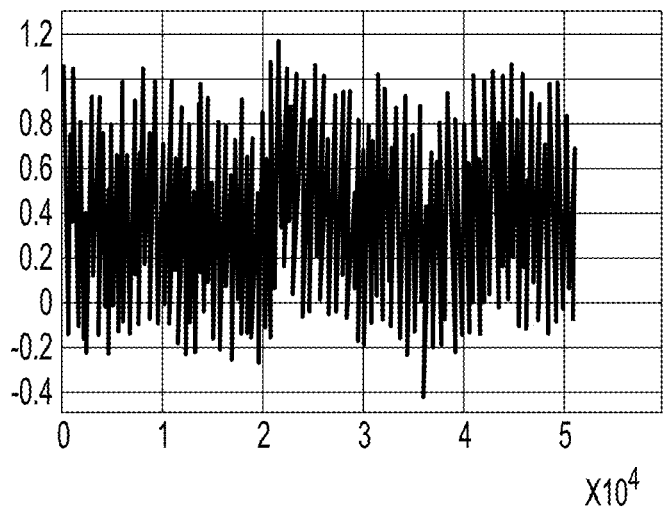

FIG. 8C shows a phase difference between the cardiac signal and one of the photoplethysmographic signals as determined by a difference of the period of a photoplethysmographic signal and the period of a cardiac signal. In FIG. 8C, the x-axis shows time (in index count of the data set), and the y-axis shows magnitude values of the calculated differences.

Indeed, synchronicity between acquired raw photoplethysmographic signals and cardiac signal based on phase differences between the cardiac signal and the photoplethysmographic signal(s) may be used to assess for the presence,

TABLE 3

| | |
|---|---|
| dDmjLUXR | Major diameter of the ellipse in a Poincaré map derived from differences in time intervals TT and TP between i) R-peaks in cardiac signals and ii) crossover landmarks between the acquired red and infrared photo-photoplethysmographic signals (e.g., per example Poincaré map analysis PM#3). |
| dDmnLUXR | Minor diameter of the ellipse in a Poincaré map derived from differences in time intervals TT and TP between i) R-peaks in cardiac signals and ii) crossover landmarks between the acquired red and infrared photo-photoplethysmographic signals (e.g., per example Poincaré map analysis PM#3). |
| dMeanLURP1 | Mean of TP time interval (time interval between R-peak of the PSR/ECG X channel and the first crossover landmarks between the red and infrared photo-photoplethysmographic signals in the Poincaré map analysis PM#3 landmarks). |
| dMeanLURP2 | Mean of TT time interval (time interval between R-peak of the PSR/ECG X channel and the second crossover landmarks between the red and infrared photo-photoplethysmographic signals in the Poincaré map example analysis PM#3 landmarks). |
| dModeLURP1 | Mode of TP time interval (time interval between R-peak of the PSR/ECG X channel and the first occurrence of the Poincaré map analysis PM#3 landmarks) for the red photoplethysmographic signal. |
| dModeLURP2 | Mode of TT time interval (time interval between R-peak of the PSR/ECG X channel and the second occurrence of the Poincaré map analysis PM#3 landmarks for the red photoplethysmographic signal). |
| dSkewLURP1 | Skew of TP time interval (time interval between R-peak of the PSR/ECG X channel and the first occurrence of the Poincaré map analysis PM#3 landmarks). |
| dStdLURP2 | Standard deviation of TT time interval (time interval between R-peak of the PSR/ECG X channel and the second occurrence of the Poincaré map analysis PM#3 landmarks). |
| dRelMeanMedDiffLURP1 | Ratio of mean -med/mean for two histograms: one for TP and one for TT, derived from Poincaré map analysis PM#3 (e.g., per FIG. 7B). |

Synchronicity Features Example #4

FIGS. 8A, 8B, and 8C illustrate another set of example dynamical properties of synchronicity between one or more acquired photoplethysmographic signals and one or more cardiac signals in accordance with an illustrative embodiment. In FIGS. 8A, 8B, and 8C, synchronicity is determined, via phase analysis, using landmarks in a cardiac signal.

non-presence, severity, and/or localization (where applicable) of coronary artery disease, pulmonary hypertension, heart failure, among other disease, conditions, and associated conditions.

Figure 8D:
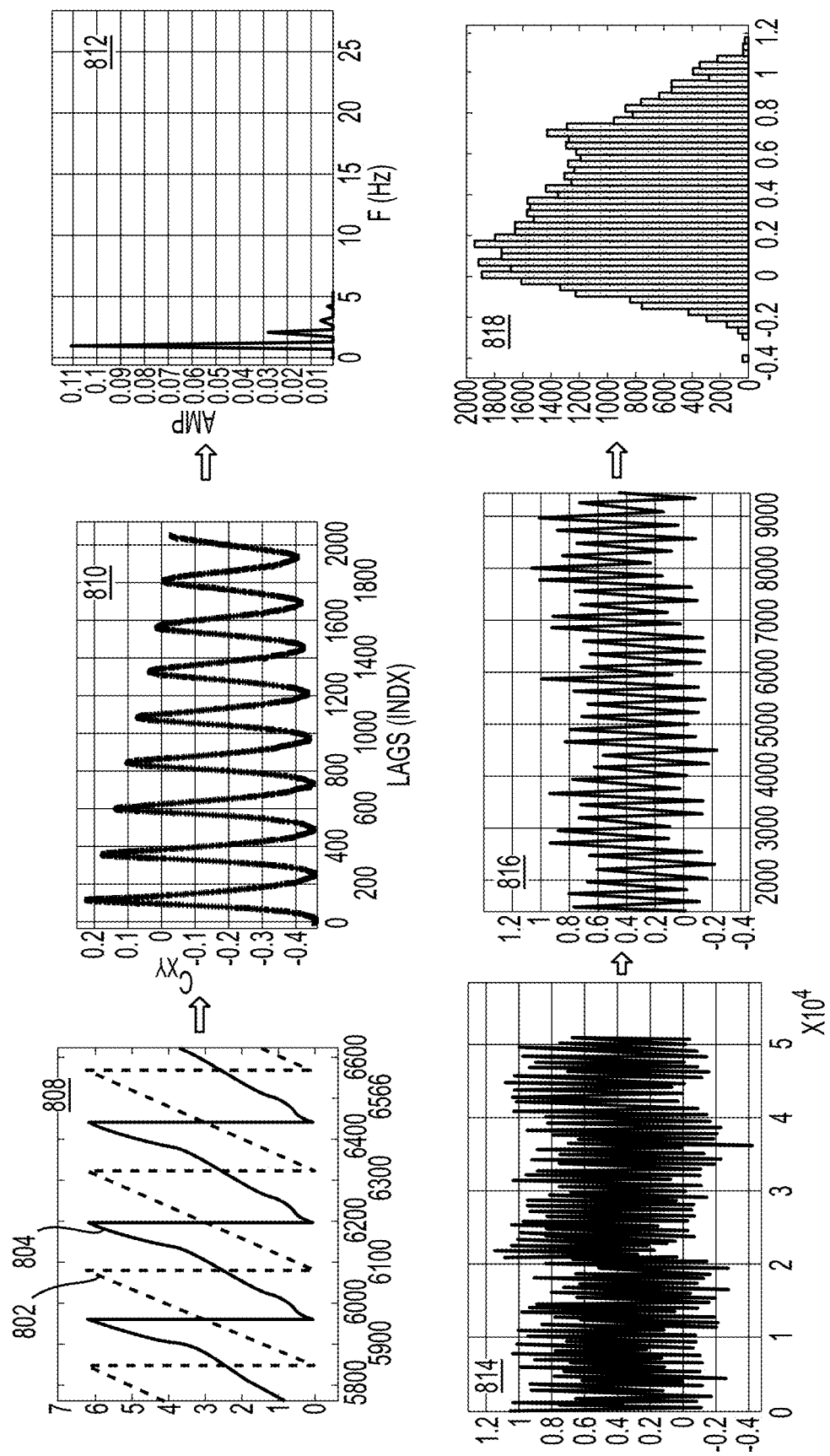
FIG. 8D shows phase difference analysis of a CAD-negative patient generated between an acquired infrared photoplethysmographic signal and an acquired cardiac signal in accordance with an illustrative embodiment.

FIG. 8D shows phase difference analysis of a CAD-negative patient (i.e., a patient having a negative diagnosis of coronary artery disease) generated between an acquired infrared photoplethysmographic signal 304 and an acquired cardiac signal 104b. Specifically, FIG. 8D shows plot 808 of the periods 802 of a cardiac signal and periods 804 of the infrared photoplethysmographic signal. In plot 808, the x-axis is time (in index count of the data set) and the y-axis shows the phase (in radian). Plot 810 shows a calculated lag between periods 802 and 804. In some embodiments, the time/index lag is calculated via cross correlation between the two signals. The lag is the time interval the one signal needs to be shifted with respect to the other in order to yield the maximum cross correlation (or the minimum cross correlation). In plot 810, the x-axis is time (in index count of the data set), and the y-axis shows the cross-correlation value (unitless).

Plot 812 shows a frequency analysis of the difference data of plot 810. In plot 812, the x-axis is the frequency (in Hz), and the y-axis is the relative amplitude of the signal. Plot 814 shows a difference between the infrared photoplethysmographic signal 304 and the cardiac signal 104b. In plot 814, the x-axis is time (in the index count of the data set). Plot 816 shows a filtered version of the difference data of plot 814. Plot 818 shows a histogram of the filtered difference data of plot 816. In the histogram 818, the x-axis of the histogram shows difference amplitude (in bins derived from the difference data), and the y-axis shows the frequency/count.

Figure 8E:
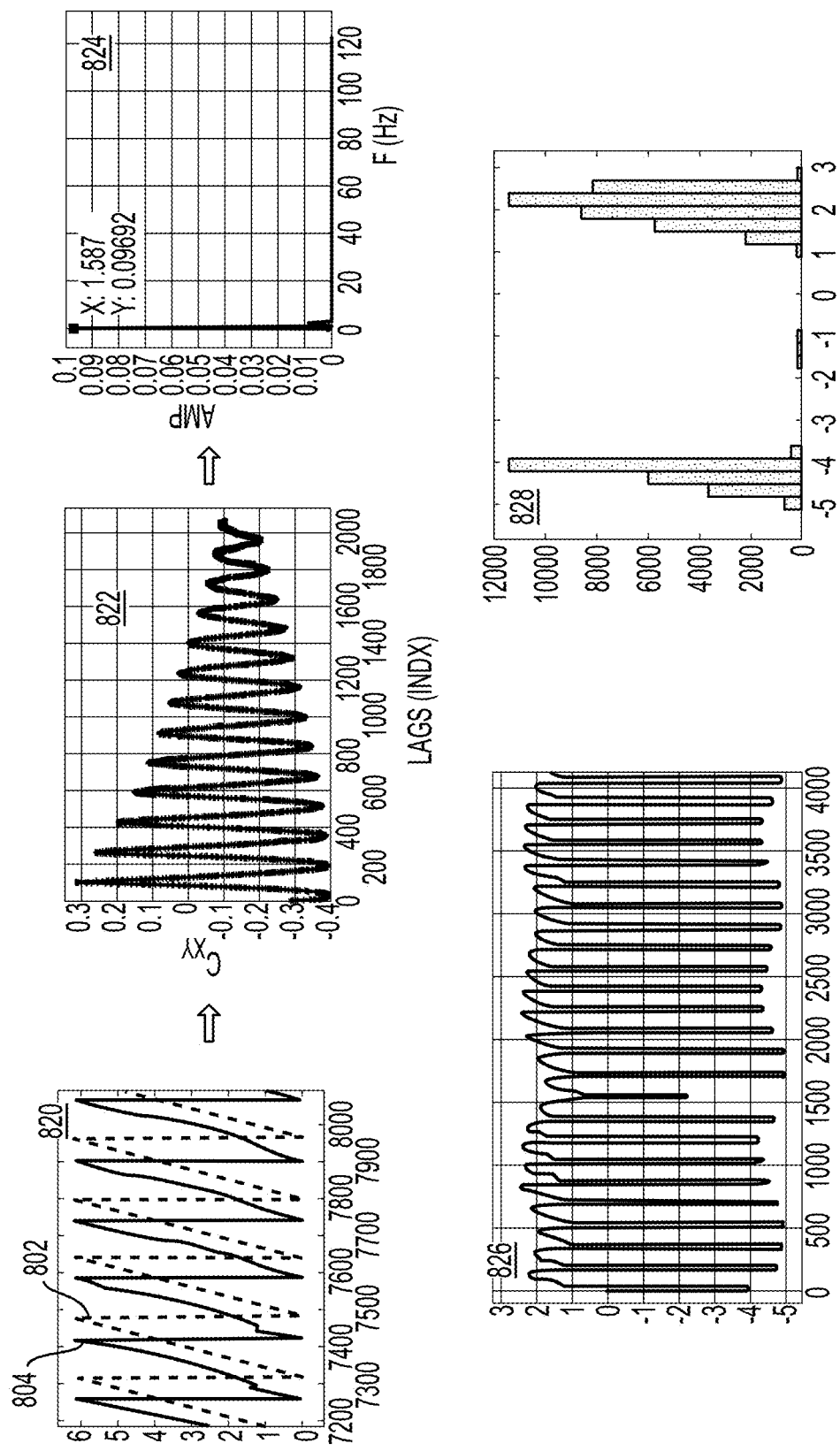
FIG. 8E shows a phase difference analysis of a CAD-positive patient generated between an acquired infrared photoplethysmographic signal and an acquired cardiac signal in accordance with an illustrative embodiment.

FIG. 8E shows a phase difference analysis of a CAD-positive patient generated between an acquired infrared photoplethysmographic signal 304 and an acquired cardiac signal 104b. Specifically, FIG. 8E shows plot 820 of the periods 802 of a cardiac signal and periods 804 of the infrared photoplethysmographic signal. In plot 820, the x-axis is time (in index count of the data set), and the y-axis shows the phase (in radian). Plot 822 shows a calculated lag between periods 802 and 804. Plot 824 shows a frequency analysis of the difference data of plot 822. In plot 822, the x-axis is time (in index count of the data set), and the y-axis shows the cross-correlation value (unitless). In plot 824, the x-axis is the frequency (in Hz), and the y-axis is the relative amplitude of the signal. Plot 826 shows a filtered difference between the infrared photoplethysmographic signal 304 and the cardiac signal 104b. In plot 826, the x-axis is time (in the index count of the data set). Plot 828 shows a histogram of the filtered difference data of plot 824. In the histogram 828, the x-axis of the histogram shows difference amplitude (in bins derived from the difference data), and the y-axis shows the frequency/count.

Table 4 provides a list of example synchronicity feature extracted parameters associated with Phase analysis #4 as their corresponding description.

TABLE 4

| | |
|---|---|
| dPhiDiffXL1Med | Median value of the phase difference distribution belonging to part 1 distribution after the phase difference between a photoplethysmographic signal and cardiac signal is split into two parts: part 1 with higher mean. |
| dPhiDiffXL2Med | Median value of the phase difference distribution belonging to part 1 distribution after the phase difference between a photoplethysmographic signal and cardiac signal are split into two parts: here, part 2 with lower mean. |
| dPhiDiffXL1Std | Standard deviation of phase difference distribution belonging to Part 2 distribution after the phase difference between a photoplethysmographic signal and a cardiac signal is split into two parts: here, part 1 with higher mean. |

TABLE 4-continued

| | |
|---|---|
| dPhiDiffXL2Std | Standard deviation of phase difference distribution belonging to Part 2 distribution after the phase difference between a photoplethysmographic signal and a cardiac signal is split into two parts: part 1 with higher mean and part 2 with lower mean. |
| dPhiDiffXLMean | Mean value of the whole distribution for phase difference distribution between a photoplethysmographic signal and a cardiac signal. |
| dPTT | Pulse transit time: time difference (lag) between the phase of the PSR/ECG X channel and phase of the infrared photoplethysmographic signal. |

Machine-Learning Based Classifier

Machine learning techniques predict outcomes based on sets of input data. For example, machine learning techniques are used to recognize patterns and images, supplement medical diagnoses, and so forth. Some machine learning techniques rely on a set of features generated using a training set of data (i.e., a data set of observations, in each of which an outcome to be predicted, is known), each of which represents some measurable aspect of observed data, to generate and tune one or more predictive models. For example, observed signals (e.g., cardiac, plethysmographic, or other biophysical signals from a number of subjects, alone or in any number of combinations) may be analyzed to collect frequency, average values, and other statistical information about these signals. A machine learning technique may use these features to generate and tune a model that classifies or relates these features to one or more conditions, such as some form of cardiovascular disease or condition, including, e.g., coronary artery disease, heart failure, pulmonary hypertension, etc., and then apply that model to data, such biophysical data of one or more humans, to detect and/or to gain an understanding of the presence, non-presence, severity of one or more diseases or conditions (such as described herein) that might otherwise not be detectable or understandable to the same degree. Conventionally, in the context of cardiovascular disease, these features are manually selected from conventional electrocardiographic signals and combined by data scientists working with domain experts.

Examples of embodiments of machine learning include, but are not limited to, decision trees, random forests, SVMs, neural networks, linear models, Gaussian processes, nearest neighbor, SVMs and Naïve Bayes. In some embodiments of the present disclosure, machine learning techniques may be implemented, e.g., as described in U.S. patent application Ser. No. 15/653,433, entitled "Discovering Novel Features to Use in Machine Learning Techniques, such as Machine Learning Techniques for Diagnosing Medical Conditions"; and U.S. patent application Ser. No. 15/653,431, entitled "Discovering Genomes to Use in Machine Learning Techniques"; each of which is incorporated by reference herein in its entirety.

Experimental Results and Other Embodiments

FIG. 9 shows experimental results from a study that indicates a clinical predictive value of certain dynamical features extracted from Poincaré and phase analysis of one or more photoplethysmographic signal(s) (red photoplethysmographic signals and infrared photoplethysmographic signals) and one or more cardiac signals; the value indicates the presence, non-presence, severity, and/or localization (where applicable) of a disease or abnormal condition, or an indication of one, in accordance with an illustrative embodiment.

In the study, candidate features were evaluated using a t-test, mutual information, or AUC. T-tests were conducted against a null-hypothesis of normal LVEDP and the null hypothesis of negative coronary artery disease. A t-test is a statistical test that can determine if there is a difference between two sample means from two populations with unknown variances. The output of the t-test is a dimensionless quantity known as a p-value. A small p-value (typically ≤0.05) indicates strong evidence against the null hypothesis. The study used random sampling with replacement (bootstrapping) to generate test sets.

Mutual information was conducted to assess the dependence of elevated or abnormal LVEDP or significant coronary artery disease on certain feature sets. Mutual information refers to an information theoretic measure of the mutual dependence between two random variables. MI is normalized by the number of bins, and the high and low MI are calculated as a high and a low of normMI/max(normMI-noise). A selected feature has a high that is greater than 1.0 and a low that is greater than 1.0.

Table 1 provides a description of each of the assessed synchronicity extracted parameters of FIG. 9 associated with Poincaré map analysis PM #1. Table 2 provides a description of each of the assessed synchronicity extracted parameters of FIG. 9 associated with Poincaré map analysis PM #2. Table 3 provides a description of each of the assessed synchronicity extracted parameters of FIG. 9 associated with Poincaré map analysis PM #3.

Table 4 provides a description of each of the assessed synchronicity extracted parameters of FIG. 9 associated with phase analysis example #4. The parameters may be configured as double precision variable.

Experimental Results for Features of Poincaré Map Analysis #1

As discussed above, Table 1 provides a description of each of the assessed synchronicity extracted parameters of FIG. 9 associated with Poincaré map analysis PM #1. FIG. 9 shows the various geometric and statistical features extracted from a Poincaré plot per Poincaré map analysis PM #1 as described herein has potential clinical relevance in predicting and/or estimating the presence, non-presence, severity, and/or localization (where applicable) of coronary artery disease and an elevated or abnormal LVEDP (which may indicate the presence, non-presence, and/or severity of a disease and/or condition).

Specifically, FIG. 9 (and reproduced in Tables 1-A and 1-B) shows that the major and minor diameters of a generated ellipse from Poincaré map PM #1 for the PSR/ECG "x" channel (shown as "dXDmj" and "dXDmn") has t-test p-value of 0.012 and 0.003, respectively, in predicting and/or estimating the presence, non-presence, and/or severity of an elevated or abnormal LVED (which may indicate the presence, non-presence, and/or severity of a disease or condition). Further, FIG. 9 shows that the minor diameter of a generated ellipse from Poincaré map PM #1 for the PSR/ECG "z" channel (shown as "dZDmn") has a t-test p-value of 0.037 in predicting and/or estimating the presence, non-presence, and/or severity of an elevated or abnormal LVED (which may indicate the presence, non-presence, and/or severity of a disease or condition). A small p-value (typically ≤0.05) indicates strong evidence against the null hypothesis (i.e., no presence of elevated or abnormal LVEDP; normal data set without elevated or abnormal LVEDP).

TABLE 1-A

| Feature Name | Disease State | Gender | t-test p-value |
|---|---|---|---|
| dXDmj | LVEDP | Female | 0.012 |

Description:
Major diameter of ellipse from Poincaré map PM#1 for the PSR/ECG "X" channel

TABLE 1-B

| Feature Name | Disease State | Gender | t-test p-value |
|---|---|---|---|
| dXDmn | LVEDP | Female | 0.003 |
| dZDmn | LVEDP | Both Genders | 0.037 |

Description:
Minor diameter of ellipse from Poincaré map PM#1 for the PSR/ECG "X" and "Z" channels Further, FIG. 9 (and reproduced in Table 1-C) shows that the tilt angle, alpha, of ellipses from Poincaré map analysis PM #1 on the PSR/ECG "y" and "z" channels (shown as "dYAlpha" and "dZAlpha") has a t-test p-value of 0.049 in predicting and/or estimating the presence, non-presence, localization (where applicable), and/or severity of coronary artery disease; a t-test p-value of 0.039 in predicting estimating the presence, non-presence, and/or severity of an elevated or abnormal LVED (which may indicate the presence, non-presence, and/or severity of a disease or condition). A small p-value (typically ≤0.05) indicates strong evidence against the null hypothesis (i.e., no presence of an elevated or abnormal LVEDP).

TABLE 1-C

| Feature Name | Disease State | Gender | t-test p-value |
|---|---|---|---|
| dYAlpha | CAD | Both Genders | 0.049 |
| dZAlpha | LVEDP | Male | 0.039 |

Description:
Tilt angle, alpha, of the ellipse from Poincaré map analysis PM#1 on the PSR/ECG "Y" and "Z" channels In addition, FIG. 9 (and reproduced in Table 1-D) shows that amplitude mean of PSR/ECG "x" channel at the first intersection/crossover points of photoplethysmographic signals (e.g., in Poincaré map analysis PM #1) (shown as "dXMean1") have respective t-test p-value of 0.00064 and an AUC value of 0.548; a t-test p-value of 0.011 and an AUC value of 0.518, in predicting and/or estimating the presence, non-presence, localization, and/or severity of coronary artery disease in certain populations. A small p-value (typically ≤0.05) indicates strong evidence against the null hypothesis (i.e., no presence of an elevated or abnormal LVEDP); an AUC greater than 0.5 has significance in indicating the presence of CAD (which is defined as having greater than 70% stenosis by angiography or less than 0.80 fraction-flow by flow wire).

TABLE 1-D

| Feature Name | Disease State | Gender | t-test p-value | ROC-AUC |
|---|---|---|---|---|
| dXMean1 | CAD | Female | 0.00064 | 0.548 |
| | CAD | Female | 0.011 | 0.518 |

Description:
Amplitude mean of PSR/ECG "X" channel at the first intersection/crossover points of photoplethysmographic signals (e.g., in Poincaré map analysis PM#1)

In addition, FIG. 9 (and reproduced in Tables 1-E, 1-F, and 1-G) shows that the standard deviation of the distribution of the PSR/ECG "x" channel triggered by the first and the second crossover landmarks of photoplethysmographic signals (e.g., in Poincaré map analysis PM #1) (shown as "dXStd1" and "dXStd2") has respective t-test p-value of 0.037 and 0.042 in predicting and/or estimating the presence, non-presence, and/or severity of an elevated or abnormal LVED (which may indicate the presence, non-presence, and/or severity of a disease or condition). Further, FIG. 9 shows that the standard deviation of the distribution of PSR/ECG "y" channel triggered by the second crossover landmarks of photoplethysmographic signals (e.g., in Poincaré map analysis PM #1) (shown as "dYStd2") has mutual information value of 1.143 in predicting/estimating the presence, non-presence, localization (where applicable), and/or severity of coronary artery disease. A mutual information of greater than 1.0 has significance; a p-value less than 0.05 has significance.

TABLE 1-E

| Feature Name | Disease State | Gender | t-test p-value |
|---|---|---|---|
| dXStd1 | LVEDP | Female | 0.037 |

Description:
Standard deviation of the distribution of the PSR/ECG "X" channel triggered by the first crossover landmarks of photoplethysmographic signals (e.g., in Poincaré map analysis PM#1)

TABLE 1-F

| Feature Name | Disease State | Gender | t-test p-value |
|---|---|---|---|
| dXStd2 | LVEDP | Both Genders | 0.042 |

Description:
Standard deviation of the distribution of the PSR/ECG "X" channel triggered by second crossover landmarks of photoplethysmographic signals (e.g., in Poincaré map analysis PM#1)

TABLE 1-G

| Feature Name | Disease State | Gender | Mutual Information |
|---|---|---|---|
| dYStd2 | CAD | Male | 1.143 |

Description:
Standard deviation of distribution of the PSR/ECG "Y" channel data triggered at second crossover landmarks of photoplethysmographic signals (e.g., in Poincaré map analysis PM#1)

Further, FIG. 9 (and reproduced in Table 1-H) shows that the kurtosis of the distribution of the PSR/ECG "y" channel triggered by the second crossover landmarks of photoplethysmographic signals (e.g., in Poincaré map analysis PM #1) (shown as "dYKurt2") has respective mutual information of 1.061 in p predicting and/or estimating the presence, non-presence, localization (where applicable), and/or severity of coronary artery disease. A mutual information of greater than 1.0 has significance.

TABLE 1-H

| Feature Name | Disease State | Gender | Mutual Information |
|---|---|---|---|
| dYKurt2 | CAD | Male | 1.061 |

Description:
Kurtosis of distribution of the PSR/ECG "Y" channel data triggered at second crossover landmarks of photoplethysmographic signals (e.g., in Poincaré map analysis PM#1)

Further, FIG. 9 (and reproduced in Table 1-I) shows that the kurtosis of the distribution of the PSR/ECG "z" channel triggered by the second crossover landmarks of photoplethysmographic signals (e.g., in Poincaré map analysis PM #1) (shown as "dZKurt2") have mutual information value of 1.076 in predicting and/or estimating the presence, non-presence, and/or severity of an elevated or abnormal LVED (which may indicate the presence, non-presence, and/or severity of a disease or condition); mutual information value of 1.192 in predicting and/or estimating the presence, non-presence, localization (where applicable), and/or severity of coronary artery disease. A mutual information of greater than 1.0 has significance.

TABLE 1-I

| Feature Name | Disease State | Gender | Mutual Information |
|---|---|---|---|
| dZKurt2 | LVEDP | Both Genders | 1.076 |
|  | CAD | Female | 1.192 |

Description:
Kurtosis of distribution of the PSR/ECG "Y" channel data triggered at second crossover landmarks of photoplethysmographic signals (e.g., in Poincaré map analysis PM#1)

Further, FIG. 9 (and reproduced in Table 1-J) shows that the mode of the distributions of the PSR/ECG "y" and "z" channels triggered by the second crossover landmarks of photoplethysmographic signals (e.g., in Poincaré map analysis PM #1) (shown as "dYMode2" and "dZMode2") have mutual information values of 1.104 and 1.036, respectively, in predicting and/or estimating the presence, non-presence, localization (where applicable), and/or severity of coronary artery disease. A mutual information of greater than 1.0 has significance.

TABLE 1-J

| Feature Name | Disease State | Gender | Mutual Information |
|---|---|---|---|
| dYMode2 | CAD | Both Genders | 1.104 |
| dZMode2 | CAD | Male | 1.036 |

Description:
Mode of distribution of the PSR/ECG "Y" and "Z" channel data triggered at the second crossover landmarks of photoplethysmographic signals (e.g., in Poincaré map analysis PM#1)

Further, FIG. 9 (and reproduced in Tables 1-K and 1-L) shows that the mode of the distributions of the PSR/ECG "z" channel triggered by the first and second crossover landmarks of photoplethysmographic signals (e.g., in Poincaré map analysis PM #1) (shown as "dZSkew1" and "dZSkew2") have mutual information values of 1.094 and 1.058, respectively, in predicting and/or estimating the presence, non-presence, localization (where applicable), and/or severity of coronary artery disease. A mutual information of greater than 1.0 has significance.

TABLE 1-K

| Feature Name | Disease State | Gender | Mutual Information |
|---|---|---|---|
| dZSkew1 | CAD | Female | 1.094 |

Description:
Kurtosis of distribution of the PSR/ECG "Z" channel data triggered at first crossover landmarks of photoplethysmographic signals (e.g., in Poincaré map analysis PM#1)

TABLE 1-L

| Feature Name | Disease State | Gender | Mutual Information |
|---|---|---|---|
| dZSkew2 | CAD | Both Gender | 1.058 |

Description:
Kurtosis of distribution of the PSR/ECG "Z" channel data triggered at second crossover landmarks of photoplethysmographic signals (e.g., in Poincaré map analysis PM#1)

In addition, FIG. 9 (and reproduced in Table 1-M) shows that the relative difference between the standard deviation and median absolute deviation (MAD) of distribution of the PSR/ECG "y" channel data triggered at second crossover landmarks of photoplethysmographic signals (e.g., in Poincaré map analysis PM #1) (shown as "dYRelStdMAD2") has a t-test p-values of 0.042 and a mutual information value of 1.048 in predicting and/or estimating the presence, non-presence, and/or severity of an elevated or abnormal LVED (which may indicate the presence, non-presence, and/or severity of a disease or condition).

TABLE 1-M

| Feature Name | Disease State | Gender | t-test p-value | Mutual Information |
|---|---|---|---|---|
| dYRelStdMAD2 | CAD | Male | 0.042 | 1.048 |

Description:
Relative difference between the standard deviation and median absolute deviation (MAD) of distribution of the PSR/ECG "Y" channel data triggered at second crossover landmarks of photoplethysmographic signals (e.g., in Poincaré map analysis PM#1)

Further, FIG. 9 (and reproduced in Table 1-N) shows that the relative difference between the standard deviation and median absolute deviation (MAD) of distribution of the PSR/ECG "z" channel data triggered at first crossover landmarks of photoplethysmographic signals (e.g., in Poincaré map analysis PM #1) (shown as "dZRelStdMAD1") has a t-test p-values of 0.041 in predicting and/or estimating the presence, non-presence, and/or severity of an elevated or abnormal LVED (which may indicate the presence, non-presence, and/or severity of a disease or condition). A p-value less than 0.05 has significance; a mutual information value greater than 1.0 has significance.

TABLE 1-N

| Feature Name | Disease State | Gender | t-test p-value |
|---|---|---|---|
| dZRelStdMAD1 | LVEDP | Female | 0.041 |

Description: Relative difference between the standard deviation and median absolute deviation (MAD) of distribution of the PSR/ECG "Z" channel data triggered at first crossover landmarks of photoplethysmographic signals (e.g., in Poincaré map analysis PM#1)

Experimental Results for Features of Poincaré Map Analysis #2

As discussed above, Table 2 provides a description of each of the assessed synchronicity extracted parameters of FIG. 9 associated with Poincaré map analysis PM #2. FIG. 9 shows the various geometric and statistical features extracted from a Poincaré plot per Poincaré map analysis PM #2 as described herein has potential clinical relevance in predicting the presence of coronary artery disease and an elevated or abnormal LVED (which may indicate the presence, non-presence, and/or severity of a disease or condition).

Specifically, FIG. 9 (and reproduced in Tables 2-A and 2-B) shows that the major diameters of a generated ellipses in Poincaré maps derived from the amplitude of infrared and red photo-photoplethysmographic signals at R-peaks of a cardiac signal (shown as "dDmjL" and "dDmjU") has t-test p-value of 0.031 and 0.007, respectively, in predicting and/or estimating the presence, non-presence, and/or severity of an elevated or abnormal LVED (which may indicate the presence, non-presence, and/or severity of a disease or condition). Further, FIG. 9 shows that the major diameter of a generated ellipses in Poincaré maps derived from the amplitude of the infrared photo-photoplethysmographic signal at R-peaks of a cardiac signal (shown as "dDmjL") has a t-test p-value of 0.035; mutual information value of 1.104; AUC of 0.502 in predicting and/or estimating the presence, non-presence, localization (where applicable), and/or severity of coronary artery disease.

TABLE 2-A

| Feature Name | Disease State | Gender | t-test p-value | Mutual Information | ROC-AUC |
|---|---|---|---|---|---|
| dDmjL | CAD | Female | 0.035 | 1.104 | 0.502 |
|  | LVEDP | Both Genders | 0.031 | n/s | n/s |

Description: Major diameter of the ellipse in Poincaré map derived from amplitude of infrared photo-photoplethysmographic signal at R-peaks of a cardiac signal (e.g., per example Poincaré map analysis PM#2)

TABLE 2-B

| Feature Name | Disease State | Gender | t-test p-value |
|---|---|---|---|
| dDmjU | LVEDP | Both Genders | 0.007 |

Description: Major diameter of the ellipse in Poincaré map derived from amplitude of red photo-photoplethysmographic signal at R-peaks of a cardiac signal (e.g., per example Poincaré map analysis PM#2)

Further, FIG. 9 (and reproduced in Table 2-C) shows that the minor diameters of a generated ellipses in Poincaré maps derived from the amplitude of the red photo-photoplethysmographic signal at R-peaks of a cardiac signal (shown as "dDmnU") has t-test p-value of 0.0380, respectively, in predicting and/or estimating the presence, non-presence, and/or severity of an elevated or abnormal LVED (which may indicate the presence, non-presence, and/or severity of a disease or condition). A mutual information of greater than 1.0 has significance; an AUC value greater than 1.0 has significance; a p-value less than 0.05 has significance.

TABLE 2-C

| Feature Name | Disease State | Gender | t-test p-value |
|---|---|---|---|
| dDmnU | LVEDP | Both Genders | 0.038 |

Description: Minor diameter of the ellipse in Poincaré map derived from amplitude of red photo-photoplethysmographic signal at R-peak of a cardiac signal (e.g., per example Poincaré map analysis PM#2)

In addition, FIG. 9 (and reproduced in Tables 2-D and 2-E) shows that the tilt angles, alpha, of the ellipses in Poincaré maps derived from the amplitude of the infrared and red photo-photoplethysmographic signals at R-peak of a cardiac signal (e.g., per example Poincaré map analysis PM #2) (shown as "dAlphaL" and "dAlphaU") have respective mutual information values of 1.043 and 1.03 in predicting and/or estimating the presence, non-presence, localization (where applicable), and/or severity of coronary artery disease. A mutual information of greater than 1.0 has significance.

TABLE 2-D

| Feature Name | Disease State | Gender | Mutual Information |
|---|---|---|---|
| dAlphaL | CAD | Female | 1.043 |

Description: Tilt angle, alpha, of the ellipse in Poincaré map derived from amplitude of the infrared photo-photoplethysmographic signal at R-peak of a cardiac signal (e.g., per example Poincaré map analysis PM#2)

TABLE 2-E

| Feature Name | Disease State | Gender | Mutual Information |
|---|---|---|---|
| dAlphaU | CAD | Both Genders | 1.03 |

Description: Tilt angle, alpha, of the ellipse in Poincaré map derived from of the amplitude red photo-photoplethysmographic signal at R-peak of a cardiac signal (e.g., per example Poincaré map analysis PM#2)

In addition, FIG. 9 (and reproduced in Table 2-F) shows that the kurtosis of the histogram of the infrared photoplethysmographic signal at R-peaks of a cardiac signal (shown as "dKurtL") has a mutual information value of 1.171 in predicting and/or estimating the presence, non-presence, localization (where applicable), and/or severity of an elevated or abnormal LVED (which may indicate the presence, non-presence, and/or severity of a disease or condition). A mutual information value of greater than 1.0 has significance.

TABLE 2-F

| Feature Name | Disease State | Gender | Mutual Information |
|---|---|---|---|
| dKurtL | LVEDP | Both Genders | 1.171 |

Description: Kurtosis of histogram of Poincaré map analysis "PM2" of infrared photoplethysmographic signal In addition, FIG. 9 (and reproduced in Tables 2-G and 2-H) shows that the mean of the histogram of the infrared and red photoplethysmographic signals at R-peaks of a cardiac signal (shown as "dMeanL" and "dMeanU") have respective t-test p-values of 0.033 and 0.003, respectively, in predicting and/or estimating the presence, non-presence, localization (where applicable), and/or severity of an elevated or abnormal LVED (which may indicate the presence, non-presence, and/or severity of a disease or condition). Further, FIG. 9 shows that the mean of the histogram of the infrared and red photoplethysmographic signals at R-peaks of a cardiac signal (shown as "dMeanL" and "dMeanU") have respective mutual information value of 1.012 and an AUC value of 0.516; mutual information value 1.091, in predicting and/or estimating the presence, non-presence, localization (where applicable), and/or severity of coronary artery disease. A mutual information of greater than 1.0 has significance; an AUC value greater than 1.0 has significance.

TABLE 2-G

| Feature Name | Disease State | Gender | t-test p-value | Mutual Information | ROC-AUC |
|---|---|---|---|---|---|
| dMeanL | CAD | Female | n/s | 1.012 | 0.516 |
| | LVEDP | Male | 0.033 | n/s | n/s |

Description: Mean value of histogram of Poincaré map analysis "PM2" of the infrared photoplethysmographic signals

TABLE 2-H

| Feature Name | Disease State | Gender | t-test p-value | Mutual Information |
|---|---|---|---|---|
| dMeanU | CAD | Female | n/s | 1.091 |
| | LVEDP | Both Genders | 0.003 | n/s |

Description: Mean value of histogram of Poincaré map analysis PM#2 for red photoplethysmographic signal In addition, FIG. 9 (and reproduced in Tables 2-1 and 2-J) shows that the mode of the histogram of the infrared and red photoplethysmographic signals at R-peaks of a cardiac signal (shown as "dModeLP" and "dModeUP") have respective t-test p-values of 0.024 and 0.004 in predicting and/or estimating the presence, non-presence, and/or severity of an elevated or abnormal LVED (which may indicate the presence, non-presence, and/or severity of a disease or condition). Further, FIG. 9 shows that the mode of the histogram of the infrared photoplethysmographic signal at R-peaks of a cardiac signal (shown as "dModeLP") has an AUC value of 0.507 in predicting the presence of coronary artery disease. An AUC value greater than 1.0 has significance; a p-value value less than 0.05 has significance.

TABLE 2-I

| Feature Name | Disease State | Gender | t-test p-value | ROC-AUC |
|---|---|---|---|---|
| dModeLP | CAD | Both Genders | n/s | 0.507 |
| | LVEDP | Both Genders | 0.024 | n/s |

Description: Mode of the distribution (histogram) of Poincaré map analysis PM#2 for the infrared photoplethysmographic signal

TABLE 2-J

| Feature Name | Disease State | Gender | t-test p-value |
|---|---|---|---|
| dModeUP | LVEDP | Both Genders | 0.004 |

Description: Mode of the distribution (histogram) of Poincaré map analysis PM#2 for the infrared photoplethysmographic signal In addition, FIG. 9 (and reproduced in Table 2-K) shows that the standard deviation of the histogram of the red photoplethysmographic signal at R-peaks of a cardiac signal (shown as "dStdU") has an AUC value of 0.511 in predicting and/or estimating the presence, non-presence, localization (where applicable), and/or severity of coronary artery disease. An AUC value greater than 1.0 has significance.

TABLE 2-K

| Feature Name | Disease State | Gender | ROC-AUC |
|---|---|---|---|
| dStdU | CAD | Female | 0.511 |

Description: Standard deviation of histogram of Poincaré map analysis PM#2 for the red photoplethysmographic signal Experimental Results for Features of Poincaré Map Analysis #3

As discussed above, Table 3 provides a description of each of the assessed synchronicity extracted parameters of FIG. 9 associated with Poincaré map analysis PM #3. FIG. 9 shows the various geometric and statistical features extracted from a Poincaré plot per Poincaré map analysis PM #3 as described herein has potential clinical relevance in predicting and/or estimating the presence, non-presence, localization (where applicable), and/or severity of coronary artery disease and an elevated or abnormal LVED (which may indicate the presence, non-presence, and/or severity of a disease or condition).

Specifically, FIG. 9 (and reproduced in Tables 3-A and 3-B) shows that the major diameters of a generated ellipses in Poincaré maps derived from differences in time intervals TT and TP between i) R-peaks in cardiac signals and ii) crossover landmarks between the acquired red and infrared photo-photoplethysmographic signals (shown as "dDmjLUXR") has an AUC value of 0.501, in predicting and/or estimating the presence, non-presence, localization (where applicable), and/or severity of coronary artery disease. Further, FIG. 9 shows that the minor diameters of a generated ellipses in Poincaré maps derived from differences in time intervals TT and TP between i) R-peaks in cardiac signals and ii) crossover landmarks between the acquired red and infrared photo-photoplethysmographic signals (shown as "dDmLUXR") has a t-test p-value of 0.02, in predicting and/or estimating the presence, non-presence, localization (where applicable), and/or severity of an elevated or abnormal LVED (which may indicate the presence, non-presence, and/or severity of a disease or condition). A p-value less than 0.05 has significance; an AUC value greater than 0.5 has significance.

TABLE 3-A

| Feature Name | Disease State | Gender | ROC-AUC |
|---|---|---|---|
| dDmjLUXR | CAD | Both Genders | 0.501 |

Description: Major diameter of the ellipse in Poincaré map derived from differences in time intervals TT and TP between i) R-peaks in cardiac signals and ii) crossover landmarks between the acquired red and infrared photo-photoplethysmographic signals (e.g., per example Poincaré map analysis PM#3)

TABLE 3-B

| Feature Name | Disease State | Gender | t-test p-value |
|---|---|---|---|
| dDmnLUXR | LVEDP | Female | 0.02 |

Description: Minor diameter of the ellipse in Poincaré map derived from differences in time intervals TT and TP between i) R- peaks in cardiac signals and ii) crossover landmarks between the acquired red and infrared photo-photoplethysmographic signals (e.g., per example Poincaré map analysis PM#3)

In addition, FIG. 9 (and reproduced in Tables 3-C and 3-D) shows that the means of TP and TT time intervals (i.e., the time interval between R-peak of the PSR/ECG "x" channel and the respective first and second crossover landmarks between the acquired red and infrared photo-photoplethysmographic signals) (shown as "dMeanLURP1" and "dMeanLURP2") have a t-test p-value of 0.013 and 0.02, respectively, in predicting and/or estimating the presence, non-presence, localization (where applicable), and/or severity of an elevated or abnormal LVED (which may indicate the presence, non-presence, and/or severity of a disease or condition).

TABLE 3-C

| Feature Name | Disease State | Gender | t-test p-value |
|---|---|---|---|
| dMeanLURP1 | LVEDP | Both Genders | 0.013 |

Description: Mean of TP time interval (time interval between R-peak of the PSR/ECG X channel and the first crossover landmarks between the red and infrared photo- photoplethysmographic signals in the Poincaré map analysis PM#3 landmarks)

TABLE 3-D

| Feature Name | Disease State | Gender | t-test p-value |
|---|---|---|---|
| dMeanLURP2 | LVEDP | Male | 0.02 |

Description: Mean of TT time interval (the time interval between R-peak of the PSR/ECG X channel and the second crossover landmarks between the red and infrared photo-photoplethysmographic signals in the Poincaré map example analysis PM#3 landmarks)

In addition, FIG. 9 (and reproduced in Tables 3-E and 3-F) shows that the modes of TP and TT time intervals (i.e., the time interval between R-peak of the PSR/ECG "x" channel and the respective first and second crossover landmarks between the acquired red and infrared photo-photoplethysmographic signals) (shown as "dModeLURP1" and "dModeLURP2") have a t-test p-value of 0.013 and 0.028, respectively, in predicting and/or estimating the presence, non-presence, localization (where applicable), and/or severity of an elevated or abnormal LVED (which may indicate the presence, non-presence, and/or severity of a disease or condition).

TABLE 3-E

| Feature Name | Disease State | Gender | t-test p-value |
|---|---|---|---|
| dModeLURP1 | LVEDP | Both Genders | 0.013 |

Description: Mode of TP time interval (the time interval between R-peak of the PSR/ECG X channel and the first occurrence of the Poincaré map analysis PM#3 landmarks) for the red photoplethysmographic signal

TABLE 3-F

| Feature Name | Disease State | Gender | t-test p-value |
|---|---|---|---|
| dModeLURP2 | LVEDP | Male | 0.028 |

Description: Mode of TT time interval (the time interval between R-peak of the PSR/ECG X channel and the second occurrence of the Poincaré map analysis PM#3 landmarks for the red photoplethysmographic signal)

In addition, FIG. 9 (and reproduced in Table 3-G) shows that the skew of TP time interval (i.e., the time interval between R-peak of the PSR/ECG "x" channel and the first crossover landmarks between the acquired red and infrared photo-photoplethysmographic signals) (shown as "dSkewLURP1" has a t-test p-value of 0.034 in predicting and/or estimating the presence, non-presence, localization (where applicable), and/or severity of presence of coronary artery disease.

TABLE 3-G

| Feature Name | Disease State | Gender | t-test p-value |
|---|---|---|---|
| dSkewLURP1 | CAD | Both Genders | 0.034 |

Description: Skew of TP time interval (the time interval between R-peak of the PSR/ECG X channel and the first occurrence of the Poincaré map analysis PM#3 landmarks)

In addition, FIG. 9 (and reproduced in Table 3-H) shows that the standard deviation of TT time interval (time interval between R-peak of the PSR/ECG X channel and the second occurrence of the Poincaré map analysis PM #3 landmarks) (shown as "dStdLURP2") has a mutual information value of 1.486 and an AUC value of 0.541 in predicting and/or estimating the presence, non-presence, localization (where applicable), and/or severity of presence of coronary artery disease.

TABLE 3-H

| Feature Name | Disease State | Gender | Mutual Information | ROC-AUC |
|---|---|---|---|---|
| dStdLURP2 | CAD | Both Genders | 1.486 | 0.541 |

Description: Standard deviation of TT time interval (the time interval between R-peak of the PSR/ECG X channel and the second occurrence of the Poincaré map analysis PM#3 landmarks)

In addition, FIG. 9 (and reproduced in Table 3-I) shows that the standard deviation of TT time interval (time interval between R-peak of the PSR/ECG "x" channel and the second crossover landmark between the acquired red and infrared photo-photoplethysmographic signals) (shown as "dRelMeanMedDiffLURP1") has an AUC value of 0.5 in predicting and/or estimating the presence, non-presence, localization (where applicable), and/or severity of the presence of coronary artery disease.

TABLE 3-I

| Feature Name | Disease State | Gender | ROC-AUC |
|---|---|---|---|
| dRelMeanMedDiffLURP1 | CAD | Both Genders | 0.5 |

Description:
Ratio of mean-med/mean for two histograms: one for TP and one for TT, derived from Poincaré map analysis PM#3 (e.g., per FIG. 7B).

Experimental Results for Features of Phase Analysis #4

As discussed above, Table 4 provides a description of each of the assessed synchronicity extracted parameters of FIG. 9 associated with phase analysis example #4. FIG. 9 also shows the various geometric and statistical features extracted from phase analysis #4 as described herein has potential clinical relevance in predicting and/or estimating the presence, non-presence, localization (where applicable), and/or severity of coronary artery disease and an elevated or abnormal LVED (which may indicate the presence, non-presence, and/or severity of a disease or condition).

Specifically, FIG. 9 (and reproduced in Table 4-A) shows that the median values of the phase difference distribution belonging to the first distribution after the phase difference between a photoplethysmographic signal and cardiac signal are split into two parts: part 1 with higher mean and part 2 with lower mean (shown as "dPhiDiffXL1Med") has a t-test p-value of 0.015 in predicting and/or estimating the presence, non-presence, localization (where applicable), and/or severity of coronary artery disease. A p-value less than 0.05 has significance.

TABLE 4-A

| Feature Name | Disease State | Gender | t-test p-value |
|---|---|---|---|
| dPhiDiffXL1Med | CAD | Both Genders | 0.015 |

Description:
Median value of the phase difference distribution belonging to the part 1 distribution after the phase difference between a photoplethysmographic signal and cardiac signal is split into two parts: part 1 with higher mean.

In addition, FIG. 9 (and reproduced in Table 4-B) shows that the standard deviation of the phase difference distribution belonging to the second distribution after the phase difference between a photoplethysmographic signal and cardiac signal is split into two parts: part 1 with higher mean and part 2 with lower mean (shown as "dPhiDiffXL2Std"), has an AUC value of 0.502 of predicting and/or estimating the presence, non-presence, localization (where applicable), and/or severity of coronary artery disease. An AUC greater than 0.5 has significance.

TABLE 4-B

| Feature Name | Disease State | Gender | ROC-AUC |
|---|---|---|---|
| dPhiDiffXL2Std | CAD | Male | 0.502 |

Description:
Standard deviation of the phase difference distribution belonging to Part 2 distribution after the phase difference between a photoplethysmographic signal and a cardiac signal is split into two parts: here, part 2 with lower mean.

In addition, FIG. 9 (and reproduced in Table 4-C) shows that the mean of the phase difference distribution between a photoplethysmographic signal and cardiac signal (shown as "dPhiDiffXLMean") has a t-test p-value of 0.26 in predicting and/or estimating the presence, non-presence, localization (where applicable), and/or severity of coronary artery disease. A p-value less than 0.05 has significance.

TABLE 4-C

| Feature Name | Disease State | Gender | t-test p-value |
|---|---|---|---|
| dPhiDiffXLMean | CAD | Both Genders | 0.026 |

Description:
Mean value of the whole distribution for the phase difference distribution between a photoplethysmographic signal and a cardiac signal In addition, FIG. 9 (and reproduced in Table 4-D) shows that the pulse transit time (i.e., the time difference (lag) between the phase of the PSR/ECG "x" channel and phase of the infrared photoplethysmographic signal) (shown as "dPTT") has a t-test p-value of 0.045 in predicting and/or estimating the presence, non-presence, localization (where applicable), and/or severity of an elevated or abnormal LVED (which may indicate the presence, non-presence, and/or severity of a disease or condition). A p-value less than 0.05 has significance.

TABLE 4-D

| Feature Name | Disease State | Gender | t-test p-value |
|---|---|---|---|
| dPTT | LVEDP | Female | 0.045 |

Description:
Pulse transit time: the time difference (lag) between the phase of the PSR/ECG X channel and phase of the infrared photoplethysmographic signal Coronary Artery Disease—Learning Algorithm Development Study A "Coronary Artery Disease—Learning Algorithm Development" (CADLAD) study was untaken that acquired photoplethysmographic signals and cardiac signals to support the development and testing of the machine-learned algorithms.

In the study, paired clinical data were used to guide the design and development of the pre-processing, feature extraction, and the machine learning phase of the development. That is, the collected clinical study data are split into cohorts: a training cohort, a validation cohort, and a verification cohort. In the study, each acquired data set is first pre-processed to clean and normalize the data. Following the pre-processing processes, a set of features are extracted from the signals in which each set of features is paired with a representation of the true condition—for example, the binary classification of the presence or absence of significant CAD or the scored classification of the presence of significant CAD in a given coronary artery.

The assessment system (e.g., 114, 114a, 114b), in some embodiments, automatically and iteratively explores combinations of features in various functional permutations with the aim of finding those combinations which can successfully match a prediction based on the features. To avoid overfitting of the solutions to the training data, the validation set is used as a comparator. Once candidate predictors have been developed, they are then manually applied to a verification data set to assess the predictor performance against data that has not been used at all to generate the predictor. Provided that the data sets are sufficiently large, the performance of a selected predictor against the verification set will be close to the performance of that predictor against new data.

The study also developed and evaluated machine learning-based predictive models that employ nonlinear dynamics and chaos for extracting physically meaningful and significant features from the cardiac biopotential and photoplethysmographic signal data. Traditional features based on linear characterizations of the signals are not capable of detecting more complex and nonlinear patterns hidden in the signals. In the study, by employing nonlinear dynamics, three categories of features were developed: (i) features based on the dynamics of the cardiac system represented by biopotential signal, (ii) features based on the dynamics represented by the PPG signals and (iii) features characterizing the synchronicity between the two dynamics.

For the first two sets, invariant measures of the dynamics such as Lyapunov exponent (LE), fractal dimension (D2) and rate of entropy (K2) were computed. Lyapunov exponent is a global measure that characterizes the strength of the exponential divergence [30]. For chaotic systems, the maximum Lyapunov exponent is a positive number which indicates that the system has less memory of the past. For a given dynamical system, as the Lyapunov exponent value becomes larger, the time horizon over which the past information can be used to predict the future becomes shorter. Entropy (KS) (or Kolmogorov Sinai entropy K2 [31, 32]) represents the rate of change of entropy with time. Fractal dimension (D2) characterizes the topological property of an attractor in phase space and can be used to reveal more about the dynamics in combining the geometric information of the attractor (fractality) and how the dynamics evolve on it [33]. An example of an attractor of the acquired cardiac and photoplethysmographic signals are shown in FIGS. 4A and 4B.

Nonlinear dynamics and chaos theory systematically can be used to explain the complexity of linear system systems and provides tools to quantitatively analyze their behavior [19]. Linear systems can generate responses which can grow/decay exponentially or oscillate periodically or a combination thereof in which any irregular pattern in the response may be ascribed to irregularity or randomness in the inputs to these systems. Linear systems are a simplification of reality, and most dynamical systems, whether natural or man-made, are inherently nonlinear, which can produce complex irregular behavior even without any source of randomness. These behaviors are often called deterministic chaos. Nonlinear dynamics and chaos tools have been used to explain various complex biological and physiological phenomena [20, 21, 22, 23]; for example, to classify atrial fibrillations [24] and to characterize heart rate variability [25], each of where is incorporated by reference here in its entirety. Further description of these dynamical features are described in U.S. Provisional Patent Application No. 62/862,991, filed Jun. 18, 2019, entitled "Method and System to Assess Disease Using Dynamical Analysis of Biophysical Signals," which is incorporated by reference herein in its entirety.

Other invariant measures of dynamics may be used as a feature set. Deterministic dynamical systems that exhibit chaotic behavior often possess invariant properties which do not depend on when the observations are made and are thus independent of the evolution of the system.

For the synchronicity feature sets, three types of Poincaré maps were defined, and the resulting sets were characterized statistically and geometrically. The computed features set matched with appropriate labels were then used to train several machine learning models. Model were selected based on its respective AUC performance on a holdout test set. The study performed cross validation and grid searches to tune the hyperparameters used in the classifier training. In the study, a developed Elastic Net model was observed to have AUCs of 0.78 and 0.61 in CAD classification on two tested data sets. And a developed XGboost model was observed to have AUCs of 0.86 and 0.63 on two tested data sets. The study demonstrated an efficient and cost-effective means of using advanced nonlinear feature extraction processes of non-invasive modalities for machine learning operations for disease or abnormal condition prediction.

Elastic Net, Lasso, or Ridge classifiers are generally suited for smaller datasets with a large number of features because they can be adjusted to prevent overfitting. Elastic Net is a hybrid of Lasso and Ridge, where both the absolute value penalization (Lasso) and squared penalization (Ridge) are included. For each penalty, hyperparameters exist that can be optimized to generate stronger models. Lasso and Ridge only have a single hyperparameter each which makes optimization more limited.

Data description. In the study, two human subject cohorts with an average age of 63 (group A) and 28 (group B) were recruited for data collection. Subjects of the cohorts were selected after undergoing a qualification screening process. For the older group, the CAD labels and LVEDP values were determined by the corresponding gold standard tests, while the younger group was considered to be healthy by clinical criteria. That is, the younger group did not have CAD, and their LVEDP values were not abnormally high or elevated.

From each subject in groups A and B, cardiac signals (as biopotential signals) and photoplethysmographic signals as time series data were acquired. Data of both signal modalities were acquired over 3.5 minutes, and the entire procedure took about 10 minutes per subject on average. The cardiac signals were each collected at a sampling rate of 8 kHz (i.e., 8,000 samples per seconds for each of 6 channels collected over 210 seconds) using a phase space recorder as described in relation to FIGS. 3A-3E. Three differential input pairs were arranged orthogonally at a subject's thorax along with a reference lead. The acquired signals were used for feature extraction after removing baseline wander and filtering out powerline and high frequency noise.

During the same procedure in which the cardiac signals were collected from a subject, photoplethysmographic signals were collected at a sampling rate of 500 Hz using the same phase space recorder. Photo-absorption data of red and infrared channels were each recorded at 500 samples per second over the same 210 second period. These photoplethysmographic and cardiac signals were simultaneously acquired for each subject. Jitter (inter-modality jitter) in the data was less than about 10 microseconds ($\mu$s). Jitter among the cardiac signal channels was around 10 femtoseconds (fs).

CAD Feature Study. The study used a definition for significant coronary occlusions as either having greater than 70% stenosis or a patient that passed a functional threshold for blood flow limitation [14, 15]. For group A, two-vessel disease (i.e., two vessels with lesions meeting this definition) was considered as being disease-positive, and non-disease cases were defined as healthy control subjects that had undergone invasive catheterization for evaluation of coronary artery disease but did not have any coronary lesions. Table 5 lists the number of positive and negative cases in the coronary artery disease data set used in the development of coronary artery disease features for the study. Table 5 further shows the average age and gender composition associated with the subjects in the data set. The study used invasive coronary angiography, the "gold standard" for coronary artery disease, as the ground truth metric.

In coronary angiography, fluoroscopy is used to image coronary arteries following an injection of a radiopaque contrast agent. With coronary angiography, stenoses (blockages) in the arteries may be detected, and patients are subsequently labelled as CAD-positive or CAD-negative.

TABLE 5

| Group | Total | Positive | Negative | Male | Female | Age IQR |
|---|---|---|---|---|---|---|
| A | 1211 | 463 | 748 | 61% | 39% | 56-71 |
| B | 358 | 0 | 358 | 42% | 58% | 21-31 |
| Total | 1569 | 463 | 1106 | 57% | 43% | — |

The study results show that synchronicity between photoplethysmographic signals and cardiac signals, represented by way of synchronicity features from the analysis between photoplethysmographic signals and cardiac signals as described herein, can be used to predict the presence or non-presence of significant coronary artery disease.

LVDEP Feature Feasibility Study. Left ventricular end diastolic pressure (LVEDP) is an invasively-obtained hemodynamic measurement used to describe the heart's left-sided filling pressures in patients undergoing cardiac catheterization. LVEDP is a critical parameter in the hemodynamic evaluation of patients with either systolic or diastolic LV dysfunction, which are both associated with decreased LV compliance. Alterations in the pressure-volume relationships that result in markedly elevated filling pressures are the hallmark of cardiomyopathies [10].

Measurement of filling pressures may be used to assess risk stratification and the development of an appropriate treatment strategy. Furthermore, LVEDP provides important prognostic information, as elevated LVEDP has been established as an independent predictor of adverse outcomes in the setting of acute myocardial infarct [16], cardiogenic shock [17], the post-procedural success of cardiac surgery [18], and percutaneous cardiac interventions. Table 6 lists the number of positive and negative cases of LVEDP used in the evaluation of LVEDP features in the data set of Table 5.

TABLE 6

| Group | Total | High | Low | Male | Female | Age IQR |
|---|---|---|---|---|---|---|
| A | 470 | 211 | 259 | 60% | 40% | 57-71 |
| B | 418 | 0 | 418 | 42% | 58% | 21-35 |
| Total | 888 | 211 | 677 | 52% | 48% | — |

The study results show that the synchronicity between photoplethysmographic signals and cardiac signals, represented by way of synchronicity features from analysis between photoplethysmographic signals and cardiac signals as described herein, can be used to predict presence or non-presence of abnormal LVEDP.

Machine-Learning Classifier Analysis. In the study, feature sets extracted from the acquired data set, including 94 synchronicity features defined between the photoplethysmographic signals and cardiac signals (e.g., per synchronicity analysis of Poincaré maps 1, 2 and 3), as well as 6 features of the phase analysis #4, among others (e.g., dynamical features, etc.), were extracted and assessed in a machine-based classifier analysis. The feature sets including the synchronicity features were paired with the corresponding CAD or LVEDP labels and provided as input to the machine learning models. The feature sets included 36 other dynamical features associated with cardiac signals (i.e., biopotential signals), and 29 further dynamical features associated with photoplethysmographic signals were also evaluated. These features are described in U.S. patent application Ser. No. 16/831,264, entitled "Method and System to Assess Disease Using Dynamical Analysis of Biophysical Signals", concurrently filed with the instant application (and claimed priority to U.S. Provisional Patent Application No. 62/863,005, filed Jun. 18, 2019), which is incorporated by reference herein in its entirety.

In the classifier analysis, the data for CAD and LVEDP were each split into a training-validation set and a test set. Table 7 shows the composition of the training-validation and test data sets for the machine learning model training and evaluation. As noted above, information about Groups A and B for the CAD data sets are listed in Table 5 and information about Groups A and B for the LVEDP data sets are listed in Table 6.

TABLE 7

| ML Data set | Composition |
|---|---|
| Train-validation | 80% A + 50% B |
| Test 1 | 20% A + 50% B |
| Test 2 | 20% A |

The training-validation set is used to train and fine-tune candidate machine learning models using 5-fold cross validation. Table 8 lists the classifiers used in the study for training and model selection for both the CAD and LVEDP data sets. The pipeline for data scaling, model training, grid search, and model evaluation was implemented in Python using the Scikit-learn package [36].

TABLE 8

| | |
|---|---|
| 1 | Gradient tree boosting (XGBClassifier) [37] |
| 2 | K nearest neighbors classifier (KNeighborsClassifier) |
| 3 | support vector classifier (SVC) |
| 4 | Random forest classifier |
| 5 | Logistic regression |
| 6 | Elastic net (ElasticNet) [38] |

To find an optimal set of hyperparameters for each model, the study performed a grid search over a pre-defined range of hyperparameters. Using average AUC as the performance metric, the best hyper-parameters set is selected for each model. The selected models are then trained on the entire training-validation set, and their AUC performance on the holdout test sets is ranked.

In the study, the Elastic Net model and the support vector classifier model were found to be most predictive for significant CAD predictions, and the XGBoost model and Elastic Net model were found to be most predictive for an elevated or abnormal LVEDP state. Table 9 shows the predictive performance of the Elastic Net model and the support vector classifier model to predict significant CAD. Table 10 shows the predictive performance of the Elastic Net model and the XGBoost model to predict a significant CAD state.

TABLE 9

| | | AUC | | |
|---|---|---|---|---|
| Rank | Model | Training | Test 1 | Test 2 |
| 1 | Elastic net | 0.71 | 0.78 | 0.61 |
| 2 | Linear SVC | 0.75 | 0.65 | 0.52 |

TABLE 10

| Rank | Model | AUC Training | Test 1 | Test 2 |
|---|---|---|---|---|
| 1 | XGBoost | 1.0 | 0.86 | 0.63 |
| 2 | ElasticNet | 0.79 | 0.84 | 0.51 |

Figure 10A:
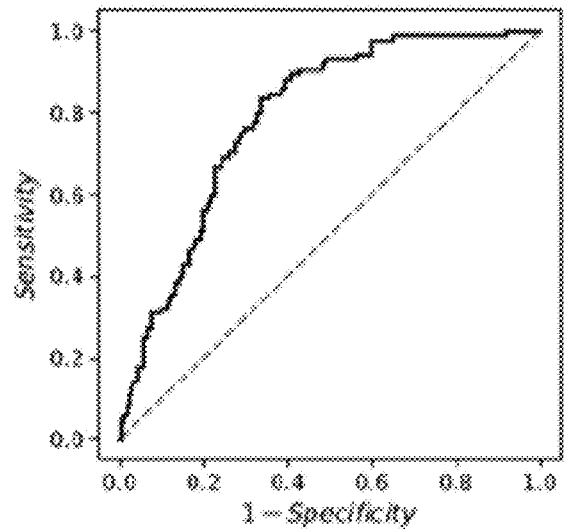
FIGS. 10A and 10B, respectively, show ROC curves of a significant CAD classification using a trained Elastic Net model on two data sets in accordance with an illustrative embodiment.
Figure 10B:
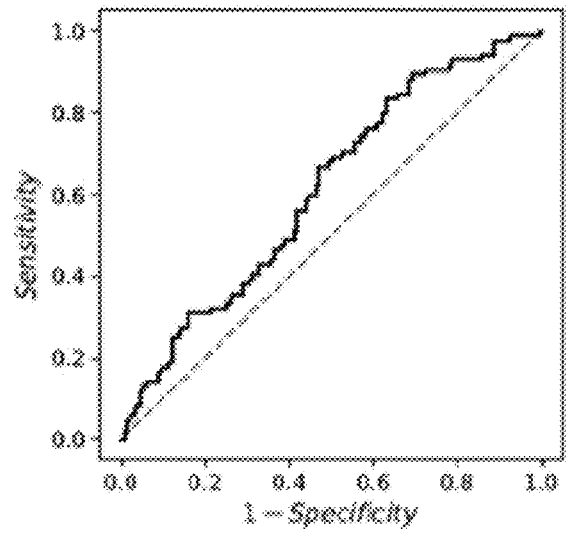
Figure 10C:
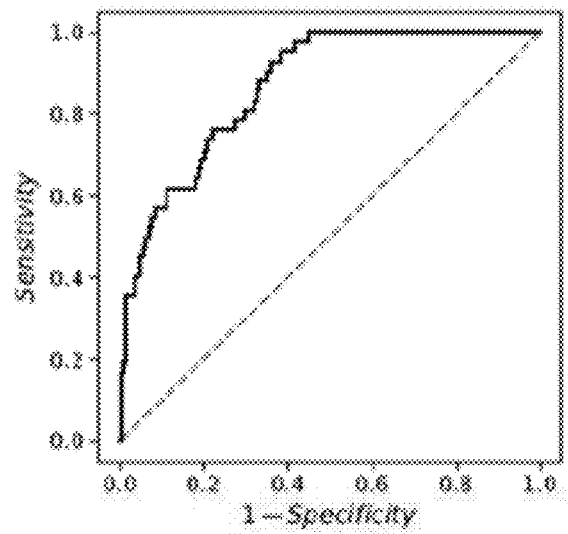
FIGS. 10C and 10D, respectively, show ROC curves of an elevated or abnormal LVEDP classification using the trained XGBoost model on two data sets in accordance with an illustrative embodiment.
Figure 10D:
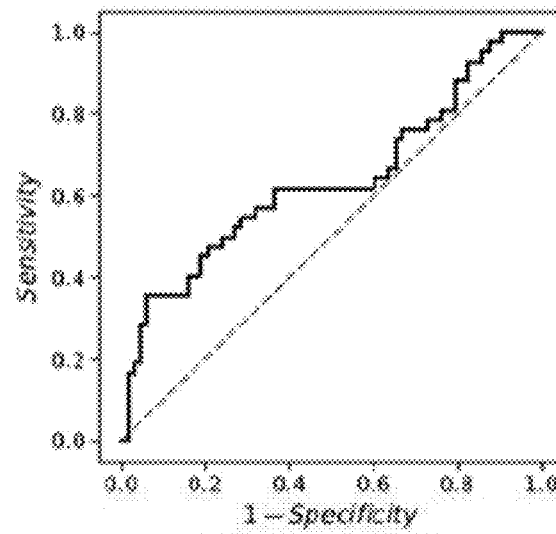

FIGS. 10A and 10B, respectively, show ROC curves of the significant CAD classification using the trained Elastic Net model on Test 1 and Test 2. FIGS. 10C and 10D, respectively, show ROC curves of the abnormal LVEDP classification using the trained XGBoost model on Test 1 and Test 2.

As shown in FIGS. 10A, 10B, 10C, and 10D, CAD and LVEDP classification tasks can achieve relatively good AUC performance. In the case of CAD predictions, AUC=0.78 on Test 1 and AUC=0.61 on Test 2 were observed. For elevated or abnormal LVEDP predictions, AUC=0.86 on Test 1 and AUC=0.63 on Test 2 were observed.

The models were trained on both Groups A and B (older and younger subjects, respectively) data sets, as described in relation to Tables 5 and 6. The use of the Group B data set augments the training of the Group A data set and allows the models to learn very healthy subjects from diseased subjects. As a result, the model honed for this task exhibits better performance on Test 1 (which contains subjects from both Groups A and B) as compared to Test 2 (which is from Group A only). Further, because the acquired data sets are skewed toward non-diseased cases, as shown in Tables 5 and 6, consequently, the trained model is better in this study at detecting CAD-negative subjects. It is expected that with data sets that are more balanced between diseased and non-diseased cases, model performance for Test 2 would be improved. XGBoost performance may also be improved by performing a more refined hyperparameter search and stronger regularization.

Further improvements to a second Elastic Net model was made using only the synchronicity feature sets and with a larger data set.

Figure 10E:
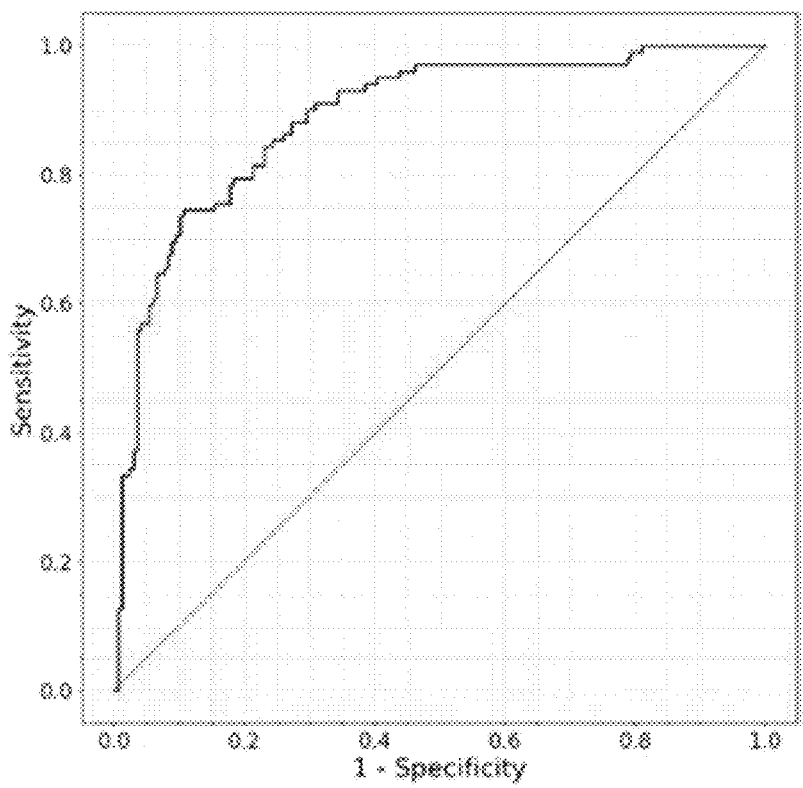
FIGS. 10E and 10F, respectively, show ROC curves for the correct classification of the presence of significant CAD and elevated or abnormal LVEDP using a subsequently trained Elastic Net model using only Poincaré-map-based features and a larger training data set in accordance with an illustrative embodiment.

FIG. 10E shows a ROC curve for the correct classification of the presence of significant CAD using a subsequently trained Elastic Net model using only the synchronicity feature sets in accordance with an illustrative embodiment.

Figure 10F:
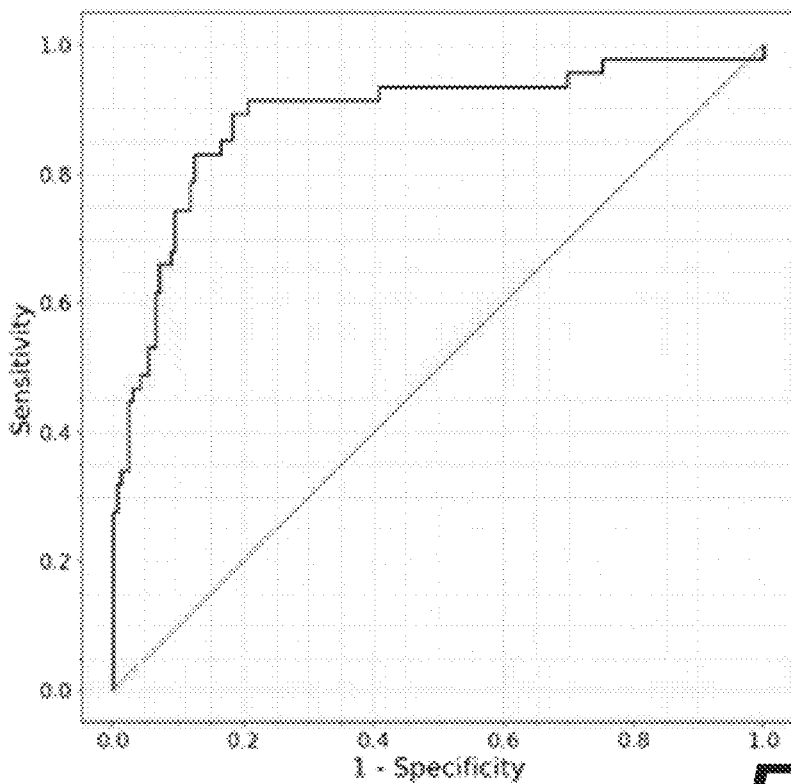

FIG. 10F shows a ROC curve of the correct classification of the presence of elevated or abnormal LVEDP using a subsequently trained Elastic Net model using only the synchronicity feature sets in accordance with an illustrative embodiment.

FIGS. 10E and 10F show that synchronicity feature sets, in combination with the features, can be used to achieve classification with high specificity and sensitivity.

Figure 10G:
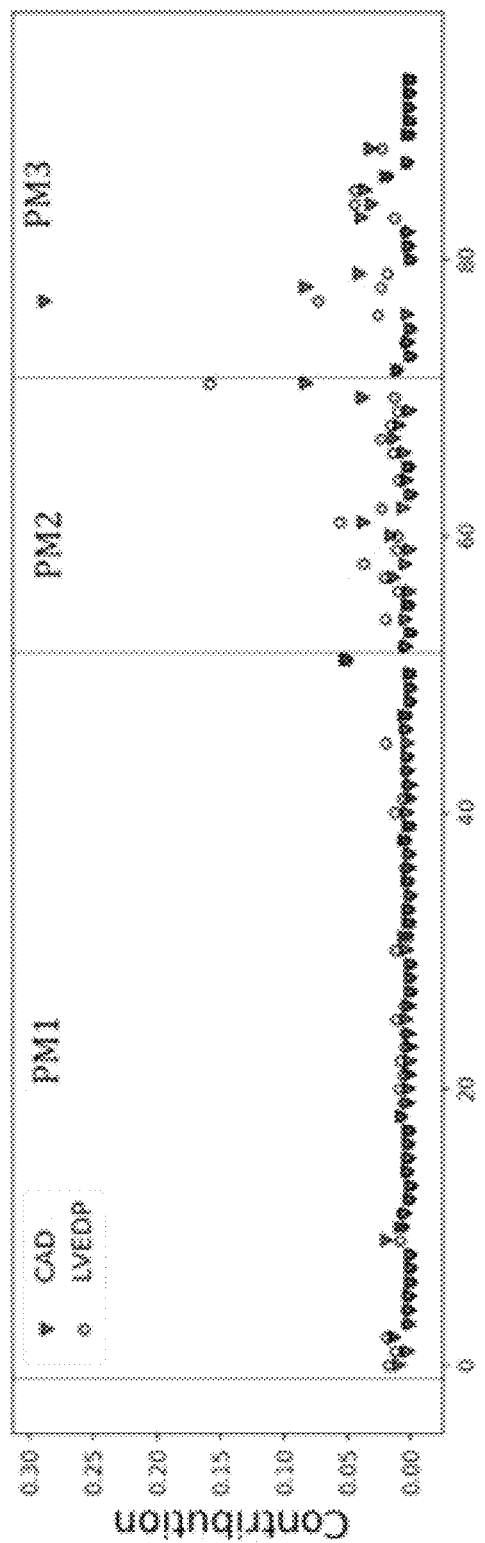
FIGS. 10G and 10H, respectively, show the feature contribution in the classifier models of FIGS. 10E and 10F for CAD and LVEDP classifications.
Figure 10H:
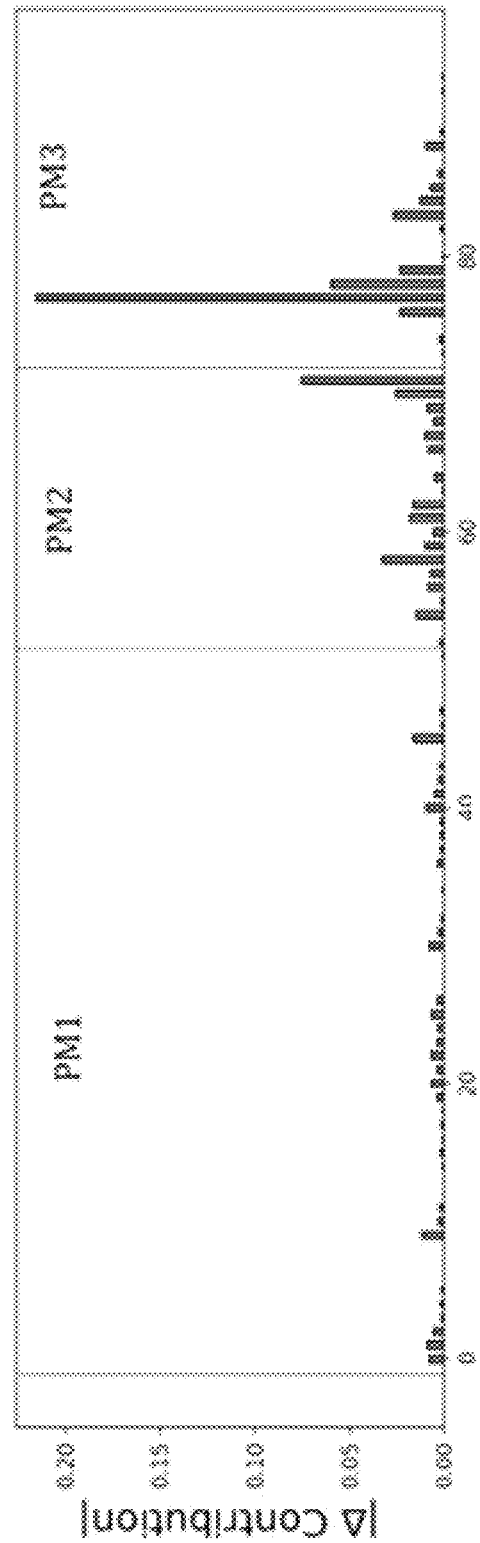

FIGS. 10G and 10H, respectively, shows the feature contribution in the classifier models of FIGS. 10E and 10F for CAD and LVEDP classifications. In FIG. 10G, features are divided into three sub-groups (PM1, PM2, PM3) based on the Poincaré Map (PM) used to generate them. In FIG. 10H, absolute values of difference in feature contributions used in LVEDP and CAD classification models are shown. Features with larger differences indicate the feature to be a more disease specific feature. Table 1 includes some of the features of PM1 as shown in FIGS. 10G and 10H. Table 2 includes some of the features of PM2 as shown in FIGS. 10G and 10H. Table 3 includes some of the features of PM3 as shown in FIGS. 10G and 10H.

Table 11 lists the accumulative feature contributions in each of the sub-groups PM1-PM3 as denoted in FIGS. 10G and 10H. As shown in Table 11, PM3 features have the highest contribution in the classification of both CAD and LVEDP, while PM1 has the lowest contribution. In Table 11, the sum of feature contribution of Poincaré maps used in the Elastic Net model for the classification of CAD and LVEDP are shown.

TABLE 11

| Target | Poincaré Map 1 | Poincaré Map 2 | Poincaré Map 3 |
|---|---|---|---|
| CAD | 0.116 | 0.207 | 0.677 |
| LVEDP | 0.214 | 0.325 | 0.461 |

Although Elastic Net classifiers were found to be the best performing model to classify CAD and LVEDP, synchronization features contribute differently across the two diseases. The absolute value of the difference in the feature contribution is plotted in FIG. 11. This reflects the utility of the synchronization features that have different distributions among LVEDP and CAD subjects. These PMs were developed based on triggers and other information that was thought to be useful from a signal perspective; the current work describes their utility in disease assessment, but the underlying physiological characteristics captured by these features are unknown, and future work will explore that mechanistic aspect.

LVDEP Feature Performance Study. A second LVDEP-related study was conducted to predict, as a primary outcome, an elevated LVEDP. This study also investigated as secondary outcomes (i) the diagnostic sensitivity of the machine-learned predictor among three sub-groups of increasing LVEDP ($\geq 20$ mmHg, $\geq 25$ mmHg, and $\geq 30$ mmHg) and (ii) the predictive performance of the predictor within an age and gender propensity matched cohort.

The second LVDEP-related study used data sets collected in the manner described herein (i.e., using a phase space recorder as described in relation to FIGS. 3A-3E) from a cardiac phase space analytic study to retrospectively develop and evaluate machine-learned predictors. Biopotential (cardiac) signals and photoplethysmographic signals were acquired from 1,919 consecutive subjects enrolled across 21 centers immediately prior to elective angiography. A comparison (control arm) of 634 healthy subjects without cardiovascular disease enrolled across 2 of the 21 sites underwent data collected in the identical manner as described for the 1,919 subjects.

Data of both signal modalities were acquired over 3.5 minutes, and the entire procedure took about 10 minutes. The biopotential signals were collected with a sampling rate of 8 KHz (i.e., 8,000 samples per second for each of 6 channels over 210 seconds). Three differential input pairs were arranged orthogonally at the patient's thorax along with a reference lead. The acquired signals were used for feature extraction after removing baseline wander and filtering powerline and high frequency noise.

Out of the 1,919 symptomatic subjects who underwent elective angiography, 256 subjects were found on catheterization to have an LVEDP$\geq$20 mmHg; these 256 subjects formed the study cohort. As noted, the patients were referred to angiography for the evaluation of symptoms, and elevated or abnormal LVEDP was determined for each patient, when present, during cardiac catheterization with direct LV pressure measurements during ventriculography.

To develop the machine learned predictors, cross-validation was performed over 100 iterations, with 70% of the subjects used for training and 30% for testing. The subjects were divided to stratify the prevalence of disease (LVEDP≥20 mmHg) across the sets, but the division was otherwise random. The training subjects' features were inputted to an Elastic Net model configured with added regularization penalties to reduce overfitting. Once trained, the model was applied to the validation subjects to assess diagnostic performance.

Figure 11A:
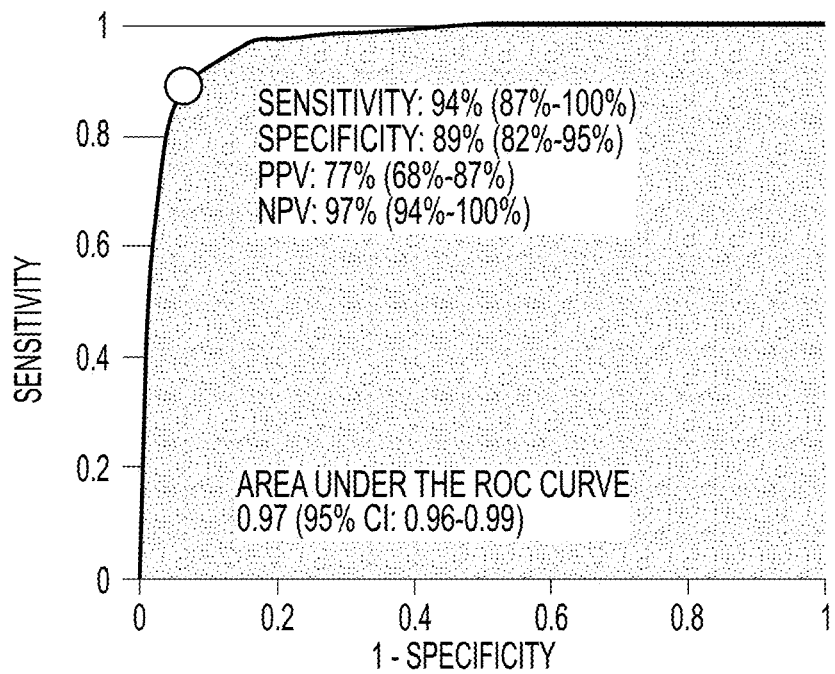

FIGS. 11A-11F show experimental results for a trained classifier to predict an elevated LVEDP in accordance with an illustrative embodiment. FIG. 11A shows show a ROC curve of classification to predict an elevated LVEDP≥20 mmHg. The classification is based on an Elastic Net model. As shown in FIG. 11A, a machine-learned cardiac phase space predictor provides a robust prediction of elevated LVEDP≥20 with an AUC of 0.97. The predictor algorithm also performs with an increasing diagnostic sensitivity across progressive increases in LVEDP. The algorithm maintained a high level of fidelity even after age and gender propensity matching with an area under the curve for prediction of LVEDP≥20 of 0.88. The ROC curve was computed with R package ROC and includes AUC, Sensitivity, specificity, PPV and NPV values.

Figure 11B:
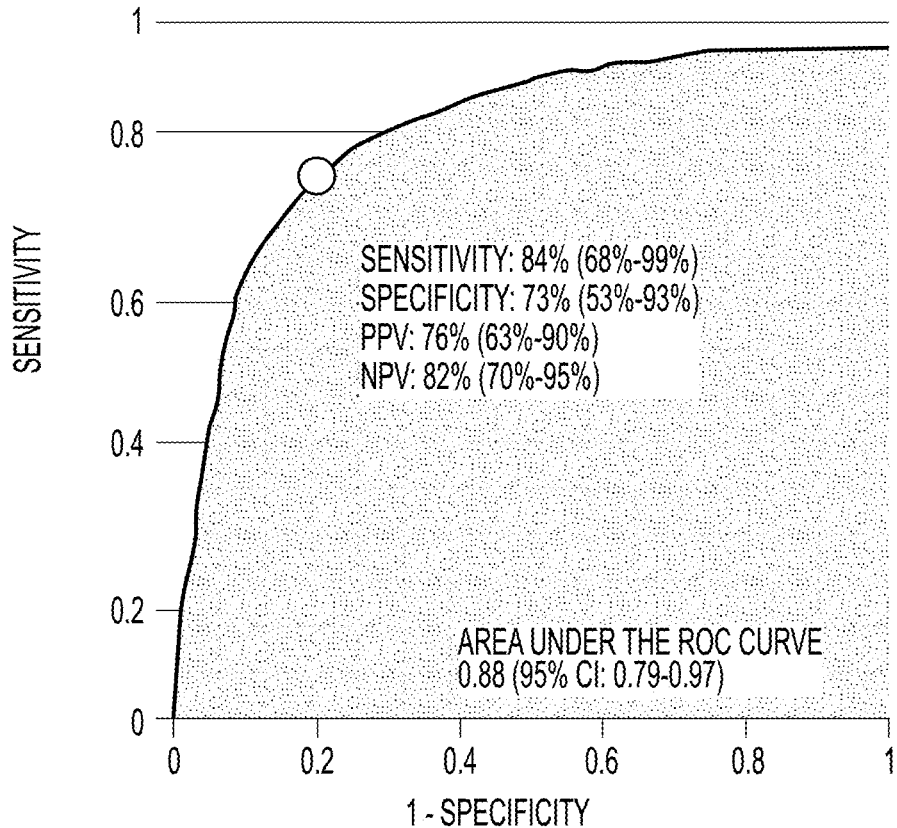

FIG. 11B shows the ROC curve illustrating the diagnostic performance of the machine-learned approach in a propensity matched secondary analysis (age and gender) to predict an LVEDP≥20 mmHg. In the analysis, subjects with elevated LVEDP were propensity matched to those with non-elevated LVEDP based on gender and age within 5 years prior to stratified division into training and testing datasets. Matching, training, and testing were then performed over 100 iterations to capture the heterogeneity of the dataset.

FIG. 11C shows results of the sensitivity of the machine-learned approach at LVEDP≥20 mmHg, LVEDP≥25 mmHg, and LVDEP≥30 mmHg in the other secondary analysis. FIGS. 11D, 11E, and 11F each respectively shows ROC curve illustrating the diagnostic performance of the machine-learned approach in a propensity matched analysis (age and gender) to predict a LVEDP≥20 mmHg, LVEDP≥25 mmHg, and LVDEP≥30 mmHg.

Healthcare Provider Portal

Referring to FIG. 1 (as well as FIGS. 1A and 1B), system 100 (e.g., 100a, 100b), in some embodiments, includes a healthcare provider portal to display an assessment of disease state or condition (e.g., associated with an abnormal LVEDP and/or the presence coronary artery disease and/or pulmonary hypertension, etc.) in a report. In some embodiments, the report is structured as an angiographic-equivalent report. The physician or clinician portal, in some embodiments, is configured to access and retrieve reports from a repository (e.g., a storage area network). The physician or clinician portal and/or repository can be HLPAA-compliant (and equivalent) and compliant with various other privacy requirements. An example healthcare provider portal is provided in U.S. patent application Ser. No. 15/712,104, entitled "Method and System for Visualization of Heart Tissue at Risk," which is incorporated by reference herein in its entirety. Although in certain embodiments, the portal is configured for the presentation of patient medical information to healthcare professionals, in other embodiments, the healthcare provider portal can be made accessible to patients, other caregivers, family members, researchers, academics, and/or others. This portal may be used for a wide variety of clinical and even research needs in a wide variety of settings—from hospitals to emergency rooms, laboratories, battlefield or remote settings, at point of care with a patient's primary care physician or other caregivers, and even the home.

Example Computing Device

Figure 12:
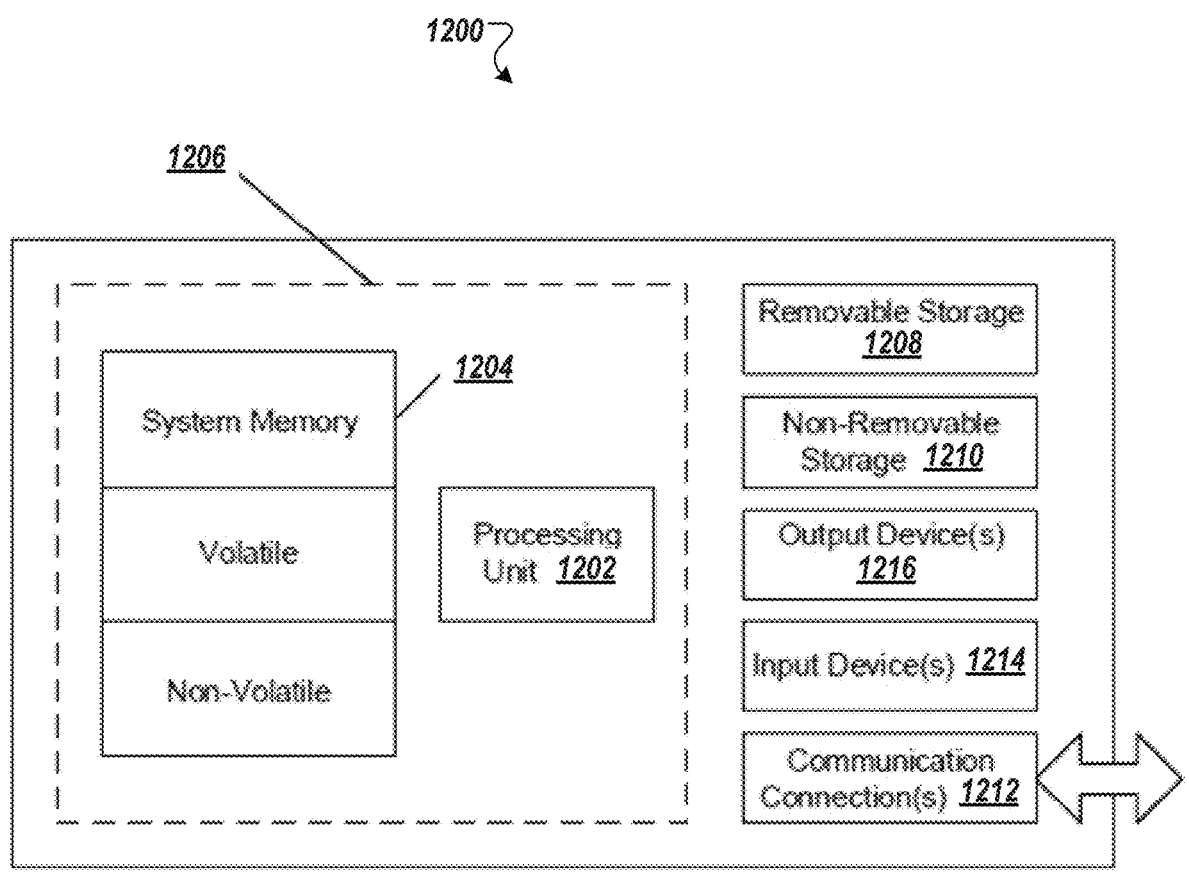
FIG. 12 shows an example computing environment in which example embodiments of the analysis system and aspects thereof may be implemented.

FIG. 12 shows an example computing environment in which example embodiments of the analysis system 114 and aspects thereof may be implemented in, e.g., a device or devices, among others.

The computing device environment is only one example of a suitable computing environment and is not intended to suggest any limitation as to the scope of use or functionality. Numerous other general-purpose or special purpose computing devices environments or configurations may be used. Examples of well-known computing devices, environments, and/or configurations that may be suitable for use include, but are not limited to, personal computers, server computers, handheld or laptop devices, mobile phones, wearable devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media, including memory storage devices.

With reference to FIG. 12, an example system for implementing aspects described herein includes a computing device, such as computing device 1000. In its most basic configuration, the computing device 1000 typically includes at least one processing unit 1002 and memory 1004. Depending on the exact configuration and type of computing device, memory 1004 may be volatile (such as random-access memory (RAM)), non-volatile (such as read-only memory (ROM), flash memory, etc.), or some combination of the two. This most basic configuration is illustrated in FIG. 12 by dashed line 1006.

Computing device 1000 may have additional features/functionality. For example, computing device 1000 may include additional storage (removable and/or non-removable) including, but not limited to, magnetic or optical disks or tape. Such additional storage is illustrated in FIG. 12 by removable storage 1008 and non-removable storage 1010.

Computing device 1000 typically includes a variety of computer readable media. Computer readable media can be any available media that can be accessed by the device 1000 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 1004, removable storage 1008, and non-removable storage 1010 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1000. Any such computer storage media may be part of computing device 1000.

Computing device 1000 may contain communication connection(s) 1012 that allow the device to communicate with other devices. Computing device 1000 may also have input device(s) 1014 such as a keyboard, mouse, pen, voice input device, touch input device, etc., singly or in combination. Output device(s) 1016 such as a display, speakers, printer, vibratory mechanism, etc. may also be included singly or in combination. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although example implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, handheld devices, and wearable devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Further examples of processing that may be used with the exemplified method and system are described in: U.S. Pat. No. 9,289,150, entitled "Non-invasive Method and System for Characterizing Cardiovascular Systems"; U.S. Pat. No. 9,655,536, entitled "Non-invasive Method and System for Characterizing Cardiovascular Systems"; U.S. Pat. No. 9,968,275, entitled "Non-invasive Method and System for Characterizing Cardiovascular Systems"; U.S. Pat. No. 8,923,958, entitled "System and Method for Evaluating an Electrophysiological Signal"; U.S. Pat. No. 9,408,543, entitled "Non-invasive Method and System for Characterizing Cardiovascular Systems and All-Cause Mortality and Sudden Cardiac Death Risk"; U.S. Pat. No. 9,955,883, entitled "Non-invasive Method and System for Characterizing Cardiovascular Systems and All-Cause Mortality and Sudden Cardiac Death Risk"; U.S. Pat. No. 9,737,229, entitled "Noninvasive Electrocardiographic Method for Estimating Mammalian Cardiac Chamber Size and Mechanical Function"; U.S. Pat. No. 10,039,468, entitled "Noninvasive Electrocardiographic Method for Estimating Mammalian Cardiac Chamber Size and Mechanical Function"; U.S. Pat. No. 9,597,021, entitled "Noninvasive Method for Estimating Glucose, Glycosylated Hemoglobin and Other Blood Constituents"; U.S. Pat. No. 9,968,265, entitled "Method and System for Characterizing Cardiovascular Systems From Single Channel Data"; U.S. Pat. No. 9,910,964, entitled "Methods and Systems Using Mathematical Analysis and Machine Learning to Diagnose Disease"; U.S. Patent Publication No. 2017/0119272, entitled "Method and Apparatus for Wide-Band Phase Gradient Signal Acquisition"; PCT Publication No. WO2017/033164, entitled "Method and Apparatus for Wide-Band Phase Gradient Signal Acquisition"; U.S. Patent Publication No. 2018/0000371, entitled "Non-invasive Method and System for Measuring Myocardial Ischemia, Stenosis Identification, Localization and Fractional Flow Reserve Estimation"; PCT Publication No. WO2017/221221, entitled "Non-invasive Method and System for Measuring Myocardial Ischemia, Stenosis Identification, Localization and Fractional Flow Reserve Estimation"; U.S. Pat. No. 10,292,596, entitled "Method and System for Visualization of Heart Tissue at Risk"; U.S. patent application Ser. No. 16/402,616, entitled "Method and System for Visualization of Heart Tissue at Risk"; U.S. Patent Publication No. 2018/0249960, entitled "Method and System for Wide-band Phase Gradient Signal Acquisition"; U.S. patent application Ser. No. 16/232,801, entitled "Method and System to Assess Disease Using Phase Space Volumetric Objects"; PCT Application No. IB/2018/060708, entitled "Method and System to Assess Disease Using Phase Space Volumetric Objects"; U.S. Patent Publication No. US2019/0117164, entitled "Methods and Systems of De-Noising Magnetic-Field Based Sensor Data of Electrophysiological Signals"; U.S. patent application Ser. No. 16/232,586, entitled "Method and System to Assess Disease Using Phase Space Tomography and Machine Learning"; PCT Application No. PCT/IB2018/060709, entitled "Method and System to Assess Disease Using Phase Space Tomography and Machine Learning"; U.S. patent application Ser. No. 16/445,158, entitled "Methods and Systems to Quantify and Remove Asynchronous Noise in Biophysical Signals"; U.S. patent application Ser. No. 16/725,402, entitled "Method and System to Assess Disease Using Phase Space Tomography and Machine Learning"; U.S. patent application Ser. No. 16/429,593, entitled "Method and System to Assess Pulmonary Hypertension Using Phase Space Tomography and Machine Learning"; U.S. patent application Ser. No. 16/725,416, entitled "Method and System for Automated Quantification of Signal Quality"; U.S. patent application Ser. No. 16/725,430, entitled "Method and System to Configure and Use Neural Network To Assess Medical Disease"; U.S. patent application Ser. No. 15/653,433, entitled "Discovering Novel Features to Use in Machine Learning Techniques, such as Machine Learning Techniques for Diagnosing Medical Conditions"; U.S. patent application Ser. No. 15/653,431, entitled "Discovering Genomes to Use in Machine Learning Techniques", each of which is incorporated by reference herein in its entirety.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; the number or type of embodiments described in the specification.

While the methods and systems have been described in connection with certain embodiments and specific examples, it is not intended that the scope be limited to the particular embodiments set forth, as the embodiments herein are intended in all respects to be illustrative rather than restrictive.

The methods, systems and processes described herein may be used to generate stenosis and FFR outputs for use in connection with procedures such as the placement of vascular stents within a vessel such as an artery of a living (e.g., human) subject, and other interventional and surgical system or processes. In one embodiment, the methods, systems and processes described herein can be configured to use the FFR/stenosis outputs to determine and/or modify, intra operation, a number of stents to be placed in a living (e.g., human), including their optimal location of deployment within a given vessel, among others.

Examples of other biophysical signals that may be analyzed in whole, or in part, using the example methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The example analysis can be used in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD, and other diseases and conditions disclosed herein and its treatment by any number of therapies, alone or in combination, such as the placement of a stent in a coronary artery, the performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

The following patents, applications and publications as listed below and throughout this document are hereby incorporated by reference in their entirety herein.

LIST OF REFERENCES

[1] I. Kononenko, "Machine learning for medical diagnosis: history, state of the art and perspective," Artificial Intelligence in medicine 23 (1) 89-109 (2001).

[2] B. A. Mobley, E. Schechter, W. E. Moore, P. A. McKee, J. E. Eichner, "Predictions of coronary artery stenosis by artificial neural network," Artificial Intelligence in Medicine 18 (3) 187-203 (2000).

[3] V. L. Patel, E. H. Shortliffe, M. Stefanelli, P. Szolovits, M. R. Berthold, R. Bellazzi, A. Abu-Hanna, "The coming of age of artificial intelligence in medicine," Artificial intelligence in medicine 46 (1) 5-17 (2009).

[4] V. Jahmunah, S. L. Oh, V. Rajinikanth, E. J. Ciaccio, K. H. Cheong, U. R. Acharya, et al., "Automated detection of schizophrenia using nonlinear signal processing methods," Artificial Intelligence in Medicine, Vol. 100, 101698 (September 2019).

[5] A. M. Tai, A. Albuquerque, N. E. Carmona, M. Subramanieapillai, D. S. Cha, M. Sheko, Y. Lee, R. Mansur, R. S. McIntyre, "Machine learning and big data: Implications for disease modeling and therapeutic discovery in psychiatry," Artificial Intelligence in Medicine 101704 (2019).

[6] G. K. Hansson, "Inflammation, atherosclerosis, and coronary artery disease," New England Journal of Medicine 352 (16) 1685-1695 (2005).

[7] W. G. Members, D. Lloyd-Jones, R. J. Adams, T. M. Brown, M. Carnethon, S. Dai, G. De Simone, T. B. Ferguson, E. Ford, K. Furie, et al., "Executive summary: heart disease and stroke statistics 2010 update: a report from the American heart association," Circulation 121 (7) 948-954 (2010).

[8] G. A. Mensah, D. W. Brown, "An overview of cardiovascular disease burden in the united states," Health affairs 26 (1) 38-48 (2007).

[9] Y. N. Reddy, A. El-Sabbagh, R. A. Nishimura, "Comparing pulmonary arterial wedge pressure and left ventricular end diastolic pressure for assessment of left-sided filling pressures," JAMA cardiology 3 (6) 453-454 (2018).

[10] M. J. Kern, T. Christopher, "Hemodynamic rounds series II: the LVEDP," Catheterization and cardiovascular diagnosis 44 (1) 70-74 (1998).

[11] J.-H. Park, T. H. Marwick, "Use and limitations of e/e' to assess left ventricular filling pressure by echocardiography," Journal of cardiovascular ultrasound 19 (4) 169-173 (2011).

[12] S. R. Ommen, R. A. Nishimura, C. P. Appleton, F. Miller, J. K. Oh, M. M. Redfield, A. Tajik, "Clinical utility of doppler echocardiography and tissue doppler imaging in the estimation of left ventricular filling pressures: a comparative simultaneous doppler-catheterization study," Circulation 102 (15) 1788-1794 (2000).
[13] J. Allen, "Photoplethysmography and its application in clinical physiological measurement," Physiological measurement 28 (3) R1 (2007).
[14] S. D. Fihn, J. M. Gardin, J. Abrams, K. Berra, J. C. Blankenship, A. P. Dallas, P. S. Douglas, J. M. Foody, T. C. Gerber, A. L. Hinderliter, et al., "2012 accf/aha/acp/aats/pcna/scai/sts guideline for the diagnosis and management of patients with stable ischemic heart disease.," Journal of the American College of Cardiology 60 (24) 2564-2603 (2012).
[15] G. N. Levine, E. R. Bates, J. C. Blankenship, S. R. Bailey, J. A. Bittl, B. Cercek, C. E. Chambers, S. G. Ellis, R. A. Guyton, S. M. Hollenberg, et al., "2011 accf/aha/scai guideline for percutaneous coronary intervention: executive summary.," Journal of the American College of Cardiology 58 (24) 2550-2583 (2011).
[16] L. M. Mielniczuk, G. A. Lamas, G. C. Flaker, G. Mitchell, S. C. Smith, B. J. Gersh, S. D. Solomon, L. A. Moyé, J. L. Rouleau, J. D. Rutherford, et al., "Left ventricular end-diastolic pressure and risk of subsequent heart failure in patients following an acute myocardial infarction," Congestive Heart Failure 13 (4) 209-214 (2007).
[17] J. J. Russo, N. Aleksova, I. Pitcher, E. Couture, S. Parlow, M. Faraz, S. Visintini, T. Simard, P. Di Santo, R. Mathew, et al., "Left ventricular unloading during extracorporeal membrane oxygenation in patients with cardiogenic shock," Journal of the American College of Cardiology 73 (6) 654-662 (2019).
[18] R. Salem, A. Denault, P. Couture, S. Belisle, A. Fortier, M.-C. Guertin, M. Carrier, R. Martineau, "Left ventricular end-diastolic pressure is a predictor of mortality in cardiac surgery independently of left ventricular ejection fraction," BJA: British Journal of Anaesthesia 97 (3) 292-297 (2006).
[19] S. H. Strogatz, "Nonlinear dynamics and chaos: with applications to physics, biology, chemistry, and engineering," CRC Press, (2018).
[20] A. L. Goldberger, D. R. Rigney, B. J. West, "Chaos and fractals in human physiology," Scientific American 262 (2) 42-49 (1990).
[21] A. L. Goldberger, "Nonlinear dynamics, fractals and chaos: applications to cardiac electrophysiology," Annals of biomedical engineering 18 (2) 195-198 (1990).
[22] L. Glass, A. Beuter, D. Larocque, "Time delays, oscillations, and chaos in physiological control systems," Mathematical Biosciences 90 (1-2) 111-125 (1988).
[23] L. Glass, "Synchronization and rhythmic processes in physiology," Nature 410 (6825) 277 (2001).
[24] M. I. Owis, A. H. Abou-Zied, A.-B. Youssef, Y. M. Kadah, "Study of features based on nonlinear dynamical modeling in ecg arrhythmia detection and classification," IEEE transactions on Biomedical Engineering 49 (7) 733-736 (2002).
[25] A. Voss, S. Schulz, R. Schroeder, M. Baumert, P. Caminal, "Methods derived from nonlinear dynamics for analysing heart rate variability, Philosophical Transactions of the Royal Society A: Mathematical," Physical and Engineering Sciences 367 (1887) 277-296 (2008).
[26] L. Glass, P. Hunter, A. McCulloch, "Theory of heart: biomechanics, biophysics, and nonlinear dynamics of cardiac function," Springer Science & Business Media, (2012).
[27] P. Billingsley, "Ergodic theory and information," Vol. 1, Wiley New York, 1965.
[28] T. Sauer, J. A. Yorke, M. Casdagli, "Embedology," Journal of statistical Physics 65 (3-4) 579-616 (1991).
[29] A. Chatterjee, "An introduction to the proper orthogonal decomposition," Current science 808-817 (2000).
[30] A. Wolf, J. B. Swift, H. L. Swinney, J. A. Vastano, "Determining Lyapunov exponents from a time series," Physica D: Nonlinear Phenomena 16 (3) 285-317 (1985).
[31] A. N. Kolmogorov, "Entropy per unit time as a metric invariant of automorphisms," Doklady of Russian Academy of Sciences, Vol. 124, pp. 754-755 (1959).
[32] P. Grassberger, I. Procaccia, "Estimation of the kolmogorov entropy from a chaotic signal," Physical review A 28 (4) 2591 (1983).
[33] J. Theiler, "Efficient algorithm for estimating the correlation dimension from a set of discrete points," Physical review A 36 (9) 4456 (1987).
[34] A. Pikovsky, J. Kurths, M. Rosenblum, J. Kurths, "Synchronization: a universal concept in nonlinear sciences," Vol. 12, Cambridge university press (2003).
[35] D. Dubin, "Rapid interpretation of EKG's: an interactive course," Cover Publishing Company (2000).
[36] F. Pedregosa, G. Varoquaux, A. Gramfort, V. Michel, B. Thirion, O. Grisel, M. Blondel, P. Prettenhofer, R. Weiss, V. Dubourg, et al., "Scikit-learn: Machine learning in python," Journal of machine learning research 12, 2825-2830 (October 2011).
[37] T. Chen, C. Guestrin, "Xgboost: A scalable tree boosting system," Proceedings of the 22nd acm-sigkdd international conference on knowledge discovery and data mining, ACM, pp. 785-794 (2016).
[38] H. Zou, T. Hastie, "Regularization and variable selection via the elastic net," Journal of the royal statistical society: series B (statistical methodology) 67 (2) 301-320 (2005).

What is claimed is:

1. A method for non-invasively assessing elevated or abnormal left ventricular end-diastolic pressure (LVEDP) of a subject, the method comprising:

obtaining, by one or more processors, a first biophysical signal data set associated with a first photoplethysmographic signal, wherein the first photoplethysmographic signal has been acquired over multiple cardiac cycles of the subject;

obtaining, by the one or more processors, a second biophysical signal data set associated with a cardiac signal, wherein the cardiac signal has been acquired over the multiple cardiac cycles, and wherein the first photoplethysmographic signal and the cardiac signal are concurrently acquired via surface sensors placed on the subject;

determining, by the one or more processors, utilizing at least a portion of the first and second biophysical signal data sets, over at least a portion of the multiple cardiac cycles, (i) a plurality of peaks in the cardiac signal and (ii) values of the first photoplethysmographic signal temporally corresponding to the plurality of determined peaks in the cardiac signal;

determining, by the one or more processors, a value of a first synchronicity feature comprising (i) a geometric parameter of a Poincaré map or (ii) a statistical parameter of a histogram, wherein the Poincaré map or the histogram is defined by the values of the first photoplethysmographic signal temporally corresponding to the plurality of determined peaks in the cardiac signal; and determining, by the one or more processors, via a trained classifier model, an estimated value related to a presence of the elevated or abnormal LVEDP using the determined value of the first synchronicity feature; and outputting, via a report and/or display, the estimated value indicative of the presence of the elevated or abnormal LVEDP, wherein the output is made available to a healthcare provider to assist in a diagnosis of the elevated or abnormal LVEDP or to direct treatment of the elevated or abnormal LVEDP.

2. The method of claim 1, further comprising:

determining, by the one or more processors, utilizing the at least the portion of the first and second biophysical signal data sets, over the at least the portion of the multiple cardiac cycles, (i) a plurality of crossover points defined between the first photoplethysmographic signal and a second photoplethysmographic signal and (ii) values of the cardiac signal temporally corresponding to the plurality of determined crossover points;

determining, by the one or more processors, a value of a second synchronicity feature comprising (i) a second geometric parameter of a second Poincaré map or (ii) a second statistical parameter of a second histogram, wherein the second Poincaré map or the second histogram is defined by the values of the cardiac signal temporally corresponding to the plurality of determined crossover points; and wherein the value of the second synchronicity feature is used in the trained classifier model or a second trained classifier model to estimate the value for the presence of the elevated or abnormal LVEDP.

3. The method of claim 2, wherein the second Poincaré map is generated by iteratively plotting i) in a first axis, at a first index x and a second index x+1, values of the first photoplethysmographic signal and ii) in a second axis, at the first index x and the second index x+1, values of the cardiac signal.

4. The method of claim 2, wherein the second value associated with the second synchronicity feature is determined from the statistical analysis or the dynamical analysis of the values of one of the first and second photoplethysmographic signals at the landmark defined in the cardiac signal.

5. The method of claim 1, wherein the plurality of peaks in the cardiac signal are associated with ventricular depolarization.

6. The method of claim 1, wherein the plurality of peaks in the cardiac signal are associated with ventricular repolarization or atrial depolarization.

7. The method of claim 2, wherein the second synchronicity feature is the second geometric parameter, wherein the second geometric parameter is determined based on a shape fitted to a cluster of points in the second Poincaré map, and wherein the second geometric parameter comprises a diameter or an angle of the shape fitted to the cluster.

8. The method of claim 1, wherein the first and second biophysical signal data sets are obtained and analyzed to investigate complex, non-linear variability of the heart.

9. The method of claim 7, wherein the plurality of peaks in the cardiac signal are associated with ventricular depolarization, ventricular repolarization, or atrial depolarization.

10. The method of claim 1 further comprising:

determining, by the one or more processors, a value of a third synchronicity feature comprising a third statistical parameter of phase difference values between a plurality of periods of the first photoplethysmographic signal and a plurality of periods of the cardiac signal.

11. The method of claim 10, wherein the third statistical parameter of phase difference values is selected from a group consisting of mean, mode, median, skew, kurtosis, skewness, and standard deviation of one or more distributions defined in the third histogram.

12. The method of claim 1 further comprising:

causing, by the one or more processors, generation of a visualization of a receiver-operator-characteristic (ROC) curve associated with the estimated value indicative of the presence of the elevated or abnormal LVEDP, wherein the generated visualization is rendered and displayed at the display and/or presented in the report.

13. The method of claim 1, wherein the statistical parameter of the histogram is selected from a group consisting of mean, mode, median, skew, kurtosis, skewness, and standard deviation of one or more distributions defined in the histogram.

14. The method of claim 2, wherein the first value associated with the first synchronicity feature are is determined by:

determining, by the one or more processors, a Poincaré map of the values of the cardiac signal, the values of the one or second photoplethysmographic signal, the time interval values, or the phase relation values determined from the analysis; and determining a value of a geometric parameter a shape fitted to a cluster defined in the Poincaré map, wherein the value of the geometric parameter is used in the determining of the estimated value for the presence of the elevated or abnormal LVEDP.

15. The method of claim 14, wherein the Poincaré map is generated by iteratively plotting i) in a first axis, at a first index x−1 and a second index x, values of the first photoplethysmographic signal and ii) in a second axis, at the second index x and a third index x+1, values of the first photoplethysmographic signal.

16. The method of claim 1 further comprising:

determining, by the one or more processors, over a portion of the multiple cardiac cycles, (i) a plurality of first crossover points at a plurality of first intersection points defined between the first photoplethysmographic signal and a second photoplethysmographic signal and (ii) a plurality of first time interval values defined between the plurality of first crossover points and the plurality of peaks in the cardiac signal; and determining, by the one or more processors, a value of a fourth synchronicity feature comprising (i) a third geometric parameter of a third Poincaré map or (ii) a third statistical parameter of a third histogram, wherein the third Poincaré map or the third histogram is defined by the first time interval values defined between the plurality of first crossover points and the plurality of peaks in the cardiac signal, wherein the value of the fourth synchronicity feature is used in the trained classifier model or a third trained classifier model to estimate the value for the presence of the elevated or abnormal LVEDP.

17. The method of claim 16 further comprising:

determining, by the one or more processors, (i) a plurality of second crossover points at each second intersection of the first photoplethysmographic signal and the second photoplethysmographic signal for the given cycle and (ii) a plurality of second time interval values defined between the plurality of second crossover points and the plurality of peaks in the cardiac signal;

determining, by the one or more processors, values of a fourth synchronicity feature comprising (i) a fourth geometric parameter of a fourth Poincaré map or (ii) a fourth statistical parameter of a fourth histogram, wherein the fourth Poincaré map or the fourth histogram is defined by the plurality of second time interval values defined between the plurality of second crossover points and the plurality of peaks in the cardiac signal.

18. The method of claim 14, wherein the values of one of the first or second photoplethysmographic signals are amplitude signal values of at a respective landmark defined in the cardiac signal.

19. A system comprising:
one or more processors; and
a memory having instructions stored thereon, wherein execution of the instructions by the one or more processors cause the one or more processors to:
obtain a first biophysical signal data set associated with a first photoplethysmographic signal,
wherein the first photoplethysmographic signal has been acquired over multiple cardiac cycles of the subject;
obtain a second biophysical signal data set associated with a cardiac signal,
wherein the cardiac signal has been acquired over the multiple cardiac cycles, and wherein the first photoplethysmographic signal and the cardiac signal are concurrently acquired via surface sensors placed on the subject;
determine, utilizing at least a portion of the first and second biophysical signal data sets, over at least a portion of the multiple cardiac cycles, (i) a plurality of peaks in the cardiac signal and (ii) values of the first photoplethysmographic signal temporally corresponding to the plurality of determined peaks in the cardiac signal;
determining, by the one or more processors, a value of a first synchronicity feature comprising (i) a geometric parameter of a Poincaré map or (ii) a statistical parameter of a histogram, wherein the Poincaré map or the histogram is defined by the values of the first photoplethysmographic signal temporally corresponding to the plurality of determined peaks in the cardiac signal; and
determine, via a trained classifier model, an estimated value related to a presence of an elevated or abnormal LVEDP using the determined value of the first synchronicity feature; and
output, via a report and/or display, the estimated value indicative of the presence of the elevated or abnormal LVEDP, wherein the output is made available to a healthcare provider to assist in a diagnosis or to direct treatment of the elevated or abnormal LVEDP.

20. A non-transitory computer readable medium having instructions stored thereon, wherein execution of the instructions by one or more processors cause the one or more processors to:
obtain a first biophysical signal data set associated with a first photoplethysmographic signal,
wherein the first photoplethysmographic signal has been acquired over multiple cardiac cycles of the subject;
obtain a second biophysical signal data set associated with a cardiac signal,
wherein the cardiac signal has been acquired over the multiple cardiac cycles, and wherein the first photoplethysmographic signal and the cardiac signal are concurrently acquired via surface sensors placed on the subject;
determine, utilizing the first and second biophysical signal data sets, over at least a portion of the multiple cardiac cycles, (i) a plurality of peaks in the cardiac signal and (ii) values of the first photoplethysmographic signal temporally corresponding to the plurality of determined peaks in the cardiac signal;
determining, by the one or more processors, a value of a first synchronicity feature comprising (i) a geometric parameter of a Poincaré map or (ii) a statistical parameter of a histogram, wherein the Poincaré map or the histogram are defined by the values of the first photoplethysmographic signal temporally corresponding to the plurality of determined peaks in the cardiac signal;
determine, via a trained classifier model, an estimated value indicative of a presence of an elevated or abnormal LVEDP using the determined value of the first synchronicity feature; and
output, via a report and/or display, the estimated value related to the presence of the elevated or abnormal LVEDP, wherein the output is made available to a healthcare provider to assist in a diagnosis or to direct treatment of the elevated or abnormal LVEDP.

21. The method of claim 1,
wherein the trained classifier model is selected from the group consisting of a trained gradient tree boosting classifier, a trained K-nearest neighbor classifier, a trained support vector classifier, a trained random forest classifier, a trained logistic regression classifier, a trained elastic net classifier, and a trained lasso or ridge classifier.

* * * * *